(12) United States Patent
Schmuelling et al.

(10) Patent No.: US 10,508,281 B2
(45) Date of Patent: Dec. 17, 2019

(54) DISRUPTION OF ROCK1 GENE LEADS TO PLANTS WITH IMPROVED TRAITS

(71) Applicants: Thomas Schmuelling, Berlin (DE); Michael Niemann, Berlin (DE); Werner Tomàs, Berlin (DE)

(72) Inventors: Thomas Schmuelling, Berlin (DE); Michael Niemann, Berlin (DE); Werner Tomàs, Berlin (DE)

( * ) Notice: Subject to any disclaimer, the term of this patent is extended or adjusted under 35 U.S.C. 154(b) by 0 days.

(21) Appl. No.: 15/522,467

(22) PCT Filed: Nov. 9, 2015

(86) PCT No.: PCT/EP2015/076008
§ 371 (c)(1),
(2) Date: Apr. 27, 2017

(87) PCT Pub. No.: WO2016/075059
PCT Pub. Date: May 19, 2016

(65) Prior Publication Data
US 2018/0355363 A1    Dec. 13, 2018

(30) Foreign Application Priority Data

Nov. 12, 2014 (EP) .................................. 14192882

(51) Int. Cl.
*C12N 15/82* (2006.01)
*C12N 15/00* (2006.01)

(52) U.S. Cl.
CPC ..... *C12N 15/8261* (2013.01); *C12N 15/8205* (2013.01); *C12N 15/8213* (2013.01); *C12N 15/8218* (2013.01); *C12N 15/8241* (2013.01); *C12N 15/00* (2013.01)

(58) Field of Classification Search
None
See application file for complete search history.

(56) References Cited

U.S. PATENT DOCUMENTS

2006/0150283 A1   7/2006   Alexandrov et al.

FOREIGN PATENT DOCUMENTS

| EP | 1033405 | 9/2000 |
|----|---------|--------|
| WO | 2011004005 | 1/2011 |

OTHER PUBLICATIONS

Alonso et al. Genome-wide insertional mutagenesis of *Arabidopsis thaliana*. Science. Aug. 1, 2003;301(5633):653-7. (Year: 2003).*
Dobritsa et al. A large-scale genetic screen in *Arabidopsis* to identify genes involved in pollen exine production. Plant Physiol. Oct. 2011;157(2):947-70. Epub Aug. 17, 2011. (Year: 2011).*
Sjolander. Phylogenonnic inference of protein molecular function: advances and challenges. Bioinformatics. Jan. 22, 2004;20(2):170-9. (Year: 2004).*
A. A. Dobritsa et al: "A Large-Scale Genetic Screen in *Arabidopsis* to Identify Genes Involved in Pollen Exine Production", Plant Physiology., vol. 157, No. 2, Aug. 17, 2011(Aug. 17, 2011), pp. 947-970.
Werner T et al: "Cytokinin action in plant development", Current Opinion in Plant Biology, Quadrant Subscription Services, GB, vol. 12, No. 5, Oct. 1, 2009(Oct. 1, 2009), pp. 527-538.
Michael C. E. Niemann et al: "*Arabidopsis* ROCK1 transports UDP-GlcNAc/UDP-GalNAc and regulates ER protein quality control and cytokinin activity", Proceedings of the National Academy of Sciences, vol. 112, No. 1, Dec. 22, 2014 (Dec. 22, 2014), pp. 291-296.
International Search Report mailed in PCT/EP2015/076008 dated Apr. 25, 2016.

* cited by examiner

*Primary Examiner* — Cynthia E Collins
(74) *Attorney, Agent, or Firm* — Fox Rothschild LLP

(57) ABSTRACT

The present invention provides a method for improving traits in a plant, like e.g. improving yield-related traits like number of flowers, number of siliques, seed yield, stein growth in a plant, the method comprising disruption of endogenous ROCK1 gene in a plant cell, wherein said disruption inhibits expression and/or activity of a product of said endogenous ROCK1 gene compared to a corresponding control plant cell lacking such a disruption.

9 Claims, 4 Drawing Sheets

Figure 1:
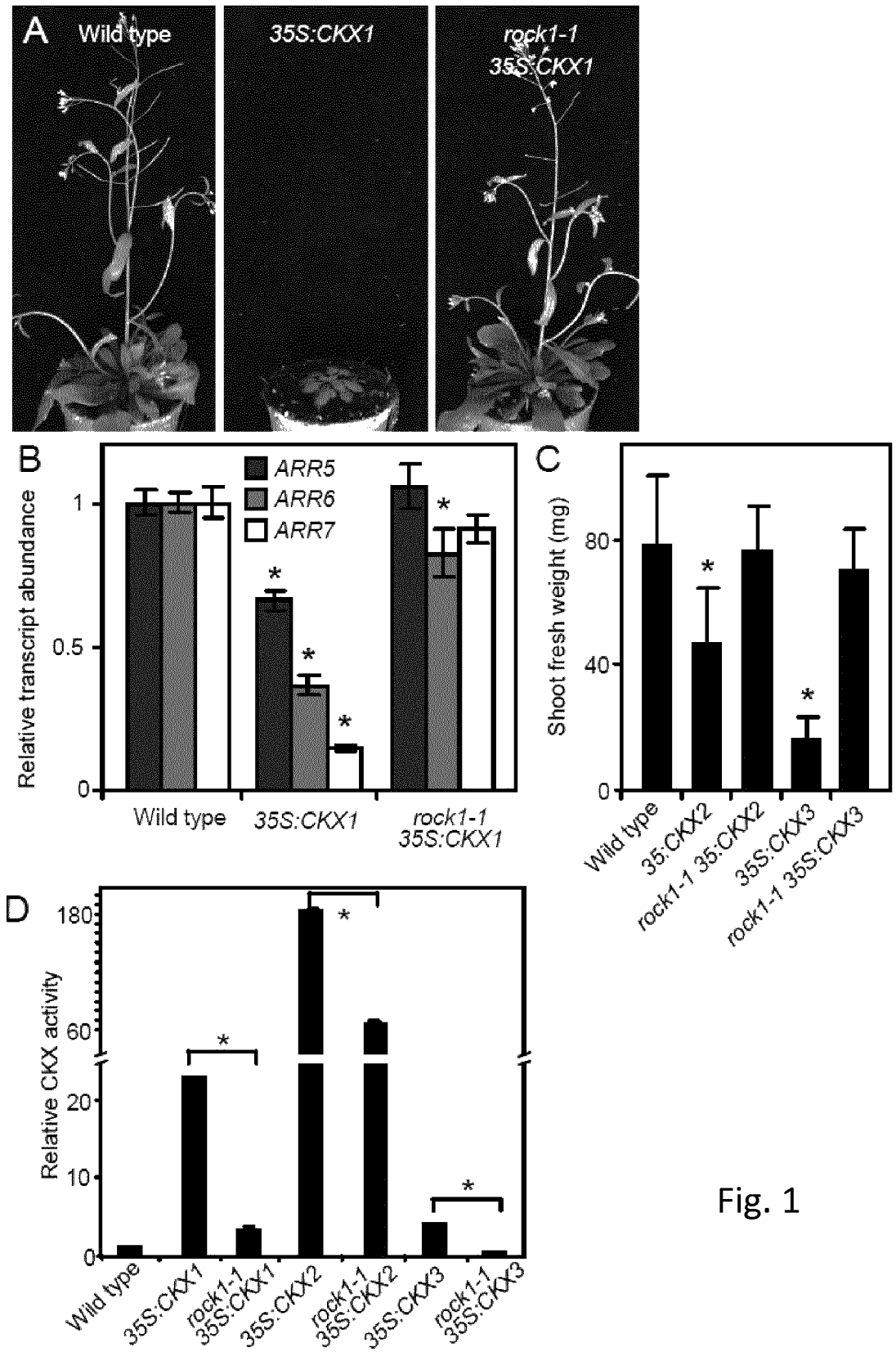

Specification includes a Sequence Listing.

SEQUENCE LISTING

<160> NUMBER OF SEQ ID NOS: 120

<210> SEQ ID NO 1
<211> LENGTH: 325
<212> TYPE: PRT
<213> ORGANISM: Arabidopsis thaliana

<400> SEQUENCE: 1

Met Ala Thr Ala Asn Gly Ala Lys Ser Pro Ser Ser Met Gly Pro Lys
1               5                   10                  15

Val Leu Phe Tyr Ser Ile Leu Leu Thr Leu Gln Tyr Gly Ala Gln Pro
            20                  25                  30

Leu Ile Ser Lys Arg Cys Ile Arg Lys Asp Val Ile Val Thr Ser Ser
        35                  40                  45

Val Leu Thr Cys Glu Ile Val Lys Val Ile Cys Ala Leu Ile Leu Met
    50                  55                  60

Ala Arg Asn Gly Ser Leu Lys Gly Leu Ala Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Ile Leu Gln Ile Gly Ala Leu Cys
130                 135                 140

Leu Leu Ile Met Ala Ala Val Leu Leu Ser Val Gly Glu Gly Ser Asn
145                 150                 155                 160

Lys Asp Ser Ser Gly Ile Asn Ala Asp Gln Lys Leu Phe Tyr Gly Ile
                165                 170                 175

Ile Pro Val Leu Ala Ala Ser Val Leu Ser Gly Leu Ala Ser Ser Leu
            180                 185                 190

Cys Gln Trp Ala Ser Gln Val Lys Lys His Ser Ser Tyr Leu Met Thr
        195                 200                 205

Val Glu Met Ser Ile Val Gly Ser Leu Cys Leu Leu Val Ser Thr Leu
    210                 215                 220

Lys Ser Pro Asp Gly Glu Ala Ile Lys Lys Tyr Gly Phe Phe His Gly
225                 230                 235                 240

Trp Thr Ala Leu Thr Leu Val Pro Val Ile Ser Asn Ala Leu Gly Gly
                245                 250                 255

Ile Leu Val Gly Leu Val Thr Ser His Ala Gly Gly Val Arg Lys Gly
            260                 265                 270

Phe Val Ile Val Ser Ala Leu Leu Val Thr Ala Leu Leu Gln Phe Ala
        275                 280                 285

```
Phe Glu Gly Lys Pro Pro Ser Ser Tyr Cys Leu Val Ala Leu Pro Leu
        290                 295                 300

Val Met Ser Ser Ile Ser Met Tyr Gln Lys Tyr Pro Tyr Ile Asp Lys
305                 310                 315                 320

Lys Lys Lys Lys Val
                325

<210> SEQ ID NO 2
<211> LENGTH: 260
<212> TYPE: PRT
<213> ORGANISM: Arabidopsis thaliana

<400> SEQUENCE: 2

Met Ala Thr Ala Asn Gly Ala Lys Ser Pro Ser Ser Met Gly Pro Lys
1               5                   10                  15

Val Leu Phe Tyr Ser Ile Leu Leu Thr Leu Gln Tyr Gly Ala Gln Pro
            20                  25                  30

Leu Ile Ser Lys Arg Cys Ile Arg Lys Asp Val Ile Val Thr Ser Ser
        35                  40                  45

Val Leu Thr Cys Glu Ile Val Lys Val Ile Cys Ala Leu Ile Leu Met
    50                  55                  60

Ala Arg Asn Gly Ser Leu Lys Gly Leu Ala Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Ile Leu Gln Ile Gly Ala Leu Cys
    130                 135                 140

Leu Leu Ile Met Ala Ala Val Leu Leu Ser Val Gly Glu Gly Ser Asn
145                 150                 155                 160

Lys Asp Ser Ser Gly Ile Asn Ala Asp Gln Lys Leu Phe Tyr Gly Ile
                165                 170                 175

Ile Pro Val Leu Ala Ala Ser Val Leu Ser Gly Leu Ala Ser Ser Leu
            180                 185                 190

Cys Gln Trp Ala Ser Gln Val Lys Lys His Ser Ser Tyr Leu Met Thr
        195                 200                 205

Val Glu Met Ser Ile Val Gly Ser Leu Cys Leu Leu Val Ser Thr Leu
    210                 215                 220

Lys Ser Pro Asp Gly Glu Ala Ile Lys Lys Tyr Gly Phe Phe His Gly
225                 230                 235                 240

Trp Thr Ala Leu Thr Leu Val Ile Asn Tyr Leu Phe Phe Leu Ser Thr
                245                 250                 255

Lys Gln Phe Phe
            260

<210> SEQ ID NO 3
<211> LENGTH: 9
<212> TYPE: PRT
<213> ORGANISM: artificial
<220> FEATURE:
<223> OTHER INFORMATION: amino acid motif conserved in ROCK1 protein

<400> SEQUENCE: 3
```

Gly Gly Ile Leu Val Gly Leu Val Thr
1               5

<210> SEQ ID NO 4
<211> LENGTH: 2434
<212> TYPE: DNA
<213> ORGANISM: Arabidopsis thaliana

<400> SEQUENCE: 4

| | | | | | |
|---|---|---|---|---|---|
| gttcttcaaa | gcacaaacca | attctcgacc | aaaagatcag | aacaaagcga | aggcggattt | 60 |
| tctggattct | cgacggccgg | agattcatgg | cgacggctaa | cggagcaaag | agtccgtcga | 120 |
| gtatgggccc | taaggttttg | ttttattcca | tattgctcac | acttcagtac | ggagcccagc | 180 |
| ctctgatctc | caaacgctgc | atcaggtacg | gtctcttgca | caacctatg | cctcttaaat | 240 |
| ctctgatgtt | agtgatagcc | ttgttcatat | tcgctgattt | cgtgcgcttt | tatcgggaat | 300 |
| tgcgagattt | ggttgtaatt | agtcttatgt | agcgagtaga | gatggagttc | gatttctggg | 360 |
| catctgtttt | gttggctttc | tgcgaattgt | ggttgagaat | agtgttgtaa | acttacaatt | 420 |
| tcgaagttat | atgcgacgat | tgtgatgtat | tctcgttgtt | cctgtggaaa | agacatggt | 480 |
| cactgttaaa | ctaagccatt | ttctaaagtg | ttagagagat | gaatttgaat | ctactagttt | 540 |
| gctacattga | tgccttgaat | atagcttttc | atcatagtgt | tttagttgtt | catcttggtt | 600 |
| ttgtagggta | ccgtgtaacc | tttcgcgtta | tctagtactc | gatatcgagt | cactttgcct | 660 |
| aattttgcgg | caaaatgcca | tggatattta | gaactagtag | acttgtgttc | actagtccat | 720 |
| ttgtttgttt | cttcttaaac | agttaataga | ttgtctctat | catggtttgg | tcactttacc | 780 |
| gcattattgt | ttttgcagaa | aggatgttat | tgtaacttca | tctgttttga | cgtgcgagat | 840 |
| tgttaaggta | ctggatcttt | ttttttcctt | tctactttcg | aaaattttgc | atttatgaaa | 900 |
| tactgtttca | tgcttctgct | gtatgttctt | ttttataggt | catatgtgct | ctgattctca | 960 |
| tggcaagaaa | tggtagtttg | aagggattag | caaaagagtg | gacgttgatg | ggatccttga | 1020 |
| cagcatcagg | acttcctgca | gccatatatg | cactgcagaa | cagtttgctg | cagatctcat | 1080 |
| acaggagtct | tgattccttg | acattttcaa | ttctgaatca | gacgaaaatc | ttttcacag | 1140 |
| cattctttac | tttcataata | ctaaggtaac | ctttatttt | cttgttctta | tggtcttgtt | 1200 |
| tttgatagga | tgcttgaaat | tttgagtttg | ttggatttgt | attttcctca | gcgagtgcct | 1260 |
| acatcacatt | tttgaattag | agatttgtag | tgtgattgcc | tgaataactt | tatttgggct | 1320 |
| gcttctctgc | tccaacgtga | tacctaccat | gtcttaatag | tgtgattgcc | tgaatatcta | 1380 |
| ttgcttgaaa | agtgtttaac | acatcatctc | gaatgacatc | ttgtaggcag | aagcaatcaa | 1440 |
| ttctacaaat | aggagccttg | tgtctattga | tcatggcagc | agtccttcta | agtgttggtg | 1500 |
| aaggctctaa | caaagattca | agcggcatta | atgcggatca | aaagctgttt | tatggaatta | 1560 |
| tcccggtctt | ggcagcctct | gtcctgtcgg | gtttagcctc | ttctctgtgt | caatgggctt | 1620 |
| ctcaggtcat | ccagagttta | catatcatat | tccaataaaa | aatctgtact | tcaattcatt | 1680 |
| cgtagcctaa | actgtcttac | cgtttacagg | tcaagaagca | ttcatcatac | ttaatgacgg | 1740 |
| ttgaaatgtc | tatcgttgga | agcctctgtt | tattagtaag | tactcttaaa | tctccagatg | 1800 |
| gtgaagcgat | taaaaaatat | ggcttctttc | atggttggac | tgctttaaca | ctggtaataa | 1860 |
| actatctctt | ttttttatcc | acaaaacaat | tcttttgata | gcaaaacagt | gaattctgat | 1920 |
| tgtttgtatg | cactgtgact | gttgttatag | gtcccagtaa | taagcaatgc | tcttggtggg | 1980 |
| attcttgttg | gcctagttac | atcacatgcc | ggtggtgtaa | gaaaggtaaa | acaaaaaaaa | 2040 |

| | |
|---|---|
| accctcccag actgatatta cacaatcaaa agctgaaata tgtaatgtcg ttatatcact | 2100 |
| ttgcagggat ttgtgattgt gtcggcatta cttgtgacgg cgctacttca atttgcgttt | 2160 |
| gaaggaaaac cgccatcatc gtattgccta gttgctcttc ctcttgtgat gagtagtatc | 2220 |
| tcaatgtacc agaaataccc atacattgac aagaagaaga agaaggtgta agaaaaaggt | 2280 |
| tccattcaga gaatagctgc tagttacaac aatgagatat cttaatgcca ttattattaa | 2340 |
| ctaagtagat gatagtgtga ttcttggagc attcaaaaga cttttgtagta tatttacatt | 2400 |
| caaagatgga atgagtccaa ttgagtttaa gtaa | 2434 |

<210> SEQ ID NO 5
<211> LENGTH: 978
<212> TYPE: DNA
<213> ORGANISM: Arabidopsis thaliana

<400> SEQUENCE: 5

| | |
|---|---|
| atggcgacgg ctaacggagc aaagagtccg tcgagtatgg gccctaaggt tttgttttat | 60 |
| tccatattgc tcacacttca gtacggagcc cagcctctga tctccaaacg ctgcatcaga | 120 |
| aaggatgtta ttgtaacttc atctgttttg acgtgcgaga ttgttaaggt catatgtgct | 180 |
| ctgattctca tggcaagaaa tggtagtttg aagggattag caaaagagtg gacgttgatg | 240 |
| ggatccttga cagcatcagg acttcctgca gccatatatg cactgcagaa cagtttgctg | 300 |
| cagatctcat acaggagtct tgattccttg acattttcaa ttctgaatca gacgaaaatc | 360 |
| tttttcacag cattctttac tttcataata ctaaggcaga agcaatcaat tctacaaata | 420 |
| ggagccttgt gtctattgat catggcagca gtccttctaa gtgttggtga aggctctaac | 480 |
| aaagattcaa gcggcattaa tgcggatcaa aagctgtttt atggaattat cccggtcttg | 540 |
| gcagcctctg tcctgtcggg tttagcctct tctctgtgtc aatgggcttc tcaggtcaag | 600 |
| aagcattcat catacttaat gacggttgaa atgtctatcg ttggaagcct ctgtttatta | 660 |
| gtaagtactc ttaaatctcc agatggtgaa gcgattaaaa aatatggctt ctttcatggt | 720 |
| tggactgctt taacactggt cccagtaata agcaatgctc ttggtgggat tcttgttggc | 780 |
| ctagttacat cacatgccgg tggtgtaaga aagggattttg tgattgtgtc ggcattactt | 840 |
| gtgacggcgc tacttcaatt tgcgtttgaa ggaaaaccgc catcatcgta ttgcctagtt | 900 |
| gctcttcctc ttgtgatgag tagtatctca atgtaccaga aatacccata cattgacaag | 960 |
| aagaagaaga aggtgtaa | 978 |

<210> SEQ ID NO 6
<211> LENGTH: 783
<212> TYPE: DNA
<213> ORGANISM: Arabidopsis thaliana

<400> SEQUENCE: 6

| | |
|---|---|
| atggcgacgg ctaacggagc aaagagtccg tcgagtatgg gccctaaggt tttgttttat | 60 |
| tccatattgc tcacacttca gtacggagcc cagcctctga tctccaaacg ctgcatcaga | 120 |
| aaggatgtta ttgtaacttc atctgttttg acgtgcgaga ttgttaaggt catatgtgct | 180 |
| ctgattctca tggcaagaaa tggtagtttg aagggattag caaaagagtg gacgttgatg | 240 |
| ggatccttga cagcatcagg acttcctgca gccatatatg cactgcagaa cagtttgctg | 300 |
| cagatctcat acaggagtct tgattccttg acattttcaa ttctgaatca gacgaaaatc | 360 |
| tttttcacag cattctttac tttcataata ctaaggcaga agcaatcaat tctacaaata | 420 |
| ggagccttgt gtctattgat catggcagca gtccttctaa gtgttggtga aggctctaac | 480 |

```
aaagattcaa gcggcattaa tgcggatcaa aagctgtttt atggaattat cccggtcttg      540
gcagcctctg tcctgtcggg tttagcctct tctctgtgtc aatgggcttc tcaggtcaag      600
aagcattcat catacttaat gacggttgaa atgtctatcg ttggaagcct ctgtttatta      660
gtaagtactc ttaaatctcc agatggtgaa gcgattaaaa aatatggctt ctttcatggt      720
tggactgctt taacactggt aataaactat ctcttttttt tatccacaaa acaattcttt      780
tga                                                                   783
```

<210> SEQ ID NO 7
<211> LENGTH: 1227
<212> TYPE: DNA
<213> ORGANISM: Arabidopsis thaliana

<400> SEQUENCE: 7

```
gttcttcaaa gcacaaacca attctcgacc aaaagatcag aacaaagcga aggcggattt       60
tctggattct cgacggccgg agattcatgg cgacggctaa cggagcaaag agtccgtcga      120
gtatgggccc taaggttttg ttttattcca tattgctcac acttcagtac ggagcccagc      180
ctctgatctc caaacgctgc atcagaaagg atgttattgt aacttcatct gttttgacgt      240
gcgagattgt taaggtcata tgtgctctga ttctcatggc aagaaatggt agtttgaagg      300
gattagcaaa agagtggacg ttgatgggat ccttgacagc atcaggactt cctgcagcca      360
tatatgcact gcagaacagt ttgctgcaga tctcatacag gagtcttgat tccttgacat      420
tttcaattct gaatcagacg aaaatctttt tcacagcatt ctttactttc ataatactaa      480
ggcagaagca atcaattcta caaataggag ccttgtgtct attgatcatg gcagcagtcc      540
ttctaagtgt tggtgaaggc tctaacaaag attcaagcgg cattaatgcg gatcaaaagc      600
tgttttatgg aattatcccg gtcttggcag cctctgtcct gtcgggttta gcctcttctc      660
tgtgtcaatg ggcttctcag gtcaagaagc attcatcata cttaatgacg gttgaaatgt      720
ctatcgttgg aagcctctgt ttattagtaa gtactcttaa atctccagat ggtgaagcga      780
ttaaaaaata tggcttcttt catggttgga ctgctttaac actggtccca gtaataagca      840
atgctcttgg tgggattctt gttggcctag ttacatcaca tgccggtggt gtaagaaagg      900
gatttgtgat tgtgtcggca ttacttgtga cggcgctact tcaatttgcg tttgaaggaa      960
aaccgccatc atcgtattgc ctagttgctc ttcctcttgt gatgagtagt atctcaatgt     1020
accagaaata cccatacatt gacaagaaga agaagaaggt gtaagaaaaa ggttccattc     1080
agagaatagc tgctagttac aacaatgaga tatcttaatg ccattattat taactaagta     1140
gatgatagtg tgattcttgg agcattcaaa agactttgta gtatatttac attcaaagat     1200
ggaatgagtc caattgagtt taagtaa                                         1227
```

<210> SEQ ID NO 8
<211> LENGTH: 1324
<212> TYPE: DNA
<213> ORGANISM: Arabidopsis thaliana

<400> SEQUENCE: 8

```
gttcttcaaa gcacaaacca attctcgacc aaaagatcag aacaaagcga aggcggattt       60
tctggattct cgacggccgg agattcatgg cgacggctaa cggagcaaag agtccgtcga      120
gtatgggccc taaggttttg ttttattcca tattgctcac acttcagtac ggagcccagc      180
ctctgatctc caaacgctgc atcagaaagg atgttattgt aacttcatct gttttgacgt      240
```

```
gcgagattgt taaggtcata tgtgctctga ttctcatggc aagaaatggt agtttgaagg    300
gattagcaaa agagtggacg ttgatgggat ccttgacagc atcaggactt cctgcagcca    360
tatatgcact gcagaacagt ttgctgcaga tctcatacag gagtcttgat tccttgacat    420
tttcaattct gaatcagacg aaaatctttt tcacagcatt ctttactttc ataatactaa    480
ggcagaagca atcaattcta caaataggag ccttgtgtct attgatcatg gcagcagtcc    540
ttctaagtgt tggtgaaggc tctaacaaag attcaagcgg cattaatgcg gatcaaaagc    600
tgttttatgg aattatcccg gtcttggcag cctctgtcct gtcgggttta gcctcttctc    660
tgtgtcaatg ggcttctcag gtcaagaagc attcatcata cttaatgacg gttgaaatgt    720
ctatcgttgg aagcctctgt ttattagtaa gtactcttaa atctccagat ggtgaagcga    780
ttaaaaaata tggcttcttt catggttgga ctgctttaac actggtaata aactatctct    840 ttttttatc cacaaaacaa ttcttttgat agcaaaacag tgaattctga ttgtttgtat    900
gcactgtgac tgttgttata ggtcccagta ataagcaatg ctcttggtgg gattcttgtt    960
ggcctagtta catcacatgc cggtggtgta agaaagggat tgtgattgt gtcggcatta   1020 cttgtgacgg cgctacttca atttgcgttt gaaggaaaac cgccatcatc gtattgccta   1080
gttgctcttc ctcttgtgat gagtagtatc tcaatgtacc agaaatacc atacattgac    1140 aagaagaaga agaaggtgta agaaaaaggt tccattcaga gaatagctgc tagttacaac   1200
aatgagatat cttaatgcca ttattattaa ctaagtagat gatagtgtga ttcttggagc   1260
attcaaaaga ctttgtagta tatttacatt caaagatgga atgagtccaa ttgagtttaa   1320
gtaa                                                                1324
```

<210> SEQ ID NO 9
<211> LENGTH: 326
<212> TYPE: PRT
<213> ORGANISM: Brassica napus

<400> SEQUENCE: 9

```
Met Ala Thr Ala Asn Gly Ala Lys Gly Pro Ser Arg Met Gly Pro Lys
1               5                   10                  15

Val Leu Phe Tyr Ser Ile Leu Thr Leu Gln Tyr Gly Ala Gln Pro
            20                  25                  30

Leu Ile Ser Lys Arg Cys Ile Gly Lys Glu Val Ile Val Thr Ser Ser
        35                  40                  45

Val Leu Thr Cys Glu Val Val Lys Val Ile Cys Ala Leu Ile Leu Met
    50                  55                  60

Ala Arg Asp Gly Ser Leu Lys Lys Leu Ala Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Thr Phe
        115                 120                 125

Ile Ile Leu Arg Gln Lys Gln Ser Val Gln Gln Ile Gly Ala Leu Cys
    130                 135                 140

Leu Leu Ile Met Ala Ala Val Leu Leu Ser Val Gly Glu Gly Ser Asn
145                 150                 155                 160

Lys Ser Ser Ser Gly Gly Val Asn Pro Glu His Val Leu Phe Tyr Gly
                165                 170                 175
```

```
Ile Ile Pro Val Leu Leu Ala Ser Val Leu Ser Gly Leu Ala Ser Ser
            180                 185                 190

Leu Cys Gln Trp Ala Ser Gln Val Lys Lys His Ser Ser Tyr Leu Met
        195                 200                 205

Thr Leu Glu Met Ser Ile Val Gly Ser Leu Cys Leu Val Ser Thr
    210                 215                 220

Leu Lys Ser Pro Asp Gly Glu Ala Ile Lys Arg His Gly Phe Phe His
225                 230                 235                 240

Gly Trp Thr Ala Leu Thr Met Val Pro Val Ile Ser Asn Ala Leu Gly
                245                 250                 255

Gly Ile Leu Val Gly Leu Val Thr Ser His Ala Gly Val Arg Lys
            260                 265                 270

Gly Phe Val Ile Val Ser Ala Leu Leu Val Thr Ala Leu Leu Gln Phe
                275                 280                 285

Ala Phe Glu Gly Lys Pro Pro Ser Ser Tyr Cys Leu Val Ala Leu Pro
        290                 295                 300

Leu Val Ile Ser Ser Ile Ser Leu Tyr Gln Lys Tyr Pro Tyr Met Asp
305                 310                 315                 320

Lys Lys Lys Lys Lys Val
                325

<210> SEQ ID NO 10
<211> LENGTH: 326
<212> TYPE: PRT
<213> ORGANISM: Brassica napus

<400> SEQUENCE: 10

Met Ala Thr Pro Asn Gly Val Lys Ser Gln Ser Arg Met Gly Pro Lys
1               5                   10                  15

Val Leu Phe Tyr Ser Ile Leu Leu Thr Leu Gln Tyr Gly Ala Gln Pro
            20                  25                  30

Leu Ile Ser Lys Arg Cys Ile Gly Arg Glu Val Ile Val Thr Ser Ser
        35                  40                  45

Val Leu Thr Cys Glu Ile Val Lys Val Ile Cys Ala Leu Ile Leu Met
    50                  55                  60

Ala Arg Asp Gly Ser Leu Lys Gly Leu Ser Lys Glu Trp Thr Leu Met
65              70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Val Gln Gln Met Gly Ala Leu Cys
    130                 135                 140

Leu Leu Ile Met Ala Ala Val Leu Leu Ser Val Gly Glu Gly Ser Asn
145                 150                 155                 160

Lys Ser Ser Ser Asp Gly Val Asn Pro Glu Gln Val Leu Phe Tyr Gly
                165                 170                 175

Ile Ile Pro Val Leu Val Ala Ser Val Leu Ser Gly Leu Ala Ser Ser
            180                 185                 190

Leu Cys Gln Trp Ala Ser Gln Val Lys Lys His Ser Ser Tyr Leu Met
        195                 200                 205

Thr Val Glu Met Ser Ile Val Gly Ser Leu Cys Leu Leu Val Ser Thr
    210                 215                 220
```

```
Leu Lys Ser Pro Asp Gly Glu Ala Ile Lys Arg His Gly Phe Phe His
225                 230                 235                 240

Gly Trp Thr Ala Leu Thr Met Val Pro Val Ile Ser Asn Ala Leu Gly
                245                 250                 255

Gly Ile Leu Val Gly Leu Val Thr Ser His Ala Gly Gly Val Arg Lys
            260                 265                 270

Gly Phe Val Ile Val Ser Ala Leu Leu Val Thr Ala Leu Leu Gln Phe
        275                 280                 285

Ala Phe Glu Gly Lys Pro Pro Ser Ser Tyr Cys Leu Val Ala Leu Pro
    290                 295                 300

Leu Val Ile Ser Ser Ile Ser Leu Tyr Gln Lys Tyr Pro Tyr Leu Asp
305                 310                 315                 320

Lys Lys Lys Lys Lys Val
                325
```

<210> SEQ ID NO 11
<211> LENGTH: 326
<212> TYPE: PRT
<213> ORGANISM: Brassica napus

<400> SEQUENCE: 11

```
Met Ala Ala Ser Asn Gly Ala Lys Ser Ala Ser Lys Met Gly Pro Lys
1               5                   10                  15

Val Leu Phe Tyr Ser Leu Leu Leu Thr Leu Gln Tyr Gly Ala Gln Pro
                20                  25                  30

Leu Ile Ser Lys Arg Cys Ile Gly Lys Glu Val Ile Val Thr Ser Ser
            35                  40                  45

Val Leu Thr Cys Glu Ile Val Lys Val Val Cys Ala Leu Ile Leu Met
    50                  55                  60

Ala Arg Asp Gly Ser Leu Lys Gly Leu Ala Lys Glu Trp Thr Leu Met
65              70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
    115                 120                 125

Ile Ile Leu Arg Gln Lys Gln Ser Val Gln Gln Ile Gly Ala Leu Cys
130                 135                 140

Leu Leu Ile Met Ala Ala Val Leu Leu Ser Val Gly Glu Gly Ser Asn
145                 150                 155                 160

Lys Thr Ser Ser Ser Gly Ile Asn Pro Glu Gln Val Leu Phe Ser Gly
                165                 170                 175

Ile Ile Pro Val Leu Val Ala Ser Val Leu Ser Gly Leu Ala Ser Ser
            180                 185                 190

Leu Cys Gln Trp Ala Ser Gln Val Lys Lys His Ser Ser Tyr Leu Met
    195                 200                 205

Thr Val Glu Met Ser Ile Val Gly Ser Leu Cys Met Leu Ala Ser Thr
210                 215                 220

Leu Lys Ser Pro Asp Gly Glu Ala Ile Lys Arg His Gly Phe Phe His
225                 230                 235                 240

Gly Trp Thr Ala Leu Thr Leu Val Pro Val Ile Ser Asn Ala Leu Gly
                245                 250                 255

Gly Ile Leu Val Gly Leu Val Thr Ser His Ala Gly Gly Val Arg Lys
```

```
                 260                 265                 270
Gly Phe Val Ile Val Ser Ala Leu Leu Val Thr Ala Leu Leu Gln Phe
            275                 280                 285
Ala Phe Glu Gly Lys Pro Pro Ser Ser Tyr Cys Leu Val Ser Leu Pro
        290                 295                 300
Leu Val Ile Ser Ser Ile Ser Leu Tyr Gln Lys Tyr Pro Tyr Leu Asp
305                 310                 315                 320
Lys Lys Lys Lys Lys Val
                325

<210> SEQ ID NO 12
<211> LENGTH: 323
<212> TYPE: PRT
<213> ORGANISM: Brassica napus

<400> SEQUENCE: 12

Met Ala Ala Ser Asn Gly Ala Lys Ser Pro Ser Lys Met Val Leu Phe
1               5                   10                  15
Tyr Ser Leu Leu Leu Thr Leu Gln Tyr Gly Ala Gln Pro Leu Ile Ser
                20                  25                  30
Lys Arg Cys Ile Gly Lys Glu Val Ile Val Thr Ser Ser Val Leu Thr
            35                  40                  45
Cys Glu Ile Val Lys Val Ile Cys Ala Leu Val Leu Met Ala Arg Asp
        50                  55                  60
Gly Ser Leu Lys Gly Leu Ala Lys Glu Trp Thr Leu Met Gly Ser Leu
65                  70                  75                  80
Thr Ala Ser Gly Leu Pro Ala Ala Ile Tyr Ala Leu Gln Asn Ser Leu
                85                  90                  95
Leu Gln Ile Ser Tyr Arg Ser Leu Asp Ser Leu Thr Phe Ser Ile Leu
            100                 105                 110
Asn Gln Thr Lys Ile Phe Phe Thr Ala Phe Phe Thr Phe Ile Ile Leu
        115                 120                 125
Arg Gln Lys Gln Ser Val Gln Gln Ile Gly Ala Leu Cys Leu Leu Ile
130                 135                 140
Met Ala Ala Val Leu Leu Ser Val Gly Glu Gly Ser Asn Lys Thr Ser
145                 150                 155                 160
Ser Ser Gly Ile Asn Pro Glu Gln Val Leu Phe Ser Gly Ile Ile Pro
                165                 170                 175
Val Leu Val Ala Ser Val Leu Ser Gly Leu Ala Ser Ser Leu Cys Gln
            180                 185                 190
Trp Ala Ser Gln Val Lys Lys His Ser Ser Tyr Leu Met Thr Val Glu
        195                 200                 205
Met Ser Ile Val Gly Ser Leu Cys Met Leu Ala Ser Thr Leu Lys Ser
210                 215                 220
Pro Asp Gly Glu Ala Ile Lys Arg His Gly Phe Phe His Gly Trp Thr
225                 230                 235                 240
Ala Leu Thr Met Val Pro Val Ile Ser Asn Ala Leu Gly Gly Ile Leu
                245                 250                 255
Val Gly Leu Val Thr Ser His Ala Gly Gly Val Arg Lys Gly Phe Val
            260                 265                 270
Ile Val Ser Ala Leu Leu Val Thr Ala Leu Leu Gln Phe Ala Phe Glu
        275                 280                 285
Gly Lys Pro Pro Ser Ser Tyr Cys Leu Val Ala Leu Pro Leu Val Ile
        290                 295                 300
```

```
Ser Ser Ile Ser Leu Tyr Gln Lys Tyr Pro Tyr Leu Asp Lys Lys
305                 310                 315                 320

Lys Lys Val

<210> SEQ ID NO 13
<211> LENGTH: 326
<212> TYPE: PRT
<213> ORGANISM: Brassica oleracea

<400> SEQUENCE: 13

Met Ala Ala Ser Asn Gly Ala Lys Ser Pro Ser Lys Met Gly Pro Lys
1               5                   10                  15

Val Leu Phe Tyr Ser Leu Leu Thr Leu Gln Tyr Gly Ala Gln Pro
            20                  25                  30

Leu Ile Ser Lys Arg Cys Ile Gly Lys Glu Val Ile Val Thr Ser Ser
                35                  40                  45

Val Leu Thr Cys Glu Ile Val Lys Val Val Cys Ala Leu Ile Leu Met
        50                  55                  60

Ala Arg Asp Gly Ser Leu Lys Gly Leu Ala Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Val Gln Gln Ile Gly Ala Leu Cys
130                 135                 140

Leu Leu Ile Met Ala Ala Val Leu Leu Ser Val Gly Glu Gly Ser Asn
145                 150                 155                 160

Lys Thr Ser Ser Gly Ile Asn Pro Glu Gln Val Leu Phe Ser Gly
                165                 170                 175

Ile Ile Pro Val Leu Val Ala Ser Val Leu Ser Gly Leu Ala Ser Ser
            180                 185                 190

Leu Cys Gln Trp Ala Ser Gln Val Lys Lys His Ser Tyr Leu Met
        195                 200                 205

Thr Val Glu Met Ser Ile Val Gly Ser Leu Cys Met Leu Ala Ser Thr
210                 215                 220

Leu Lys Ser Pro Asp Gly Glu Ala Ile Lys Arg His Gly Phe Phe His
225                 230                 235                 240

Gly Trp Thr Ala Leu Thr Leu Val Pro Val Ile Ser Asn Ala Leu Gly
                245                 250                 255

Gly Ile Leu Val Gly Leu Val Thr Ser His Ala Gly Val Arg Lys
            260                 265                 270

Gly Phe Val Ile Val Ser Ala Leu Leu Val Thr Ala Leu Leu Gln Phe
        275                 280                 285

Ala Phe Glu Gly Lys Pro Pro Ser Ser Tyr Cys Leu Val Ala Leu Pro
290                 295                 300

Leu Val Ile Ser Ser Ile Ser Leu Tyr Gln Lys Tyr Pro Tyr Leu Asp
305                 310                 315                 320

Lys Lys Lys Lys Lys Val
                325

<210> SEQ ID NO 14
<211> LENGTH: 326
```

```
<212> TYPE: PRT
<213> ORGANISM: Brassica oleracea

<400> SEQUENCE: 14

Met Ala Thr Ala Asn Gly Ala Lys Gly Pro Ser Arg Met Gly Pro Lys
1               5                   10                  15

Val Leu Phe Tyr Ser Ile Leu Leu Thr Leu Gln Tyr Gly Ala Gln Pro
            20                  25                  30

Leu Ile Ser Lys Arg Cys Ile Gly Lys Glu Val Ile Val Thr Ser Ser
        35                  40                  45

Val Leu Thr Cys Glu Val Val Lys Val Ile Cys Ala Leu Ile Leu Met
    50                  55                  60

Ala Arg Asp Gly Ser Leu Lys Lys Leu Ala Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Val Gln Gln Ile Gly Ala Leu Cys
    130                 135                 140

Leu Leu Ile Met Ala Ala Val Leu Leu Ser Val Gly Glu Gly Ser Asn
145                 150                 155                 160

Lys Ser Ser Ser Gly Gly Val Asn Pro Glu His Val Leu Phe Tyr Gly
                165                 170                 175

Ile Ile Pro Val Leu Leu Ala Ser Val Leu Ser Gly Leu Ala Ser Ser
            180                 185                 190

Leu Cys Gln Trp Ala Ser Gln Val Lys Lys His Ser Ser Tyr Leu Met
        195                 200                 205

Thr Leu Glu Met Ser Ile Val Gly Ser Leu Cys Leu Leu Val Ser Thr
    210                 215                 220

Leu Lys Ser Pro Asp Gly Glu Ala Ile Lys Arg His Gly Phe Phe His
225                 230                 235                 240

Gly Trp Thr Ala Leu Thr Met Val Pro Val Ile Ser Asn Ala Leu Gly
                245                 250                 255

Gly Ile Leu Val Gly Leu Val Thr Ser His Ala Gly Val Arg Lys
            260                 265                 270

Gly Phe Val Ile Val Ser Ala Leu Leu Val Thr Ala Leu Leu Gln Phe
        275                 280                 285

Ala Phe Glu Gly Lys Pro Pro Ser Ser Tyr Cys Leu Val Ala Leu Pro
    290                 295                 300

Leu Val Ile Ser Ser Ile Ser Leu Tyr Gln Lys Tyr Pro Tyr Met Asp
305                 310                 315                 320

Lys Lys Lys Lys Lys Val
                325

<210> SEQ ID NO 15
<211> LENGTH: 325
<212> TYPE: PRT
<213> ORGANISM: Brassica rapa

<400> SEQUENCE: 15

Met Ala Thr Pro Asn Gly Val Lys Ser Gln Ser Arg Met Gly Pro Thr
1               5                   10                  15
```

-continued

Val Leu Phe Tyr Ser Ile Leu Leu Thr Leu Gln Tyr Gly Ala Gln Pro
            20                  25                  30

Leu Ile Ser Lys Arg Cys Ile Gly Lys Glu Val Ile Val Thr Ser Ser
        35                  40                  45

Val Leu Thr Cys Glu Ile Val Lys Val Ile Cys Ala Leu Ile Leu Met
    50                  55                  60

Ala Arg Asp Gly Ser Leu Lys Gly Leu Ser Lys Glu Trp Thr Leu Met
65                  70                  75                  80

Gly Ser Leu Thr Ala Ser Gly Leu Pro Ala Ala Ile Tyr Ala Leu Gln
                85                  90                  95

Asn Ser Leu Leu Gln Ile Ser Tyr Arg Ser Leu Asp Ser Leu Thr Phe
            100                 105                 110

Ser Ile Leu Asn Gln Thr Lys Ile Phe Phe Thr Ala Phe Phe Thr Phe
        115                 120                 125

Ile Ile Leu Arg Gln Lys Gln Ser Val Gln Gln Met Gly Ala Leu Cys
    130                 135                 140

Leu Leu Ile Met Ala Ala Val Leu Leu Ser Val Gly Glu Gly Ser Asn
145                 150                 155                 160

Lys Ser Ser Ser Gly Gly Val Asn Pro Glu Gln Val Leu Phe Tyr Gly
                165                 170                 175

Ile Ile Pro Val Leu Val Ala Ser Val Leu Ser Gly Leu Ala Ser Ser
            180                 185                 190

Leu Cys Gln Trp Ala Ser Gln Val Lys Lys His Ser Ser Tyr Leu Met
        195                 200                 205

Thr Val Glu Met Ser Ile Val Gly Ser Leu Cys Leu Leu Val Ser Thr
    210                 215                 220

Leu Lys Ser Pro Asp Gly Glu Ala Ile Lys Arg His Gly Phe Phe His
225                 230                 235                 240

Gly Trp Thr Ala Leu Thr Met Val Pro Val Ile Ser Asn Ala Leu Gly
                245                 250                 255

Gly Ile Leu Val Gly Leu Val Thr Ser His Ala Gly Val Arg Lys
            260                 265                 270

Gly Phe Val Ile Val Ser Ala Leu Leu Val Thr Ala Leu Leu Gln Phe
        275                 280                 285

Ala Phe Glu Gly Lys Pro Pro Ser Ser Tyr Cys Leu Val Ala Leu Pro
    290                 295                 300

Leu Val Ile Ser Ser Ile Ser Gln Tyr Gln Lys Tyr Pro Tyr Met Asp
305                 310                 315                 320

Lys Lys Lys Lys Val
                325

<210> SEQ ID NO 16
<211> LENGTH: 322
<212> TYPE: PRT
<213> ORGANISM: Brassica rapa

<400> SEQUENCE: 16

Met Ala Ala Ser Asn Gly Ala Lys Ser Pro Ser Lys Lys Val Leu Phe
1               5                   10                  15

Tyr Ser Leu Leu Leu Thr Leu Gln Tyr Gly Ala Gln Pro Leu Ile Ser
            20                  25                  30

Lys Arg Cys Ile Gly Lys Glu Val Ile Val Thr Ser Ser Val Leu Thr
        35                  40                  45

Cys Glu Ile Val Lys Val Val Cys Ala Leu Ile Leu Met Ala Arg Asp
    50                  55                  60

Gly Ser Leu Lys Gly Leu Ala Lys Glu Trp Thr Leu Met Gly Ser Leu
65                  70                  75                  80

Thr Ala Ser Gly Leu Pro Ala Ala Ile Tyr Ala Leu Gln Asn Ser Leu
                85                  90                  95

Leu Gln Ile Ser Tyr Arg Ser Leu Asp Ser Leu Thr Phe Ser Ile Leu
            100                 105                 110

Asn Gln Thr Lys Ile Phe Phe Thr Ala Phe Phe Thr Phe Ile Ile Leu
        115                 120                 125

Arg Gln Lys Gln Ser Val Gln Gln Ile Gly Ala Leu Cys Leu Leu Ile
130                 135                 140

Met Ala Ala Val Leu Leu Ser Val Gly Glu Gly Ser Asn Lys Thr Ser
145                 150                 155                 160

Ser Ser Gly Ile Asn Pro Glu Gln Val Leu Phe Ser Gly Ile Ile Pro
                165                 170                 175

Val Leu Val Ala Ser Val Leu Ser Gly Leu Ala Ser Ser Leu Cys Gln
            180                 185                 190

Trp Ala Ser Gln Val Lys Lys His Ser Ser Tyr Leu Met Thr Val Glu
        195                 200                 205

Met Ser Ile Val Gly Ser Leu Cys Met Leu Ala Ser Thr Leu Lys Ser
210                 215                 220

Pro Asp Gly Glu Ala Ile Lys Arg His Gly Phe Phe His Gly Trp Thr
225                 230                 235                 240

Ala Leu Thr Met Val Pro Val Ile Ser Asn Ala Leu Gly Gly Ile Leu
                245                 250                 255

Val Gly Leu Val Thr Ser His Ala Gly Gly Val Arg Lys Gly Phe Val
            260                 265                 270

Ile Val Ser Ala Leu Leu Val Thr Ala Leu Leu Gln Phe Ala Phe Glu
        275                 280                 285

Gly Lys Pro Pro Ser Ser Tyr Cys Leu Val Ala Leu Pro Leu Val Ile
290                 295                 300

Ser Ser Ile Ser Leu Tyr Gln Lys Tyr Pro Tyr Leu Asp Lys Lys Lys
305                 310                 315                 320

Lys Lys

<210> SEQ ID NO 17
<211> LENGTH: 332
<212> TYPE: PRT
<213> ORGANISM: Fragaria vesca

<400> SEQUENCE: 17

Met Ala Thr Ala Thr Ala Ala Ala Lys Pro Lys Arg Pro Pro Pro
1               5                   10                  15

Thr Ser Asp Gln Met Asn Ala Lys Val Phe Leu Tyr Ser Val Leu Leu
            20                  25                  30

Ala Leu Gln Tyr Gly Ala Gln Pro Leu Ile Ser Lys Arg Phe Ile Arg
        35                  40                  45

Arg Glu Val Ile Val Thr Ser Ser Val Leu Thr Cys Glu Val Ala Lys
50                  55                  60

Val Ile Cys Ala Leu Val Phe Met Ala Arg Asp Gly Ser Leu Lys Lys
65                  70                  75                  80

Val Tyr Lys Glu Trp Thr Leu Leu Gly Ala Leu Thr Ala Ser Gly Leu
                85                  90                  95

Pro Ala Ala Ile Tyr Ala Leu Gln Asn Ser Leu Leu Gln Ile Ser Tyr
            100                 105                 110

Lys Asn Leu Asp Ser Leu Thr Phe Ser Met Leu Asn Gln Thr Lys Ile
            115                 120                 125

Ile Phe Thr Ala Met Cys Thr Tyr Leu Ile Leu Arg Gln Lys Gln Ser
        130                 135                 140

Ile Gln Gln Val Gly Ala Leu Phe Leu Ile Ile Ala Ala Val Leu
145                 150                 155                 160

Leu Ser Phe Gly Glu Gly Ser Ser Lys Arg Ser Ser Gly Gly Asn Ser
                165                 170                 175

Asp Gln Ile Trp Phe Asn Gly Ile Ile Pro Val Leu Val Ala Ser Val
        180                 185                 190

Leu Ser Gly Leu Ala Ser Ser Leu Cys Gln Trp Ala Ser Gln Val Lys
            195                 200                 205

Lys His Ser Ser Tyr Leu Met Thr Val Glu Met Ser Ile Val Gly Ser
    210                 215                 220

Leu Cys Met Leu Ala Ser Thr Ala Lys Ser Pro Asp Gly Glu Ala Ile
225                 230                 235                 240

Arg Lys His Gly Leu Phe Tyr Gly Trp Thr Ile Leu Thr Trp Ile Pro
                245                 250                 255

Val Met Ser Asn Ala Leu Gly Gly Ile Leu Val Gly Leu Val Thr Thr
            260                 265                 270

His Ala Gly Gly Val Arg Lys Gly Phe Val Ile Val Ser Ala Leu Leu
        275                 280                 285

Val Thr Ala Leu Leu Gln Phe Ile Phe Glu Gly Lys Pro Pro Ser Leu
    290                 295                 300

Tyr Cys Leu Ala Ser Leu Pro Leu Val Val Ser Ile Ser Ile Tyr
305                 310                 315                 320

Gln Lys Tyr Pro Tyr Arg Val Lys Lys Lys Glu Ser
                325                 330

<210> SEQ ID NO 18
<211> LENGTH: 327
<212> TYPE: PRT
<213> ORGANISM: Prunus persica

<400> SEQUENCE: 18

Met Ala Ala Thr Lys His Lys Ala Pro Val Arg Ser Ser Glu Lys Met
1               5                   10                  15

Asn Ser Arg Val Trp Leu Phe Ser Leu Leu Thr Leu Gln Tyr Gly
            20                  25                  30

Ala Gln Pro Leu Ile Ser Lys Arg Cys Thr Arg Glu Val Ile Val
        35                  40                  45

Thr Ser Ser Val Leu Thr Cys Glu Ile Ala Lys Val Val Cys Ala Leu
50                  55                  60

Ile Phe Met Ala Arg Asp Gly Ser Leu Lys Lys Val Tyr Lys Glu Trp
65                  70                  75                  80

Thr Leu Val Gly Ala Leu Thr Ala Ser Gly Leu Pro Ala Ala Ile Tyr
                85                  90                  95

Ala Leu Gln Asn Ser Leu Leu Gln Ile Ser Tyr Lys Asn Leu Asp Ser
            100                 105                 110

Leu Thr Phe Ser Met Leu Asn Gln Thr Lys Ile Ile Phe Thr Ala Leu
        115                 120                 125

Phe Thr Tyr Leu Ile Leu Arg Gln Lys Gln Ser Ile Gln Gln Ile Gly
    130                 135                 140

Ala Leu Phe Leu Leu Ile Leu Ala Ala Ile Leu Leu Ser Phe Gly Glu

```
145                 150                 155                 160
   Gly Ser Lys Lys Gly Ser Ser Ala Ser Asn Ser Asp Gln Ile Leu Phe
                   165                 170                 175

Asn Gly Ile Ile Pro Val Met Val Ala Ser Val Leu Ser Gly Leu Ala
                   180                 185                 190

Ser Thr Leu Cys Gln Trp Ala Ser Gln Val Lys Lys His Ser Ser Tyr
                   195                 200                 205

Leu Met Thr Val Glu Met Ser Ile Val Gly Ser Leu Cys Leu Leu Ala
                   210                 215                 220

Ser Thr Phe Lys Ser Pro Asp Gly Glu Ala Ile Ala Lys His Gly Leu
   225                 230                 235                 240

Phe Tyr Gly Trp Thr Leu Met Thr Trp Ile Pro Val Met Ser Asn Ala
                   245                 250                 255

Leu Gly Gly Ile Leu Val Gly Leu Val Thr Ser Tyr Ala Gly Gly Val
                   260                 265                 270

Lys Lys Gly Phe Val Ile Val Ser Ala Leu Leu Val Thr Ala Leu Leu
                   275                 280                 285

Gln Phe Ile Phe Glu Gly Lys Pro Pro Ser Leu Tyr Cys Leu Val Ala
                   290                 295                 300

Leu Pro Leu Val Val Ser Ser Ile Ser Ile Tyr Gln Lys Tyr Pro Tyr
   305                 310                 315                 320

Arg Val Lys Arg Lys Glu Leu
                   325

<210> SEQ ID NO 19
<211> LENGTH: 328
<212> TYPE: PRT
<213> ORGANISM: Malus domestica
<220> FEATURE:
<221> NAME/KEY: misc_feature
<222> LOCATION: (247)..(247)
<223> OTHER INFORMATION: Xaa can be any naturally occurring amino acid

<400> SEQUENCE: 19

Met Ala Ala Gly Lys Gln Lys Ala Pro Ala Pro Ser Ala Glu Lys
   1               5                   10                  15

Ile Asn Ser Arg Val Trp Phe Tyr Ser Leu Leu Thr Leu Gln Tyr
                   20                  25                  30

Gly Ala Gln Pro Leu Ile Ser Lys Arg Phe Thr Ser Arg Glu Val Ile
                   35                  40                  45

Val Thr Ser Ser Val Leu Thr Cys Glu Ile Ala Lys Ile Ile Cys Ala
   50                  55                  60

Leu Ile Phe Met Ala Arg Asp Gly Ser Leu Lys Lys Val Tyr Arg Glu
   65                  70                  75                  80

Trp Thr Leu Val Gly Ala Leu Thr Ala Ser Gly Leu Pro Ala Ala Ile
                   85                  90                  95

Tyr Ala Leu Gln Asn Ser Leu Leu Gln Ile Ser Tyr Lys Asn Leu Asp
                   100                 105                 110

Ser Leu Thr Phe Ser Met Leu Asn Gln Thr Lys Ile Ile Phe Thr Ala
                   115                 120                 125

Leu Phe Thr Tyr Leu Ile Leu Arg Gln Lys Gln Ser Ile Gln Gln Ile
                   130                 135                 140

Gly Ala Leu Val Leu Leu Ile Met Ala Ala Val Leu Leu Ser Phe Gly
   145                 150                 155                 160

Glu Gly Ser Lys Lys Gly Thr Ser Ser Gly Ser Ser Asp Gln Ile Leu
                   165                 170                 175
```

```
Phe Arg Gly Ile Ile Pro Val Leu Val Ala Ser Val Leu Ser Gly Leu
            180                 185                 190

Ala Ser Ser Leu Cys Gln Trp Ala Ser Gln Val Lys Lys His Ser Ser
            195                 200                 205

Tyr Leu Met Thr Val Glu Met Ser Val Val Gly Ser Leu Cys Leu Leu
            210                 215                 220

Ala Ser Thr Ser Lys Ser Pro Asp Gly Glu Ala Ile Arg Ile His Gly
225                 230                 235                 240

Phe Phe Tyr Gly Trp Thr Xaa Met Thr Trp Ile Pro Val Met Ser Asn
                245                 250                 255

Ala Leu Gly Gly Ile Leu Val Gly Leu Val Thr Ser Tyr Ala Gly Gly
            260                 265                 270

Val Lys Lys Gly Phe Val Ile Val Ser Ala Leu Leu Val Thr Ala Met
            275                 280                 285

Leu Gln Phe Ile Phe Glu Gly Lys Pro Pro Ser Leu Tyr Cys Leu Leu
            290                 295                 300

Ala Leu Pro Leu Val Ala Ser Ser Ile Ser Ile Tyr Gln Lys Tyr Pro
305                 310                 315                 320

Tyr Arg Val Lys Lys Lys Glu Ala
                325

<210> SEQ ID NO 20
<211> LENGTH: 326
<212> TYPE: PRT
<213> ORGANISM: Brachypodium distachyon

<400> SEQUENCE: 20

Met Gly Ser Val Ser Lys Pro Ser Pro Thr Ala Ala Ala Pro Ser Arg
1               5                   10                  15

Arg Arg Val Ala Leu Tyr Leu Ala Leu Leu Thr Leu Gln Tyr Gly Ala
            20                  25                  30

Gln Pro Leu Ile Ser Lys Arg Phe Val Arg Arg Glu Val Ile Val Thr
            35                  40                  45

Ser Leu Val Leu Ala Ile Glu Val Leu Lys Val Met Cys Ala Val Ile
        50                  55                  60

Leu Leu Val Ala Glu Gly Ser Leu Lys Lys Gln Phe Ser Asn Trp Asn
65              70                  75                  80

Leu Ala Gly Ser Leu Thr Ala Ser Gly Leu Pro Ala Ala Ile Tyr Ala
            85                  90                  95

Leu Gln Asn Ser Leu Leu Gln Ile Ser Tyr Lys Asn Leu Asp Ser Leu
            100                 105                 110

Thr Phe Ser Ile Leu Asn Gln Thr Lys Leu Leu Phe Thr Ala Phe Phe
            115                 120                 125

Thr Tyr Leu Ile Leu Gly Gln Arg Gln Ser Pro Lys Gln Ile Phe Ala
            130                 135                 140

Leu Thr Leu Leu Ile Ser Ala Ala Val Leu Leu Ser Val Gly Glu Ser
145                 150                 155                 160

Thr Thr Lys Gly Leu Asn Gly Gly Ser Ser Glu Tyr Val Leu Leu Tyr
                165                 170                 175

Gly Ile Ile Pro Val Thr Val Ala Ser Val Leu Ser Gly Leu Ala Ser
            180                 185                 190

Ser Leu Cys Gln Trp Ala Ser Gln Val Lys Lys His Ala Ser Tyr Leu
            195                 200                 205

Met Thr Ile Glu Met Ser Phe Ile Gly Ser Met Cys Leu Leu Ala Ser
```

```
            210                 215                 220
Thr Phe Gln Ser Pro Asp Gly Glu Ala Met Lys Lys Tyr Gly Phe Phe
225                 230                 235                 240

His Glu Trp Thr Ser Leu Thr Leu Ile Pro Val Leu Met Asn Ala Val
                245                 250                 255

Gly Gly Ile Leu Val Gly Leu Val Thr Thr Tyr Ala Gly Gly Val Arg
                260                 265                 270

Lys Gly Phe Val Ile Val Ser Ala Leu Leu Val Thr Ala Leu Leu Gln
                275                 280                 285

Phe Ile Phe Asp Gly Lys Pro Pro Ser Val Tyr Cys Leu Met Ala Leu
                290                 295                 300

Pro Leu Val Met Ala Ser Ile Phe Ile Tyr Gln Lys Tyr Pro Tyr Val
305                 310                 315                 320

Asp Arg Lys Lys Lys Asp
                325

<210> SEQ ID NO 21
<211> LENGTH: 327
<212> TYPE: PRT
<213> ORGANISM: sorghum bicolor

<400> SEQUENCE: 21

Met Gly Ser Ser Thr Pro Ala Ala Ala Ala Ala Ala Ala Ala Pro Ser
1               5                   10                  15

Arg Arg Lys Val Ala Leu Tyr Leu Ala Leu Leu Thr Leu Gln Tyr Gly
                20                  25                  30

Ala Gln Pro Leu Ile Ser Lys Arg Phe Val Arg Gln Asp Thr Ile Val
                35                  40                  45

Thr Ser Leu Val Leu Ala Thr Glu Ala Ala Lys Val Ile Cys Ala Ile
                50                  55                  60

Ile Leu Leu Ile Ala Glu Gly Ser Leu Arg Lys Gln Phe Ser Asn Trp
65              70                  75                  80

Thr Leu Thr Gly Ser Leu Thr Ala Ser Gly Leu Pro Ala Ala Ile Tyr
                85                  90                  95

Ala Leu Gln Asn Ser Leu Leu Gln Val Ser Tyr Lys Asn Leu Asp Ser
                100                 105                 110

Leu Thr Phe Ser Ile Leu Asn Gln Thr Lys Leu Leu Trp Thr Ala Phe
                115                 120                 125

Phe Thr Phe Leu Ile Leu Gly Gln Lys Gln Ser Ser Arg Gln Ile Leu
                130                 135                 140

Ala Leu Ala Leu Leu Ile Gly Ala Ala Val Leu Leu Ser Val Gly Glu
145                 150                 155                 160

Ser Thr Ser Lys Gly Ser Lys Ser Gly Gly Ser Asp Tyr Ile Leu Leu
                165                 170                 175

Tyr Gly Ile Ile Pro Val Thr Val Ala Ser Met Leu Ser Gly Leu Ala
                180                 185                 190

Ser Ser Leu Cys Gln Trp Ala Ser Gln Val Lys Lys His Thr Ser Tyr
                195                 200                 205

Met Met Thr Ile Glu Met Ser Phe Ile Gly Ser Met Cys Leu Leu Ala
                210                 215                 220

Ser Thr Tyr Arg Ser Pro Asp Gly Glu Ala Ile Arg Lys Tyr Gly Phe
225                 230                 235                 240

Phe His Glu Trp Thr Phe Trp Thr Val Val Pro Val Leu Met Asn Ala
                245                 250                 255
```

```
Val Gly Gly Ile Leu Val Gly Leu Val Thr Thr Tyr Ala Gly Gly Val
            260                 265                 270

Arg Lys Gly Phe Val Ile Val Ser Ala Leu Leu Val Thr Ala Leu Leu
        275                 280                 285

Gln Phe Val Phe Asp Gly Lys Pro Pro Ser Leu Tyr Cys Leu Met Ala
    290                 295                 300

Leu Pro Leu Val Ala Thr Ser Ile Phe Ile Tyr Gln Lys Tyr Pro Tyr
305                 310                 315                 320

Val Asp Arg Lys Lys Lys Asp
                325

<210> SEQ ID NO 22
<211> LENGTH: 326
<212> TYPE: PRT
<213> ORGANISM: Hordeum vulgare

<400> SEQUENCE: 22

Met Gly Ser Ala Ser Lys Pro Ser Pro Ser Ala Ala Pro Ser Arg
1               5                   10                  15

Arg Lys Val Ala Leu Cys Leu Thr Leu Leu Thr Leu Gln Tyr Gly Ala
            20                  25                  30

Gln Pro Leu Ile Ser Lys Arg Cys Val Gly Gln Gly Val Ile Val Thr
        35                  40                  45

Ser Leu Val Leu Ala Ile Glu Leu Leu Lys Val Ile Cys Ala Val Ile
    50                  55                  60

Leu Leu Val Ala Glu Gly Ser Leu Lys Ala Gln Phe Ser Asn Trp Ser
65                  70                  75                  80

Leu Val Gly Ser Leu Thr Ala Ser Gly Leu Pro Ala Ala Ile Tyr Ala
                85                  90                  95

Leu Gln Asn Ser Leu Leu Gln Ile Ser Tyr Lys Asn Leu Asp Ser Leu
            100                 105                 110

Thr Phe Ser Ile Leu Asn Gln Thr Lys Leu Leu Phe Thr Ala Phe Phe
        115                 120                 125

Thr Tyr Leu Ile Leu Gly Gln Lys Gln Ser Pro Lys Gln Ile Leu Ala
    130                 135                 140

Leu Ala Leu Leu Ile Thr Ala Ser Val Leu Leu Ser Ile Gly Glu Ser
145                 150                 155                 160

Ser Arg Lys Gly Val Ser Gly Gly Ser Ser Asp Tyr Val Leu Leu Tyr
                165                 170                 175

Gly Ile Ile Pro Val Thr Val Ala Ser Val Leu Ser Gly Leu Ala Ser
            180                 185                 190

Ser Leu Cys Gln Trp Ala Ser Gln Val Lys Lys His Thr Ser Tyr Met
        195                 200                 205

Met Thr Ile Glu Met Ser Phe Ile Gly Ser Met Cys Leu Leu Ala Ser
    210                 215                 220

Thr Phe Gln Ser Pro Asp Gly Glu Ala Leu Arg Ile Tyr Gly Phe Phe
225                 230                 235                 240

His Glu Trp Thr Leu Trp Thr Val Ile Pro Val Leu Met Asn Ala Val
                245                 250                 255

Gly Gly Ile Leu Val Gly Leu Val Thr Ser Tyr Ala Gly Gly Val Lys
            260                 265                 270

Lys Gly Phe Val Ile Val Leu Ala Leu Leu Val Thr Ala Leu Leu Gln
        275                 280                 285

Phe Ile Phe Asp Gly Lys Leu Pro Ser Leu His Cys Leu Val Ala Leu
    290                 295                 300
```

Pro Leu Val Met Thr Ser Ile Phe Ile Tyr Gln Lys Tyr Pro Tyr Val
305                 310                 315                 320

Asp Arg Lys Lys Lys Asp
                325

<210> SEQ ID NO 23
<211> LENGTH: 325
<212> TYPE: PRT
<213> ORGANISM: Setaria italica

<400> SEQUENCE: 23

Met Gly Ser Ser Thr Pro Ala Ala Ala Val Pro Ser Arg Arg
1               5                   10                  15

Lys Val Ala Leu Tyr Leu Thr Leu Leu Thr Leu Gln Tyr Gly Ala Gln
                20                  25                  30

Pro Leu Ile Ser Lys Arg Phe Val Arg Gln Asp Thr Ile Val Thr Ser
                35                  40                  45

Leu Val Leu Ala Thr Glu Gly Ala Lys Val Ile Cys Ala Ile Ile Leu
    50                  55                  60

Leu Ile Ala Glu Gly Gly Leu Lys Lys Gln Phe Ser Asn Trp Ser Leu
65                  70                  75                  80

Thr Gly Ser Leu Thr Ala Ser Gly Leu Pro Ala Ala Ile Tyr Ala Leu
                85                  90                  95

Gln Asn Ser Leu Leu Gln Ile Ser Tyr Lys Asn Leu Asp Ser Leu Thr
                100                 105                 110

Phe Ser Ile Leu Asn Gln Thr Lys Leu Leu Trp Thr Ala Phe Phe Thr
                115                 120                 125

Tyr Leu Ile Leu Gly Gln Lys Gln Ser Ser Lys Gln Ile Leu Ala Leu
130                 135                 140

Thr Leu Leu Ile Ser Ala Ala Val Leu Leu Ser Val Gly Glu Ser Ser
145                 150                 155                 160

Ser Lys Gly Ser Lys Gly Gly Ser Ser Asp Tyr Val Leu Leu Tyr Gly
                165                 170                 175

Ile Ile Pro Val Thr Val Ala Ser Met Leu Ser Gly Leu Ala Ser Ser
                180                 185                 190

Leu Cys Gln Trp Ala Ser Gln Val Lys Lys His Thr Ser Tyr Met Met
                195                 200                 205

Thr Ile Glu Met Ser Phe Ile Gly Ser Leu Cys Leu Leu Ala Ser Thr
210                 215                 220

Tyr Arg Ser Pro Asp Gly Glu Ala Ile Arg Lys Tyr Gly Phe His
225                 230                 235                 240

Glu Trp Thr Leu Trp Thr Thr Val Pro Val Leu Met Asn Ala Val Gly
                245                 250                 255

Gly Ile Leu Val Gly Leu Val Thr Thr Tyr Ala Gly Gly Val Arg Lys
                260                 265                 270

Gly Phe Val Ile Val Ser Ala Leu Leu Val Thr Ala Leu Leu Gln Phe
                275                 280                 285

Ile Phe Asp Gly Lys Pro Pro Ser His Tyr Cys Leu Met Ala Leu Pro
                290                 295                 300

Leu Val Met Thr Ser Ile Phe Ile Tyr Gln Lys Tyr Pro Tyr Ala Asp
305                 310                 315                 320

Arg Lys Lys Lys Asp
                325

<210> SEQ ID NO 24
<211> LENGTH: 327
<212> TYPE: PRT
<213> ORGANISM: Zea mays

<400> SEQUENCE: 24

Met Gly Ser Ser Ala Pro Ala Ala Ala Ala Ala Ala Pro Ser
1               5                   10                  15

Arg Arg Lys Val Ala Leu Tyr Leu Ala Leu Leu Thr Leu Gln Tyr Gly
            20                  25                  30

Ala Gln Pro Leu Ile Ser Lys Arg Phe Val Arg Glu Asp Thr Ile Val
        35                  40                  45

Thr Ser Leu Val Leu Ala Thr Glu Ala Ala Lys Val Ile Cys Ala Ile
    50                  55                  60

Ile Leu Leu Ile Ala Glu Gly Ser Leu Lys Lys Gln Phe Ser Asn Trp
65                  70                  75                  80

Thr Leu Thr Gly Ser Leu Thr Ala Ser Gly Leu Pro Ala Ala Ile Tyr
                85                  90                  95

Ala Leu Gln Asn Ser Leu Leu Gln Val Ser Tyr Lys His Leu Asp Ser
            100                 105                 110

Leu Thr Phe Ser Ile Leu Asn Gln Thr Lys Leu Leu Trp Thr Ala Phe
        115                 120                 125

Phe Thr Phe Leu Ile Leu Gly Gln Lys Gln Ser Ser Arg Gln Ile Leu
    130                 135                 140

Ala Leu Ala Leu Leu Ile Gly Ala Ala Val Leu Leu Ser Val Gly Glu
145                 150                 155                 160

Ser Ser Ser Lys Gly Ser Lys Gly Gly Gly Ser Asp Tyr Ile Leu Leu
                165                 170                 175

Tyr Gly Ile Ile Pro Val Thr Val Ala Ser Val Leu Ser Gly Leu Ala
            180                 185                 190

Ser Ser Leu Cys Gln Trp Ala Ser Gln Val Lys Lys His Thr Ser Tyr
        195                 200                 205

Met Met Thr Ile Glu Met Ser Phe Ile Gly Ser Met Cys Leu Leu Ala
    210                 215                 220

Ser Thr Tyr Arg Ser Pro Asp Gly Glu Ala Ile Arg Lys Tyr Gly Phe
225                 230                 235                 240

Phe His Glu Trp Thr Phe Trp Thr Val Ile Pro Val Leu Met Asn Ala
                245                 250                 255

Val Gly Gly Ile Leu Val Gly Leu Val Thr Thr Tyr Ala Gly Gly Val
            260                 265                 270

Arg Lys Gly Phe Val Ile Val Ser Ala Leu Leu Val Thr Ala Leu Leu
        275                 280                 285

Gln Phe Ile Phe Asp Gly Lys Leu Pro Ser Leu Tyr Cys Leu Ile Ala
    290                 295                 300

Leu Pro Leu Val Ala Ser Ser Ile Phe Ile Tyr Gln Lys His Pro Tyr
305                 310                 315                 320

Val Asp Arg Lys Lys Lys Asp
                325

<210> SEQ ID NO 25
<211> LENGTH: 327
<212> TYPE: PRT
<213> ORGANISM: Zea mays

<400> SEQUENCE: 25

Met Gly Ala Ser Ser Thr Pro Ala Ala Ala Ala Ala Ala Pro Ser

```
            1               5                  10                 15
          Arg Arg Lys Val Thr Leu Tyr Leu Val Leu Thr Leu Gln Tyr Gly
                           20                 25                 30

Ala Gln Pro Leu Ile Ser Lys Arg Phe Val Arg Gln Asp Thr Ile Val
                       35                 40                 45

Thr Ser Leu Val Leu Ala Thr Glu Ala Ala Lys Val Ile Cys Ala Ile
                   50                 55                 60

Ile Leu Leu Ile Ala Asp Gly Ser Leu Lys Gln Phe Ser Asn Trp
          65                 70                 75                 80

Thr Leu Ile Gly Ser Leu Thr Ala Ser Gly Leu Pro Ala Ala Ile Tyr
                                85                 90                 95

Ala Leu Gln Asn Ser Leu Leu Gln Val Ser Phe Lys Asn Leu Asp Ser
                           100                105                110

Leu Thr Phe Ser Ile Leu Asn Gln Thr Lys Leu Leu Trp Thr Ser Phe
                       115                120                125

Phe Thr Phe Leu Ile Leu Gly Gln Lys Gln Ser Ser Lys Gln Ile Leu
                   130                135                140

Ala Leu Ala Leu Leu Ile Ser Ala Ala Val Leu Leu Ser Val Gly Glu
          145                150                155                160

Ser Thr Ser Lys Gly Ser Asn Gly Gly Gly Ser Asp Tyr Ile Leu Leu
                           165                170                175

Tyr Gly Ile Ile Pro Val Thr Val Ala Ser Met Leu Ser Gly Leu Ala
                       180                185                190

Ser Ser Leu Cys Gln Trp Ala Ser Gln Val Lys Lys His Thr Ser Tyr
                   195                200                205

Met Met Thr Ile Glu Met Ser Phe Ile Gly Ser Val Cys Leu Leu Ala
          210                215                220

Ser Thr Tyr Arg Ser Pro Asp Gly Glu Ala Ile Arg Lys Tyr Gly Val
                           230                235                240
          225

Phe His Glu Trp Thr Phe Trp Thr Met Val Pro Val Leu Met Asn Ala
                       245                250                255

Val Gly Gly Ile Leu Val Gly Leu Val Thr Thr Tyr Ala Gly Gly Ile
                   260                265                270

Arg Lys Gly Phe Val Ile Val Ser Ala Leu Leu Val Thr Ala Leu Leu
          275                280                285

Gln Phe Val Tyr Asp Gly Lys Pro Pro Ser Leu Tyr Cys Leu Met Ala
                           290                295                300

Leu Pro Leu Val Ala Thr Ser Ile Phe Ile Tyr Gln Lys Tyr Pro Tyr
          305                310                315                320

Val Asp Lys Lys Lys Lys Val
                           325

<210> SEQ ID NO 26
<211> LENGTH: 327
<212> TYPE: PRT
<213> ORGANISM: Triticum aestivum

<400> SEQUENCE: 26

Met Gly Ser Ala Ser Lys Pro Ser Pro Thr Ala Ala Pro Ser Arg
          1                5                  10                 15

Arg Lys Val Ala Leu Cys Leu Thr Leu Leu Thr Leu Gln Tyr Gly Ala
                           20                 25                 30

Gln Pro Leu Ile Ser Lys Arg Cys Val Gly Gln Gly Val Ile Val Thr
                       35                 40                 45
```

```
Ser Leu Val Leu Ala Ile Glu Leu Lys Val Ile Cys Ala Val Ile
    50                  55                  60

Leu Leu Val Ala Glu Gly Ser Leu Lys Glu Gln Phe Ser Asn Trp Ser
65                  70                  75                  80

Leu Val Gly Ser Leu Thr Ala Ser Gly Leu Pro Ala Ala Ile Tyr Ala
                85                  90                  95

Leu Gln Asn Ser Leu Leu Gln Ile Ser Tyr Lys Asn Leu Asp Ser Leu
            100                 105                 110

Thr Phe Ser Ile Leu Asn Gln Thr Lys Leu Leu Phe Thr Ala Phe Phe
        115                 120                 125

Thr Tyr Leu Ile Leu Gly Gln Lys Gln Ser Pro Lys Gln Ile Leu Ala
130                 135                 140

Leu Ala Leu Leu Ile Thr Ala Ala Val Leu Leu Ser Ile Gly Glu Ser
145                 150                 155                 160

Ser Arg Lys Gly Ala Ser Gly Gly Ser Ser Asp Tyr Val Leu Leu Tyr
                165                 170                 175

Gly Ile Ile Pro Val Thr Val Ala Ser Val Leu Ser Gly Leu Ala Ser
            180                 185                 190

Ser Leu Cys Gln Trp Ala Ser Gln Val Lys Lys His Thr Ser Tyr Met
        195                 200                 205

Met Thr Ile Glu Met Ser Phe Ile Gly Ser Met Cys Leu Leu Ala Ser
210                 215                 220

Thr Phe Gln Ser Pro Asp Gly Glu Ala Leu Arg Ile Tyr Gly Phe Phe
225                 230                 235                 240

His Glu Trp Thr Leu Trp Thr Val Ile Pro Val Leu Met Asn Ala Val
                245                 250                 255

Gly Gly Ile Leu Val Gly Leu Val Thr Ser Tyr Ala Gly Gly Ile Lys
            260                 265                 270

Lys Gly Phe Val Ile Val Ser Ala Leu Leu Val Thr Ala Leu Leu Gln
        275                 280                 285

Phe Ile Phe Asp Gly Lys Pro Pro Ser Leu His Cys Leu Val Ala Leu
290                 295                 300

Pro Leu Val Met Thr Ser Ile Phe Ile Tyr Gln Lys Tyr Pro Tyr Val
305                 310                 315                 320

Asp Ser Lys Lys Lys Asp Arg
                325

<210> SEQ ID NO 27
<211> LENGTH: 326
<212> TYPE: PRT
<213> ORGANISM: Oryza sativa

<400> SEQUENCE: 27

Met Gly Ser Ser Ala Thr Pro Ser Thr Ala Ala Ser Ala Pro Gly Arg
1               5                   10                  15

Arg Lys Val Ala Leu Tyr Leu Ala Leu Leu Thr Leu Gln Tyr Gly Ala
                20                  25                  30

Gln Pro Leu Ile Ser Lys Arg Phe Val Arg Gln Glu Val Ile Val Thr
            35                  40                  45

Thr Leu Val Leu Ser Ile Glu Val Ala Lys Val Ile Cys Ala Val Ile
        50                  55                  60

Leu Leu Val Ala Glu Gly Ser Leu Lys Lys Gln Phe Asn Asn Trp Ser
65                  70                  75                  80

Ile Thr Arg Ser Leu Thr Ala Ser Gly Leu Pro Ala Ala Ile Tyr Ala
                85                  90                  95
```

Leu Gln Asn Ser Leu Leu Gln Ile Ser Tyr Lys Asn Leu Asp Ser Leu
            100                 105                 110

Thr Phe Ser Ile Leu Asn Gln Thr Lys Leu Leu Phe Thr Ala Phe Phe
        115                 120                 125

Thr Tyr Leu Ile Leu Gly Gln Lys Gln Ser Pro Lys Gln Ile Phe Ala
        130                 135                 140

Leu Thr Leu Leu Ile Ala Ala Val Leu Leu Ser Ile Gly Glu Ser
145                 150                 155                 160

Ser Ser Lys Gly Ser Gly Gly Asn Ser Asp Tyr Ile Leu Leu Tyr
                165                 170                 175

Gly Ile Ile Pro Val Thr Val Ala Ser Val Leu Ser Gly Leu Ala Ser
                180                 185                 190

Ser Leu Cys Gln Trp Ala Ser Gln Val Lys Lys His Thr Ser Tyr Met
            195                 200                 205

Met Thr Ile Glu Met Ser Phe Ile Gly Ser Met Cys Leu Leu Ala Ser
        210                 215                 220

Thr Ser Gln Ser Pro Asp Gly Glu Ala Ile Arg Lys His Gly Phe Phe
225                 230                 235                 240

His Glu Trp Thr Leu Leu Thr Val Val Pro Val Leu Met Asn Ala Val
                245                 250                 255

Gly Gly Ile Leu Val Gly Leu Val Thr Thr Tyr Ala Gly Gly Val Arg
                260                 265                 270

Lys Gly Phe Val Ile Val Ser Ala Leu Leu Val Thr Ala Leu Leu Gln
            275                 280                 285

Phe Ile Phe Asp Gly Lys Pro Pro Ser Leu Tyr Cys Leu Ile Ala Leu
        290                 295                 300

Pro Leu Val Met Thr Ser Ile Phe Ile Tyr Gln Lys Tyr Pro Tyr Val
305                 310                 315                 320

Asp Arg Lys Lys Lys Asp
                325

<210> SEQ ID NO 28
<211> LENGTH: 327
<212> TYPE: PRT
<213> ORGANISM: Glycine max

<400> SEQUENCE: 28

Met Ala Pro Pro Ala Pro Pro Lys Ser Ser Gln Gly Gln Val Met Asn
1               5                   10                  15

Asn Ala Arg Ile His Phe Phe Ser Ile Leu Leu Ala Leu Gln Tyr Gly
            20                  25                  30

Ala Gln Pro Leu Ile Ser Lys Arg Phe Ile Arg Arg Glu Val Ile Val
        35                  40                  45

Thr Ser Ser Val Leu Thr Cys Glu Leu Ala Lys Val Ile Cys Ala Val
    50                  55                  60

Phe Phe Met Ala Lys Asp Gly Ser Leu Arg Lys Leu Tyr Lys Glu Trp
65                  70                  75                  80

Thr Leu Val Gly Ala Leu Thr Ala Ser Gly Leu Pro Ala Ala Ile Tyr
                85                  90                  95

Ala Leu Gln Asn Ser Leu Leu Gln Ile Ser Tyr Lys Asn Leu Asp Ser
            100                 105                 110

Leu Thr Phe Ser Met Leu Asn Gln Thr Lys Ile Phe Phe Thr Ala Leu
        115                 120                 125

Phe Ala Tyr Phe Ile Leu Arg Gln Lys Gln Ser Ile Glu Gln Ile Gly

```
                    130                 135                 140
Ala Leu Phe Leu Leu Ile Val Ala Ala Val Leu Leu Ser Val Gly Glu
145                 150                 155                 160

Gly Ser Thr Lys Gly Ser Ala Ile Gly Asn Ala Asp Gln Ile Leu Phe
                165                 170                 175

Tyr Gly Ile Ile Pro Val Leu Val Ala Ser Val Leu Ser Gly Leu Ala
            180                 185                 190

Ser Ser Leu Cys Gln Trp Ala Ser Gln Val Lys Lys His Ser Ser Tyr
        195                 200                 205

Leu Met Thr Ile Glu Met Ser Ile Val Gly Ser Leu Cys Leu Leu Ala
        210                 215                 220

Ser Thr Leu Lys Ser Pro Asp Gly Glu Ala Met Arg Gln His Gly Phe
225                 230                 235                 240

Phe Tyr Gly Trp Thr Pro Leu Thr Leu Ile Pro Val Ile Phe Asn Ala
                245                 250                 255

Leu Gly Gly Ile Leu Val Gly Leu Val Thr Ser His Ala Gly Gly Val
                260                 265                 270

Arg Lys Gly Phe Val Ile Val Ser Ala Leu Leu Ile Thr Ala Leu Leu
            275                 280                 285

Gln Phe Ile Phe Asp Gly Lys Thr Pro Ser Leu Tyr Cys Leu Leu Ala
        290                 295                 300

Leu Pro Leu Val Val Thr Ser Ile Ser Ile Tyr Gln Lys Tyr Pro Tyr
305                 310                 315                 320

Gln Val Lys Lys Lys Glu Ser
                325

<210> SEQ ID NO 29
<211> LENGTH: 329
<212> TYPE: PRT
<213> ORGANISM: Phaseolus vulgaris

<400> SEQUENCE: 29

Met Ala Pro Pro Pro Pro Lys Ser Arg Gly Ala Thr Gln Gly Ile
1               5                   10                  15

Asn Asn Ala Ala Arg Ile Gln Phe Phe Ser Ile Leu Leu Ala Leu Gln
                20                  25                  30

Tyr Gly Ala Gln Pro Leu Ile Ser Lys Arg Phe Val Arg Gln Glu Val
            35                  40                  45

Ile Val Thr Ser Ser Val Leu Val Cys Glu Leu Ala Lys Val Leu Cys
50                  55                  60

Ala Val Phe Ile Met Ala Lys Asp Gly Thr Leu Arg Lys Val Tyr Lys
65                  70                  75                  80

Glu Trp Thr Leu Val Gly Ala Leu Thr Ala Ser Gly Leu Pro Ala Ala
                85                  90                  95

Ile Tyr Ala Leu Gln Asn Ser Leu Leu Gln Ile Ser Tyr Lys Asn Leu
                100                 105                 110

Asp Ser Leu Thr Phe Ser Met Leu Asn Gln Thr Lys Ile Phe Phe Thr
            115                 120                 125

Ala Phe Phe Thr Tyr Phe Ile Leu Arg Gln Lys Gln Ser Ile Glu Gln
        130                 135                 140

Ile Gly Ala Leu Phe Leu Leu Ile Val Ala Ala Val Leu Leu Ser Val
145                 150                 155                 160

Gly Glu Gly Ser Ser Lys Gly Ser Ser Val Asn Ala Asp Gln Ile
                165                 170                 175
```

```
Leu Phe Tyr Gly Ile Ile Pro Val Leu Val Ala Ser Val Leu Ser Gly
            180                 185                 190

Leu Ala Ser Ser Leu Cys Gln Trp Ala Ser Gln Val Lys Lys His Ser
        195                 200                 205

Ser Tyr Leu Met Thr Ile Glu Met Ser Ile Val Gly Ser Leu Cys Leu
    210                 215                 220

Leu Ala Ser Thr Phe Lys Ser Pro Asp Gly Glu Ala Met Arg Gln His
225                 230                 235                 240

Gly Phe Phe Tyr Gly Trp Thr Pro Leu Thr Leu Ile Pro Val Met Phe
                245                 250                 255

Asn Ala Phe Gly Gly Ile Leu Val Gly Leu Val Thr Ser His Ala Gly
            260                 265                 270

Gly Val Arg Lys Gly Phe Val Ile Val Ser Ala Leu Leu Ile Thr Ala
        275                 280                 285

Leu Leu Gln Phe Ile Phe Asp Gly Lys Pro Pro Ser Leu Tyr Cys Leu
    290                 295                 300

Val Ala Leu Pro Leu Val Val Thr Ser Ile Ser Ile Tyr Gln Lys Tyr
305                 310                 315                 320

Pro Asn Gln Val Lys Lys Lys Glu Ser
                325

<210> SEQ ID NO 30
<211> LENGTH: 324
<212> TYPE: PRT
<213> ORGANISM: Cicer arietinum

<400> SEQUENCE: 30

Met Ala Pro Pro Lys Ser Lys Ala Pro Thr Gln Ala Thr Asn Thr Arg
1               5                   10                  15

Ile Phe Phe Phe Ser Ile Leu Leu Ala Leu Gln Tyr Gly Ala Gln Pro
            20                  25                  30

Leu Ile Ser Lys Arg Cys Ile Ser Arg Glu Val Ile Val Thr Ser Ser
        35                  40                  45

Val Leu Ala Cys Glu Ala Ala Lys Val Ile Phe Ala Val Tyr Phe Met
    50                  55                  60

Ala Lys Glu Gly Ser Leu Gly Arg Thr Phe Lys Glu Trp Thr Leu Val
65                  70                  75                  80

Gly Ala Leu Thr Ala Ser Gly Leu Pro Ala Ala Ile Tyr Ala Leu Gln
                85                  90                  95

Asn Ser Leu Leu Gln Ile Ser Tyr Lys Asn Leu Asp Ser Leu Thr Phe
            100                 105                 110

Ser Met Leu Asn Gln Thr Lys Ile Ile Phe Thr Ala Leu Phe Thr Tyr
        115                 120                 125

Phe Met Leu Arg Gln Lys Gln Ser Ile Gln Gln Ile Gly Ala Leu Phe
    130                 135                 140

Leu Leu Ile Ala Ala Ala Val Leu Leu Ser Val Gly Glu Gly Ser Asn
145                 150                 155                 160

Lys Gly Ser Thr Ser Gly Asn Ala Asp Gln Ile Leu Phe Tyr Gly Ile
                165                 170                 175

Val Pro Val Leu Ile Ala Ser Leu Leu Ser Gly Leu Ala Ser Ser Leu
            180                 185                 190

Cys Gln Trp Ala Ser Gln Val Lys Lys His Ser Ser Tyr Leu Met Thr
        195                 200                 205

Val Glu Met Ser Ile Val Gly Ser Leu Cys Leu Leu Ala Ser Thr Phe
    210                 215                 220
```

```
Lys Ser Pro Asp Gly Glu Ala Met Arg Gln His Gly Phe Phe His Ala
225                 230                 235                 240

Trp Thr Pro Leu Thr Trp Ile Pro Val Ile Phe Asn Ala Leu Gly Gly
            245                 250                 255

Ile Leu Val Gly Leu Val Thr Ser Tyr Ala Gly Gly Val Arg Lys Gly
        260                 265                 270

Phe Val Ile Val Ser Ala Leu Leu Val Thr Ala Leu Leu Gln Phe Ile
    275                 280                 285

Phe Glu Gly Lys Pro Pro Ser Leu Tyr Cys Leu Val Ala Leu Pro Leu
290                 295                 300

Val Val Gly Ser Ile Ser Ile Tyr Gln Lys Tyr Pro Tyr Gln Ile Lys
305                 310                 315                 320

Lys Lys Glu Ser

<210> SEQ ID NO 31
<211> LENGTH: 327
<212> TYPE: PRT
<213> ORGANISM: Vitis vinifera

<400> SEQUENCE: 31

Met Ala Thr Lys Lys Arg Gly Val Pro Thr Ala Ile Pro Glu Lys Ala
1               5                   10                  15

Ser Pro Arg Val Trp Leu Tyr Leu Val Leu Leu Thr Leu Gln Tyr Gly
            20                  25                  30

Ala Gln Pro Leu Ile Ser Lys Arg Phe Ile Arg Arg Glu Val Ile Val
        35                  40                  45

Thr Ser Ser Val Leu Thr Cys Glu Val Ala Lys Val Ile Cys Ala Leu
    50                  55                  60

Phe Leu Ile Ala Arg Gly Gly Gly Leu Lys Lys Leu Tyr Asn Glu Trp
65                  70                  75                  80

Thr Leu Val Gly Ser Leu Thr Ala Ser Gly Leu Pro Ala Ala Ile Tyr
                85                  90                  95

Ala Leu Gln Asn Ser Leu Leu Gln Ile Ser Tyr Lys Asn Leu Asp Ser
            100                 105                 110

Leu Thr Phe Ser Met Leu Asn Gln Thr Lys Leu Phe Phe Thr Ala Leu
        115                 120                 125

Phe Thr Tyr Ile Ile Leu Arg Gln Lys Gln Ser Thr Gln Gln Ile Gly
    130                 135                 140

Ala Leu Phe Leu Leu Ile Ile Ala Ala Val Leu Leu Ser Ile Gly Glu
145                 150                 155                 160

Gly Ser Ser Lys Gly Ser Ser Gly Ser Asn Pro Asp Gln Ile Leu Phe
                165                 170                 175

His Gly Ile Val Pro Val Leu Val Ala Ser Val Leu Ser Gly Leu Ala
            180                 185                 190

Ser Ala Leu Cys Gln Trp Ala Ser Gln Val Lys Lys His Thr Ser Tyr
        195                 200                 205

Met Met Thr Ile Glu Met Ser Val Val Gly Ser Leu Cys Leu Leu Ala
    210                 215                 220

Ser Thr Tyr Lys Ser Pro Asp Gly Lys Ala Ile Arg Gln His Gly Phe
225                 230                 235                 240

Phe Tyr Gly Trp Thr Pro Leu Thr Leu Ile Pro Val Ile Phe Asn Ala
            245                 250                 255

Val Gly Gly Ile Leu Val Gly Leu Val Thr Ser Tyr Ala Gly Gly Val
        260                 265                 270
```

```
Arg Lys Gly Phe Val Ile Val Ser Ala Leu Leu Val Thr Ala Leu Leu
        275                 280                 285

Gln Phe Ile Phe Asp Gly Lys Pro Pro Ser Phe Tyr Cys Ile Leu Ala
290                 295                 300

Leu Pro Leu Val Ile Thr Ser Ile Ser Ile Tyr Gln Lys Tyr Pro Tyr
305                 310                 315                 320

Arg Val Lys Lys Lys Glu Ser
                325

<210> SEQ ID NO 32
<211> LENGTH: 330
<212> TYPE: PRT
<213> ORGANISM: Solanum lycopersicum

<400> SEQUENCE: 32

Met Ala Ala Thr Glu Ser Lys Lys Val Asn Ser Glu Asn Pro Ala Ala
1               5                   10                  15

Ala Lys Thr Gly Gly Lys Val Trp Phe Tyr Ser Leu Leu Leu Thr Leu
            20                  25                  30

Gln Tyr Gly Ala Gln Pro Leu Ile Ser Lys Arg Phe Val Arg Arg Glu
        35                  40                  45

Val Ile Val Thr Ser Ser Val Leu Thr Cys Glu Ala Val Lys Val Ile
50                  55                  60

Cys Ala Leu Val Leu Met Ala Lys Glu Gly Thr Leu Lys Lys Ile Tyr
65                  70                  75                  80

Arg Glu Trp Thr Leu Phe Gly Ser Leu Thr Ala Ser Gly Leu Pro Ala
                85                  90                  95

Ala Ile Tyr Ala Leu Gln Asn Ser Leu Leu Gln Ile Ser Tyr Lys Asn
            100                 105                 110

Leu Asp Ser Leu Thr Phe Ser Ile Leu Asn Gln Thr Lys Leu Phe Phe
        115                 120                 125

Thr Ala Leu Phe Thr Tyr Ile Ile Leu Arg Gln Lys Gln Ser Ile Gln
    130                 135                 140

Gln Ile Gly Ala Leu Phe Leu Leu Ile Met Ala Ala Val Leu Leu Ser
145                 150                 155                 160

Val Gly Glu Gly Ser Ser Lys Ala Ser Ser Ser Asn Pro Asp Glu
                165                 170                 175

Ile Leu Phe Tyr Gly Ile Val Pro Val Leu Val Ala Ser Val Leu Ser
            180                 185                 190

Gly Leu Ala Ser Ala Leu Cys Gln Trp Ala Ser Gln Val Lys Lys His
        195                 200                 205

Ser Ser Tyr Leu Met Thr Val Glu Met Ser Ile Gly Ser Leu Cys
    210                 215                 220

Leu Ile Ser Ser Thr Ser Lys Ser Pro Asp Gly Glu Ala Ile Arg Gln
225                 230                 235                 240

His Gly Phe Phe Tyr Gly Trp Thr Ala Leu Thr Leu Ile Pro Val Ile
                245                 250                 255

Leu Asn Ala Val Gly Gly Ile Leu Val Gly Leu Val Thr Ser Tyr Ala
            260                 265                 270

Gly Gly Val Arg Lys Gly Phe Val Ile Val Ser Ala Leu Leu Val Thr
        275                 280                 285

Ala Leu Leu Gln Phe Ile Phe Asp Gly Lys Leu Pro Ser Pro Tyr Cys
    290                 295                 300

Leu Val Ala Leu Pro Leu Val Met Ile Ser Ile Ser Thr Tyr Gln Lys
```

```
                305                 310                 315                 320
Tyr Pro Tyr Arg Val Lys Lys Lys Gln Met
                325                 330

<210> SEQ ID NO 33
<211> LENGTH: 312
<212> TYPE: PRT
<213> ORGANISM: Theobroma cacao

<400> SEQUENCE: 33

Met Ser Pro Arg Val Trp Leu Tyr Ser Ile Leu Leu Thr Phe Gln Tyr
1               5                   10                  15

Gly Ala Gln Pro Leu Ile Ser Lys Arg Phe Thr Arg Arg Glu Val Ile
            20                  25                  30

Val Thr Ser Ser Val Leu Thr Cys Glu Ile Ala Lys Val Ile Cys Ala
        35                  40                  45

Leu Ile Leu Met Ala Lys Asp Gly Thr Leu Lys Lys Met Ala Lys Glu
    50                  55                  60

Trp Thr Leu Val Gly Ser Leu Thr Ala Ser Gly Leu Pro Ala Ala Ile
65                  70                  75                  80

Tyr Ala Leu Gln Asn Ser Leu Leu Gln Ile Ser Tyr Arg Asn Leu Asp
                85                  90                  95

Ser Leu Thr Phe Ser Met Leu Asn Gln Thr Lys Ile Phe Phe Thr Ala
            100                 105                 110

Leu Phe Thr Tyr Ile Ile Leu Arg Gln Lys Gln Ser Ile Gln Gln Ile
        115                 120                 125

Gly Ala Leu Phe Leu Leu Ile Met Ala Ala Val Leu Leu Ser Ile Gly
    130                 135                 140

Glu Gly Ser Ser Lys Gly Ser Asn Ser Arg Asp Pro Asp Gln Ile Leu
145                 150                 155                 160

Phe Tyr Gly Ile Val Pro Val Leu Val Ala Ser Val Leu Ser Gly Leu
                165                 170                 175

Ala Ser Ala Leu Cys Gln Trp Ala Ser Gln Val Lys Lys His Ser Ser
            180                 185                 190

Tyr Leu Met Thr Val Glu Met Ser Ile Val Gly Ser Leu Cys Leu Leu
        195                 200                 205

Ala Ser Thr Ser Lys Ser Pro Asp Gly Glu Ala Ile Arg Arg His Gly
    210                 215                 220

Phe Phe Tyr Gly Trp Thr Pro Leu Thr Leu Ile Pro Val Val Ala Asn
225                 230                 235                 240

Ala Leu Gly Gly Ile Leu Val Gly Leu Val Thr Ser Leu Ala Gly Gly
                245                 250                 255

Val Arg Lys Gly Phe Val Ile Val Ser Ala Leu Leu Val Thr Ala Met
            260                 265                 270

Leu Gln Phe Leu Phe Glu Gly Lys Pro Pro Ser Val Tyr Cys Leu Val
        275                 280                 285

Ala Leu Pro Leu Val Ile Ser Ser Ile Ser Ile Tyr Gln Lys Tyr Pro
    290                 295                 300

Tyr Arg Val Lys Lys Lys Glu Ala
305                 310

<210> SEQ ID NO 34
<211> LENGTH: 331
<212> TYPE: PRT
<213> ORGANISM: Citrus sinensis
```

<400> SEQUENCE: 34

Met Ala Thr Val Lys Thr Lys Val Lys Thr Gly Pro Thr Gln Thr Ser
1               5                   10                  15

Met Gln Lys Thr Ser Ala Arg Val Phe Leu Tyr Ser Leu Leu Leu Thr
            20                  25                  30

Leu Gln Tyr Gly Val Gln Pro Leu Ile Ser Lys Arg Cys Ile Arg Arg
        35                  40                  45

Glu Val Ile Val Thr Thr Ser Val Leu Thr Cys Glu Leu Ala Lys Val
    50                  55                  60

Ile Phe Ala Leu Ile Phe Met Ala Lys Glu Gly Thr Leu Lys Lys Leu
65                  70                  75                  80

Ser Ser Gln Trp Thr Leu Val Gly Ser Leu Thr Ala Ser Gly Leu Pro
                85                  90                  95

Ala Thr Ile Tyr Ala Leu Gln Asn Ser Leu Leu Gln Ile Ser Tyr Arg
            100                 105                 110

Asn Leu Asp Ser Leu Thr Phe Ser Met Leu Asn Gln Thr Lys Ile Ile
        115                 120                 125

Phe Thr Ala Leu Phe Thr Tyr Ile Ile Leu Arg Gln Arg Gln Ser Met
130                 135                 140

Gln Gln Ile Val Ala Val Phe Leu Leu Ile Leu Ala Ala Val Phe Leu
145                 150                 155                 160

Ser Ile Gly Glu Gly Ser Ser Lys Arg Ser Ser Ser Gly Asp Pro Asp
                165                 170                 175

Gln Ile Leu Phe Tyr Gly Ile Val Pro Val Leu Val Ala Ser Val Leu
            180                 185                 190

Ser Gly Leu Ala Ser Ala Leu Cys Gln Trp Ala Ser Gln Val Lys Lys
        195                 200                 205

His Ser Ser Tyr Leu Met Thr Ile Glu Met Ser Ile Val Gly Ser Leu
210                 215                 220

Cys Leu Leu Ala Ser Ile Ser Lys Ser Pro Asp Gly Glu Ala Ile Arg
225                 230                 235                 240

Gln His Gly Phe Phe Tyr Gly Trp Thr Pro Leu Thr Leu Ile Pro Val
                245                 250                 255

Ile Phe Asn Ser Leu Gly Gly Ile Leu Val Gly Leu Val Thr Ser His
            260                 265                 270

Ala Gly Gly Val Arg Lys Gly Phe Val Ile Val Ser Ala Leu Leu Val
        275                 280                 285

Thr Ala Met Leu Gln Phe Ile Phe Glu Gly Lys Pro Pro Ser Leu Tyr
290                 295                 300

Cys Leu Ile Ala Leu Pro Leu Val Val Ser Ser Ile Ser Ile Tyr Gln
305                 310                 315                 320

Lys Tyr Pro Tyr Gln Val Lys Lys Lys Glu Val
                325                 330

<210> SEQ ID NO 35
<211> LENGTH: 331
<212> TYPE: PRT
<213> ORGANISM: Citrus clementina

<400> SEQUENCE: 35

Met Ala Thr Val Lys Thr Lys Val Lys Thr Gly Pro Thr Gln Thr Ser
1               5                   10                  15

Met Gln Lys Thr Ser Ala Arg Val Phe Leu Tyr Ser Leu Leu Leu Thr
            20                  25                  30

Leu Gln Tyr Gly Val Gln Pro Leu Ile Ser Lys Arg Cys Ile Arg Arg
            35                  40                  45

Glu Val Ile Val Thr Thr Ser Val Leu Thr Cys Glu Leu Ala Lys Val
 50                  55                  60

Ile Phe Ala Leu Ile Phe Met Ala Lys Glu Gly Thr Leu Lys Lys Leu
 65                  70                  75                  80

Ser Ser Gln Trp Thr Leu Val Gly Ser Leu Thr Ala Ser Gly Leu Pro
                85                  90                  95

Ala Thr Ile Tyr Ala Leu Gln Asn Ser Leu Leu Gln Ile Ser Tyr Arg
                100                 105                 110

Asn Leu Asp Ser Leu Thr Phe Ser Met Leu Asn Gln Thr Lys Ile Ile
            115                 120                 125

Phe Thr Ala Leu Phe Thr Tyr Ile Ile Leu Arg Gln Arg Gln Ser Met
        130                 135                 140

Gln Gln Ile Val Ala Val Phe Leu Leu Ile Leu Ala Ala Val Phe Leu
145                 150                 155                 160

Ser Ile Gly Glu Gly Ser Ser Lys Arg Ser Ser Gly Asp Pro Asp
                165                 170                 175

Gln Ile Leu Phe Tyr Gly Ile Val Pro Val Leu Val Ala Ser Val Leu
                180                 185                 190

Ser Gly Leu Ala Ser Ala Leu Cys Gln Trp Ala Ser Gln Val Lys Lys
            195                 200                 205

His Ser Ser Tyr Leu Met Thr Ile Glu Met Ser Ile Val Gly Ser Leu
            210                 215                 220

Cys Leu Leu Ala Ser Ile Ser Lys Ser Pro Asp Gly Glu Ala Ile Arg
225                 230                 235                 240

Gln His Gly Phe Phe Tyr Gly Trp Thr Pro Leu Thr Leu Ile Pro Val
                245                 250                 255

Ile Phe Asn Ser Leu Gly Gly Ile Leu Val Gly Leu Val Thr Ser His
                260                 265                 270

Ala Gly Gly Val Arg Lys Gly Phe Val Ile Val Ser Ala Leu Leu Val
            275                 280                 285

Thr Ala Met Leu Gln Phe Ile Phe Glu Gly Lys Pro Pro Ser Leu Tyr
        290                 295                 300

Cys Leu Ile Ala Leu Pro Leu Val Val Ser Ser Ile Ser Ile Tyr Gln
305                 310                 315                 320

Lys Tyr Pro Tyr Gln Val Lys Lys Lys Glu Val
                325                 330

<210> SEQ ID NO 36
<211> LENGTH: 330
<212> TYPE: PRT
<213> ORGANISM: Picea sitchensis

<400> SEQUENCE: 36

Met Ala Val Lys Ser Arg Ala Arg Gly Lys Gln Asn Ser Glu Asp His
 1               5                  10                  15

Gln Lys His Lys Ser Arg Ile Trp Leu Tyr Leu Thr Leu Leu Thr Leu
            20                  25                  30

Gln Tyr Gly Ala Gln Pro Leu Leu Ser Lys Arg Phe Ser Gly Lys Gly
        35                  40                  45

Val Thr Val Thr Ser Ser Val Leu Ile Cys Glu Cys Ala Lys Val Leu
 50                  55                  60

Cys Ala Leu Ile Leu Ile Val Lys Glu Gly Ser Leu Gly Arg Leu Ser
 65                  70                  75                  80

```
Glu Glu Trp Thr Phe Ile Gly Ser Leu Thr Ala Ser Gly Leu Pro Ala
                85                  90                  95

Ala Ile Tyr Ala Leu Gln Asn Ser Leu Leu Gln Leu Ser Tyr Arg Asn
            100                 105                 110

Leu Asp Ser Leu Thr Phe Thr Met Leu Asn Gln Thr Lys Leu Phe Phe
        115                 120                 125

Thr Ala Leu Phe Met Tyr Phe Ile Leu Gly Gln Lys Gln Ser Leu Gln
    130                 135                 140

Gln Ile Gly Ala Leu Val Leu Leu Ile Ile Ala Ala Phe Leu Leu Ser
145                 150                 155                 160

Ile Gly Glu Gly Ser Gly His Gly Ser Arg Gly Val Asp Ser Glu Gln
                165                 170                 175

Ala Phe Leu Leu Gly Ile Ile Pro Val Ile Ala Ala Ser Val Leu Ser
            180                 185                 190

Gly Leu Ala Ser Ser Leu Cys Gln Trp Ala Ser Gln Val Lys Lys Arg
        195                 200                 205

Ser Ser Tyr Leu Met Thr Ile Glu Met Ser Ala Ile Gly Ser Leu Cys
    210                 215                 220

Met Leu Ala Ser Thr Leu Lys Ser Pro Asp Gly Lys Ala Ile Arg Gln
225                 230                 235                 240

Gln Gly Phe Phe Ser Gly Trp Thr Ile Leu Thr Leu Ile Pro Ile Phe
                245                 250                 255

Thr Asn Ala Val Gly Gly Ile Leu Val Gly Leu Val Thr Thr Gln Ala
            260                 265                 270

Gly Gly Val Arg Lys Gly Phe Val Ile Val Ser Ala Leu Ile Val Thr
        275                 280                 285

Ala Leu Leu Gln Tyr Val Phe Asp Gly Ile Pro Pro Ser Leu Tyr Val
    290                 295                 300

Leu Leu Ser Leu Pro Leu Val Val Thr Ser Ile Ile Ile Tyr Gln Arg
305                 310                 315                 320

Tyr Pro Tyr Gln Val Lys Glu Lys Lys Leu
                325                 330

<210> SEQ ID NO 37
<211> LENGTH: 336
<212> TYPE: PRT
<213> ORGANISM: Coffea canephora

<400> SEQUENCE: 37

Met Thr Ala Val Ala Glu Ala Ala Lys Ser Lys Val Thr Lys Ser
1               5                   10                  15

Ser Ser Gly Asp Gln Ile Ser Asn Pro Asn Gly Lys Val Trp Phe Tyr
            20                  25                  30

Ser Leu Leu Leu Thr Leu Gln Tyr Gly Ala Gln Pro Leu Ile Ser Lys
        35                  40                  45

Arg Cys Thr Gly Arg Glu Val Thr Val Thr Ser Leu Val Leu Thr Cys
    50                  55                  60

Glu Val Val Lys Val Ile Cys Ala Leu Leu Leu Met Ala Lys Asp Gly
65                  70                  75                  80

Thr Leu Lys Lys Leu Phe Lys Glu Trp Thr Leu Val Gly Ser Leu Thr
                85                  90                  95

Ala Ser Gly Leu Pro Ala Ala Ile Tyr Ala Leu Gln Asn Ser Leu Leu
            100                 105                 110

Gln Ile Ser Tyr Arg Asn Leu Asp Ser Leu Thr Phe Ser Met Leu Asn
```

```
            115                 120                 125
Gln Thr Lys Leu Phe Phe Thr Ala Phe Phe Met Tyr Met Ile Leu Arg
130                 135                 140

Gln Lys Gln Ser Ile Gln Gln Ile Gly Ala Leu Phe Leu Leu Ile Leu
145                 150                 155                 160

Ala Ala Val Leu Leu Ser Val Gly Glu Gly Ser Ser Lys Ala Ser Ser
                165                 170                 175

Ser Ser Asn Pro Glu Glu Ile Leu Phe Arg Gly Ile Ile Pro Val Leu
            180                 185                 190

Val Ala Ser Val Leu Ser Gly Leu Ala Ser Ala Leu Cys Gln Trp Ala
        195                 200                 205

Ser Gln Val Lys Lys His Thr Ser Tyr Leu Met Thr Val Glu Met Ser
    210                 215                 220

Ile Ile Gly Ser Leu Cys Leu Met Ala Ser Phe Tyr Lys Ser Pro Asp
225                 230                 235                 240

Gly Glu Thr Ile Arg Gln His Gly Phe Phe Tyr Asp Trp Thr Pro Leu
                245                 250                 255

Thr Leu Ile Pro Val Ile Phe Asn Ala Val Gly Gly Ile Leu Val Gly
            260                 265                 270

Leu Val Thr Ser Tyr Ala Gly Gly Val Arg Lys Ala Phe Val Ile Val
        275                 280                 285

Ser Ala Leu Leu Val Thr Ala Leu Leu Gln Phe Val Phe Asp Gly Lys
    290                 295                 300

Pro Pro Ser Leu Tyr Cys Leu Val Ala Leu Pro Leu Val Ile Thr Ser
305                 310                 315                 320

Val Ser Val Tyr Gln Lys Tyr Pro Tyr Arg Val Lys Ala Lys Glu Ala
                325                 330                 335

<210> SEQ ID NO 38
<211> LENGTH: 330
<212> TYPE: PRT
<213> ORGANISM: Musa acuminata

<400> SEQUENCE: 38

Met Ala Ser Ala Ala Thr Ala His Arg Lys Gly Pro Pro Arg Gln
1               5                   10                  15

Glu Ser Pro Arg Ala Lys Val Trp Leu Tyr Leu Thr Leu Leu Thr Leu
                20                  25                  30

Gln Tyr Gly Ala Gln Pro Leu Ile Ser Lys Arg Phe Ile Arg Arg Asp
            35                  40                  45

Val Ile Val Thr Ser Ser Val Leu Thr Cys Glu Met Ala Lys Val Ile
        50                  55                  60

Cys Ala Leu Phe Leu Leu Ala Lys Glu Gly Ser Phe Lys Arg Leu Trp
65                  70                  75                  80

Lys Glu Trp Thr Leu Val Gly Ala Leu Thr Ala Ser Gly Leu Pro Ala
                85                  90                  95

Ala Ile Tyr Ala Leu Gln Asn Ser Leu Leu Gln Ile Ser Tyr Lys Asn
            100                 105                 110

Leu Asp Ser Leu Thr Phe Ser Ile Leu Asn Gln Thr Lys Leu Phe Phe
        115                 120                 125

Thr Ala Phe Phe Thr Tyr Leu Ile Leu Gly Gln Lys Gln Ser Pro Lys
    130                 135                 140

Gln Ile Gly Ala Leu Thr Leu Leu Ile Val Ala Ala Ile Leu Leu Ser
145                 150                 155                 160
```

```
Val Gly Glu Ser Ser Gly Lys Ala Ser Ala Ser Ser Asn Ser Asp Gln
            165                 170                 175

Val Leu Leu Tyr Gly Ile Ile Pro Val Met Ile Ala Ser Val Leu Ser
        180                 185                 190

Gly Leu Ala Ser Ser Leu Cys Gln Trp Ala Ser Gln Val Lys Lys His
            195                 200                 205

Thr Ser Tyr Ile Met Thr Val Glu Met Ser Phe Val Gly Ser Leu Cys
        210                 215                 220

Leu Leu Ala Ser Thr Tyr Lys Ser Pro Asp Gly Glu Ala Ile Gln Lys
225                 230                 235                 240

Tyr Gly Phe Phe His Gly Trp Thr Val Trp Thr Leu Ile Pro Val Val
                245                 250                 255

Met Asn Ala Val Gly Gly Ile Leu Val Gly Leu Val Thr Ala His Ala
            260                 265                 270

Gly Gly Val Arg Lys Gly Phe Ile Val Ser Ala Leu Leu Val Thr
        275                 280                 285

Ala Met Leu Gln Phe Leu Phe Asp Gly Lys Pro Ser Val Tyr Cys
            290                 295                 300

Leu Ala Ala Leu Pro Leu Val Ile Ser Ser Ile Val Ile Tyr Gln Lys
305                 310                 315                 320

Tyr Pro Tyr Val Gly Arg Lys Lys Glu Asp
                325                 330

<210> SEQ ID NO 39
<211> LENGTH: 334
<212> TYPE: PRT
<213> ORGANISM: Physcomitrella patens

<400> SEQUENCE: 39

Met Gly Thr Glu Glu Val Glu Lys Val Gln Gln His Ala Gln His Asp
1               5                   10                  15

Asp Asp Lys Lys Lys Gln Arg Thr Val Ala Ala Leu Cys Met Ala Leu
            20                  25                  30

Leu Thr Ile Gln Tyr Gly Met Gln Pro Leu Ile Ser Lys Arg Phe Thr
        35                  40                  45

Gly Lys Tyr Val Ile Met Thr Ser Ala Val Leu Thr Cys Glu Met Val
    50                  55                  60

Lys Cys Ala Ala Ala Leu Phe Phe Met Ala Arg Asp Gly Thr Leu Trp
65                  70                  75                  80

Lys Leu Pro Lys Glu Trp Ser Phe Val Asp Ser Leu Lys Ala Ser Ala
                85                  90                  95

Ser Pro Ala Ala Ile Tyr Ala Leu Gln Asn Thr Leu Leu Gln Leu Ser
            100                 105                 110

Tyr Arg Asn Leu Asp Ser Leu Thr Phe Ser Leu Leu Asn Gln Thr Lys
        115                 120                 125

Leu Val Phe Thr Ala Val Phe Met Phe Leu Leu Gly Ser Arg Gln
    130                 135                 140

Thr Lys Gln Gln Ile Gly Ala Leu Phe Leu Leu Gly Ala Ala Thr
145                 150                 155                 160

Leu Leu Ser Leu Gly Lys Thr Ala Pro Lys Gln Gly Ile Lys Glu Val
                165                 170                 175

Glu Trp Glu Ser Thr Leu Trp Leu Gly Ile Ile Pro Ile Ile Ser Ala
            180                 185                 190

Ser Val Leu Ser Gly Leu Ala Ser Thr Leu Cys Gln Trp Ala Ala Gln
        195                 200                 205
```

Val Lys Arg Arg Ser Thr Tyr Leu Met Thr Leu Glu Met Ser Thr Tyr
    210                 215                 220

Gly Ser Leu Val Leu Leu Thr Ser Met Trp Trp Ser Pro Asp Gly Val
225                 230                 235                 240

Ser Ile Gln Lys Leu Gly Phe Phe Tyr Gly Trp Ser Leu Leu Thr Phe
            245                 250                 255

Ile Pro Val Cys Leu Asn Ala Phe Gly Gly Ile Leu Val Gly Leu Val
            260                 265                 270

Thr Gln Tyr Ser Gly Gly Ile Lys Lys Gly Phe Val Ile Val Ser Ala
        275                 280                 285

Leu Leu Val Thr Ala Leu Leu Glu Val Ile Val Glu Gly Lys Pro Pro
    290                 295                 300

Ser Ser Tyr Ala Ile Ala Ala Leu Pro Leu Val Val Ser Ser Thr Ile
305                 310                 315                 320

Ile His Gln Asn Tyr Pro Phe Lys Ala Lys Pro Lys Thr Ala
                325                 330

<210> SEQ ID NO 40
<211> LENGTH: 20
<212> TYPE: DNA
<213> ORGANISM: artificial
<220> FEATURE:
<223> OTHER INFORMATION: primer

<400> SEQUENCE: 40
tgagaaaacg acgtccaatg                                              20

<210> SEQ ID NO 41
<211> LENGTH: 20
<212> TYPE: DNA
<213> ORGANISM: artificial
<220> FEATURE:
<223> OTHER INFORMATION: primer

<400> SEQUENCE: 41
taaacccgac aggacagagg                                              20

<210> SEQ ID NO 42
<211> LENGTH: 22
<212> TYPE: DNA
<213> ORGANISM: artificial
<220> FEATURE:
<223> OTHER INFORMATION: primer

<400> SEQUENCE: 42
tggttcacgt agtgggccat cg                                           22

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
taaacccgac aggacagagg                                              20

<210> SEQ ID NO 44
<211> LENGTH: 20
<212> TYPE: DNA
<213> ORGANISM: artificial
<220> FEATURE:

<223> OTHER INFORMATION: primer

<400> SEQUENCE: 44
tgagaaaacg acgtccaatg                    20

<210> SEQ ID NO 45
<211> LENGTH: 23
<212> TYPE: DNA
<213> ORGANISM: artificial
<220> FEATURE:
<223> OTHER INFORMATION: primer

<400> SEQUENCE: 45
atattgacca tcatactcat tgc                23

<210> SEQ ID NO 46
<211> LENGTH: 20
<212> TYPE: DNA
<213> ORGANISM: artificial
<220> FEATURE:
<223> OTHER INFORMATION: primer

<400> SEQUENCE: 46
gcaagaggct ttagctccaa                    20

<210> SEQ ID NO 47
<211> LENGTH: 20
<212> TYPE: DNA
<213> ORGANISM: artificial
<220> FEATURE:
<223> OTHER INFORMATION: primer

<400> SEQUENCE: 47
ttgcccgtaa gatgttttca                    20

<210> SEQ ID NO 48
<211> LENGTH: 20
<212> TYPE: DNA
<213> ORGANISM: artificial
<220> FEATURE:
<223> OTHER INFORMATION: primer

<400> SEQUENCE: 48
gcaagaggct ttagctccaa                    20

<210> SEQ ID NO 49
<211> LENGTH: 34
<212> TYPE: DNA
<213> ORGANISM: artificial
<220> FEATURE:
<223> OTHER INFORMATION: primer

<400> SEQUENCE: 49
gccttttcag aaatggataa atagccttgc ttcc    34

<210> SEQ ID NO 50
<211> LENGTH: 20
<212> TYPE: DNA
<213> ORGANISM: artificial
<220> FEATURE:
<223> OTHER INFORMATION: primer

<400> SEQUENCE: 50
ccttgttgcc tctcgaactc                    20

```
<210> SEQ ID NO 51
<211> LENGTH: 20
<212> TYPE: DNA
<213> ORGANISM: artificial
<220> FEATURE:
<223> OTHER INFORMATION: primer

<400> SEQUENCE: 51
cgcaagctat ggagaagagg                                                    20

<210> SEQ ID NO 52
<211> LENGTH: 21
<212> TYPE: DNA
<213> ORGANISM: artificial
<220> FEATURE:
<223> OTHER INFORMATION: primer

<400> SEQUENCE: 52
cccatttgga cgtgtagaca c                                                  21

<210> SEQ ID NO 53
<211> LENGTH: 20
<212> TYPE: DNA
<213> ORGANISM: artificial
<220> FEATURE:
<223> OTHER INFORMATION: primer

<400> SEQUENCE: 53
cgcaagctat ggagaagagg                                                    20

<210> SEQ ID NO 54
<211> LENGTH: 20
<212> TYPE: DNA
<213> ORGANISM: artificial
<220> FEATURE:
<223> OTHER INFORMATION: primer

<400> SEQUENCE: 54
gggcactcaa caatcatcaa                                                    20

<210> SEQ ID NO 55
<211> LENGTH: 21
<212> TYPE: DNA
<213> ORGANISM: artificial
<220> FEATURE:
<223> OTHER INFORMATION: primer

<400> SEQUENCE: 55
tccactgata aatcccactg c                                                  21

<210> SEQ ID NO 56
<211> LENGTH: 20
<212> TYPE: DNA
<213> ORGANISM: artificial
<220> FEATURE:
<223> OTHER INFORMATION: primer

<400> SEQUENCE: 56
ataacgctgc ggacatctac                                                    20

<210> SEQ ID NO 57
<211> LENGTH: 21
<212> TYPE: DNA
<213> ORGANISM: artificial
<220> FEATURE:
<223> OTHER INFORMATION: primer
```

<400> SEQUENCE: 57
tccactgata aatcccactg c                                          21

<210> SEQ ID NO 58
<211> LENGTH: 20
<212> TYPE: DNA
<213> ORGANISM: artificial
<220> FEATURE:
<223> OTHER INFORMATION: primer

<400> SEQUENCE: 58
ccacgattcg acccaaagtt                                            20

<210> SEQ ID NO 59
<211> LENGTH: 20
<212> TYPE: DNA
<213> ORGANISM: artificial
<220> FEATURE:
<223> OTHER INFORMATION: primer

<400> SEQUENCE: 59
gctccaacac ttgctcttcc                                            20

<210> SEQ ID NO 60
<211> LENGTH: 20
<212> TYPE: DNA
<213> ORGANISM: artificial
<220> FEATURE:
<223> OTHER INFORMATION: primer

<400> SEQUENCE: 60
ccacgattcg acccaaagtt                                            20

<210> SEQ ID NO 61
<211> LENGTH: 22
<212> TYPE: DNA
<213> ORGANISM: artificial
<220> FEATURE:
<223> OTHER INFORMATION: primer

<400> SEQUENCE: 61
tggttcacgt agtgggccat cg                                         22

<210> SEQ ID NO 62
<211> LENGTH: 29
<212> TYPE: DNA
<213> ORGANISM: artificial
<220> FEATURE:
<223> OTHER INFORMATION: primer

<400> SEQUENCE: 62
ccaacttgtc gtatatcatt cgtacagtg                                  29

<210> SEQ ID NO 63
<211> LENGTH: 23
<212> TYPE: DNA
<213> ORGANISM: artificial
<220> FEATURE:
<223> OTHER INFORMATION: primer

<400> SEQUENCE: 63
tggagagatt cgccatgtga cag                                        23

<210> SEQ ID NO 64
<211> LENGTH: 29

```
<212> TYPE: DNA
<213> ORGANISM: artificial
<220> FEATURE:
<223> OTHER INFORMATION: primer

<400> SEQUENCE: 64
ccaacttgtc gtatatcatt cgtacagtg                                    29

<210> SEQ ID NO 65
<211> LENGTH: 30
<212> TYPE: DNA
<213> ORGANISM: artificial
<220> FEATURE:
<223> OTHER INFORMATION: primer

<400> SEQUENCE: 65
caacacgtgg gttaattaag aattcagtac                                   30

<210> SEQ ID NO 66
<211> LENGTH: 20
<212> TYPE: DNA
<213> ORGANISM: artificial
<220> FEATURE:
<223> OTHER INFORMATION: primer

<400> SEQUENCE: 66
tgcatgacgg ctctaagaca                                              20

<210> SEQ ID NO 67
<211> LENGTH: 20
<212> TYPE: DNA
<213> ORGANISM: artificial
<220> FEATURE:
<223> OTHER INFORMATION: primer

<400> SEQUENCE: 67
tcgagctctg gaactccaat                                              20

<210> SEQ ID NO 68
<211> LENGTH: 22
<212> TYPE: DNA
<213> ORGANISM: artificial
<220> FEATURE:
<223> OTHER INFORMATION: primer

<400> SEQUENCE: 68
tggttcacgt agtgggccat cg                                           22

<210> SEQ ID NO 69
<211> LENGTH: 20
<212> TYPE: DNA
<213> ORGANISM: artificial
<220> FEATURE:
<223> OTHER INFORMATION: primer

<400> SEQUENCE: 69
tcgagctctg gaactccaat                                              20

<210> SEQ ID NO 70
<211> LENGTH: 21
<212> TYPE: DNA
<213> ORGANISM: artificial
<220> FEATURE:
<223> OTHER INFORMATION: primer

<400> SEQUENCE: 70
```

```
ctaccggatc gggtaagtct c                                              21

<210> SEQ ID NO 71
<211> LENGTH: 21
<212> TYPE: DNA
<213> ORGANISM: artificial
<220> FEATURE:
<223> OTHER INFORMATION: primer

<400> SEQUENCE: 71
gctacaagat tctcccaagc c                                              21

<210> SEQ ID NO 72
<211> LENGTH: 21
<212> TYPE: DNA
<213> ORGANISM: artificial
<220> FEATURE:
<223> OTHER INFORMATION: primer

<400> SEQUENCE: 72
ctaccggatc gggtaagtct c                                              21

<210> SEQ ID NO 73
<211> LENGTH: 22
<212> TYPE: DNA
<213> ORGANISM: artificial
<220> FEATURE:
<223> OTHER INFORMATION: primer

<400> SEQUENCE: 73
tggttcacgt agtgggccat cg                                             22

<210> SEQ ID NO 74
<211> LENGTH: 20
<212> TYPE: DNA
<213> ORGANISM: artificial
<220> FEATURE:
<223> OTHER INFORMATION: primer

<400> SEQUENCE: 74
gtatgggccc taaggttttg                                                20

<210> SEQ ID NO 75
<211> LENGTH: 20
<212> TYPE: DNA
<213> ORGANISM: artificial
<220> FEATURE:
<223> OTHER INFORMATION: primer

<400> SEQUENCE: 75
atacgatgat ggcggttttc                                                20

<210> SEQ ID NO 76
<211> LENGTH: 19
<212> TYPE: DNA
<213> ORGANISM: artificial
<220> FEATURE:
<223> OTHER INFORMATION: primer

<400> SEQUENCE: 76
ggctaacgga gcaaagagt                                                 19

<210> SEQ ID NO 77
<211> LENGTH: 19
<212> TYPE: DNA
<213> ORGANISM: artificial
```

```
<220> FEATURE:
<223> OTHER INFORMATION: primer

<400> SEQUENCE: 77
cagcgtttgg agatcagag                                              19

<210> SEQ ID NO 78
<211> LENGTH: 20
<212> TYPE: DNA
<213> ORGANISM: artificial
<220> FEATURE:
<223> OTHER INFORMATION: primer

<400> SEQUENCE: 78
gctctgattc tcatggcaag                                             20

<210> SEQ ID NO 79
<211> LENGTH: 23
<212> TYPE: DNA
<213> ORGANISM: artificial
<220> FEATURE:
<223> OTHER INFORMATION: primer

<400> SEQUENCE: 79
tgctgtgaaa aagatttcg tct                                          23

<210> SEQ ID NO 80
<211> LENGTH: 20
<212> TYPE: DNA
<213> ORGANISM: artificial
<220> FEATURE:
<223> OTHER INFORMATION: primer

<400> SEQUENCE: 80
tacaacgagc ttcgtgttgc                                             20

<210> SEQ ID NO 81
<211> LENGTH: 20
<212> TYPE: DNA
<213> ORGANISM: artificial
<220> FEATURE:
<223> OTHER INFORMATION: primer

<400> SEQUENCE: 81
tccacatctg ttggaaggtg                                             20

<210> SEQ ID NO 82
<211> LENGTH: 25
<212> TYPE: DNA
<213> ORGANISM: artificial
<220> FEATURE:
<223> OTHER INFORMATION: primer

<400> SEQUENCE: 82
ttccatattg ctcacacttc agtac                                       25

<210> SEQ ID NO 83
<211> LENGTH: 20
<212> TYPE: DNA
<213> ORGANISM: artificial
<220> FEATURE:
<223> OTHER INFORMATION: primer

<400> SEQUENCE: 83
aaacagatgc ccagaaatcg                                             20
```

<210> SEQ ID NO 84
<211> LENGTH: 26
<212> TYPE: DNA
<213> ORGANISM: artificial
<220> FEATURE:
<223> OTHER INFORMATION: primer

<400> SEQUENCE: 84
cataaccttg ttatattaat ttgcca                                    26

<210> SEQ ID NO 85
<211> LENGTH: 20
<212> TYPE: DNA
<213> ORGANISM: artificial
<220> FEATURE:
<223> OTHER INFORMATION: primer

<400> SEQUENCE: 85
aggccggagt tctgtaaatg                                            20

<210> SEQ ID NO 86
<211> LENGTH: 27
<212> TYPE: DNA
<213> ORGANISM: artificial
<220> FEATURE:
<223> OTHER INFORMATION: primer

<400> SEQUENCE: 86
gagccttaca acgctactct gtctgtc                                    27

<210> SEQ ID NO 87
<211> LENGTH: 27
<212> TYPE: DNA
<213> ORGANISM: artificial
<220> FEATURE:
<223> OTHER INFORMATION: primer

<400> SEQUENCE: 87
acaccagaca tagtagcaga aatcaag                                    27

<210> SEQ ID NO 88
<211> LENGTH: 19
<212> TYPE: DNA
<213> ORGANISM: artificial
<220> FEATURE:
<223> OTHER INFORMATION: primer

<400> SEQUENCE: 88
ctactcgcag ctaaaacgc                                             19

<210> SEQ ID NO 89
<211> LENGTH: 18
<212> TYPE: DNA
<213> ORGANISM: artificial
<220> FEATURE:
<223> OTHER INFORMATION: primer

<400> SEQUENCE: 89
gccgaaagaa tcaggaca                                              18

<210> SEQ ID NO 90
<211> LENGTH: 18
<212> TYPE: DNA
<213> ORGANISM: artificial
<220> FEATURE:
<223> OTHER INFORMATION: primer -continued

```
<400> SEQUENCE: 90
gagctctccg atgcaaat                                                18

<210> SEQ ID NO 91
<211> LENGTH: 18
<212> TYPE: DNA
<213> ORGANISM: artificial
<220> FEATURE:
<223> OTHER INFORMATION: primer

<400> SEQUENCE: 91
gaaaaaggcc atagggt                                                 18

<210> SEQ ID NO 92
<211> LENGTH: 20
<212> TYPE: DNA
<213> ORGANISM: artificial
<220> FEATURE:
<223> OTHER INFORMATION: primer

<400> SEQUENCE: 92
cttggaacca atctgctctc                                              20

<210> SEQ ID NO 93
<211> LENGTH: 18
<212> TYPE: DNA
<213> ORGANISM: artificial
<220> FEATURE:
<223> OTHER INFORMATION: primer

<400> SEQUENCE: 93
atcatcgacg gcaagaac                                                18

<210> SEQ ID NO 94
<211> LENGTH: 19
<212> TYPE: DNA
<213> ORGANISM: artificial
<220> FEATURE:
<223> OTHER INFORMATION: primer

<400> SEQUENCE: 94
acgaccctct agcgattct                                               19

<210> SEQ ID NO 95
<211> LENGTH: 18
<212> TYPE: DNA
<213> ORGANISM: artificial
<220> FEATURE:
<223> OTHER INFORMATION: primer

<400> SEQUENCE: 95
cggcagtatt gatgcgta                                                18

<210> SEQ ID NO 96
<211> LENGTH: 19
<212> TYPE: DNA
<213> ORGANISM: artificial
<220> FEATURE:
<223> OTHER INFORMATION: primer

<400> SEQUENCE: 96
ggctaacgga gcaaagagt                                               19

<210> SEQ ID NO 97
```

```
<211> LENGTH: 19
<212> TYPE: DNA
<213> ORGANISM: artificial
<220> FEATURE:
<223> OTHER INFORMATION: primer

<400> SEQUENCE: 97
cagcgtttgg agatcagag                                               19

<210> SEQ ID NO 98
<211> LENGTH: 24
<212> TYPE: DNA
<213> ORGANISM: artificial
<220> FEATURE:
<223> OTHER INFORMATION: primer

<400> SEQUENCE: 98
acgtaccaag accagcagac tacc                                         24

<210> SEQ ID NO 99
<211> LENGTH: 22
<212> TYPE: DNA
<213> ORGANISM: artificial
<220> FEATURE:
<223> OTHER INFORMATION: primer

<400> SEQUENCE: 99
tgcagtcctt ggtgagactt cg                                           22

<210> SEQ ID NO 100
<211> LENGTH: 22
<212> TYPE: DNA
<213> ORGANISM: artificial
<220> FEATURE:
<223> OTHER INFORMATION: primer

<400> SEQUENCE: 100
tggactcgaa ttgtggcagg tg                                           22

<210> SEQ ID NO 101
<211> LENGTH: 24
<212> TYPE: DNA
<213> ORGANISM: artificial
<220> FEATURE:
<223> OTHER INFORMATION: primer

<400> SEQUENCE: 101
tgccaacttc ttggcatagt ctgg                                         24

<210> SEQ ID NO 102
<211> LENGTH: 24
<212> TYPE: DNA
<213> ORGANISM: artificial
<220> FEATURE:
<223> OTHER INFORMATION: primer

<400> SEQUENCE: 102
tctgcagatg gtctcaagag ctac                                         24

<210> SEQ ID NO 103
<211> LENGTH: 23
<212> TYPE: DNA
<213> ORGANISM: artificial
<220> FEATURE:
<223> OTHER INFORMATION: primer

<400> SEQUENCE: 103
```
ctcggctttc tcaatcagtt ccg                                   23

<210> SEQ ID NO 104
<211> LENGTH: 28
<212> TYPE: DNA
<213> ORGANISM: artificial
<220> FEATURE:
<223> OTHER INFORMATION: primer

<400> SEQUENCE: 104
cggagctcgg caggcttcat gattgatt                              28

<210> SEQ ID NO 105
<211> LENGTH: 28
<212> TYPE: DNA
<213> ORGANISM: artificial
<220> FEATURE:
<223> OTHER INFORMATION: primer

<400> SEQUENCE: 105
cggagctctc aatgggttga tttgcgta                              28

<210> SEQ ID NO 106
<211> LENGTH: 30
<212> TYPE: DNA
<213> ORGANISM: artificial
<220> FEATURE:
<223> OTHER INFORMATION: primer

<400> SEQUENCE: 106
cgcggctagc cggccgttga ttttgactat                            30

<210> SEQ ID NO 107
<211> LENGTH: 31
<212> TYPE: DNA
<213> ORGANISM: artificial
<220> FEATURE:
<223> OTHER INFORMATION: primer

<400> SEQUENCE: 107
cgcggctagc caccttcttc ttcttcttgt c                          31

<210> SEQ ID NO 108
<211> LENGTH: 28
<212> TYPE: DNA
<213> ORGANISM: artificial
<220> FEATURE:
<223> OTHER INFORMATION: primer

<400> SEQUENCE: 108
cataggtacc tgcgacggct aacggagc                              28

<210> SEQ ID NO 109
<211> LENGTH: 34
<212> TYPE: DNA
<213> ORGANISM: artificial
<220> FEATURE:
<223> OTHER INFORMATION: primer

<400> SEQUENCE: 109
gtctgaattc ttacaccttc ttcttcttct tgtc                       34

<210> SEQ ID NO 110
<211> LENGTH: 28
<212> TYPE: DNA

```
<213> ORGANISM: artificial
<220> FEATURE:
<223> OTHER INFORMATION: primer

<400> SEQUENCE: 110
aaaaagcagg ctttatggga ttgacctc                                          28

<210> SEQ ID NO 111
<211> LENGTH: 34
<212> TYPE: DNA
<213> ORGANISM: artificial
<220> FEATURE:
<223> OTHER INFORMATION: primer

<400> SEQUENCE: 111
agaaagctgg gttctaactc gagtttattt tttg                                   34

<210> SEQ ID NO 112
<211> LENGTH: 29
<212> TYPE: DNA
<213> ORGANISM: artificial
<220> FEATURE:
<223> OTHER INFORMATION: primer

<400> SEQUENCE: 112
ggggacaagt ttgtacaaaa aagcaggct                                         29

<210> SEQ ID NO 113
<211> LENGTH: 29
<212> TYPE: DNA
<213> ORGANISM: artificial
<220> FEATURE:
<223> OTHER INFORMATION: primer

<400> SEQUENCE: 113
ggggaccact ttgtacaaga aagctgggt                                         29

<210> SEQ ID NO 114
<211> LENGTH: 40
<212> TYPE: DNA
<213> ORGANISM: artificial
<220> FEATURE:
<223> OTHER INFORMATION: primer

<400> SEQUENCE: 114
aaaaagcagg cttcaccatg gcgacggcta acggagcaaa                             40

<210> SEQ ID NO 115
<211> LENGTH: 37
<212> TYPE: DNA
<213> ORGANISM: artificial
<220> FEATURE:
<223> OTHER INFORMATION: primer

<400> SEQUENCE: 115
agaaagctgg gtgttacacc ttcttcttct tcttgtc                                37

<210> SEQ ID NO 116
<211> LENGTH: 37
<212> TYPE: DNA
<213> ORGANISM: artificial
<220> FEATURE:
<223> OTHER INFORMATION: primer

<400> SEQUENCE: 116
agaaagctgg gtgttagtca atgtatgggt atttctg                                37
```

```
<210> SEQ ID NO 117
<211> LENGTH: 34
<212> TYPE: DNA
<213> ORGANISM: artificial
<220> FEATURE:
<223> OTHER INFORMATION: primer

<400> SEQUENCE: 117
agaaagctgg gtgcaccttc ttcttcttct tgtc                                    34

<210> SEQ ID NO 118
<211> LENGTH: 30
<212> TYPE: DNA
<213> ORGANISM: artificial
<220> FEATURE:
<223> OTHER INFORMATION: primer

<400> SEQUENCE: 118
attaatatgg tgagcaaggg cgaggagctg                                         30

<210> SEQ ID NO 119
<211> LENGTH: 29
<212> TYPE: DNA
<213> ORGANISM: artificial
<220> FEATURE:
<223> OTHER INFORMATION: primer

<400> SEQUENCE: 119
attaatcttg tacagctcgt ccatgccga                                          29

<210> SEQ ID NO 120
<211> LENGTH: 35
<212> TYPE: DNA
<213> ORGANISM: artificial
<220> FEATURE:
<223> OTHER INFORMATION: primer

<400> SEQUENCE: 120
cagaattctt agtcaatgta tgggtatttc tggta                                   35
```

DISRUPTION OF ROCK1 GENE LEADS TO PLANTS WITH IMPROVED TRAITS

CROSS REFERENCE TO RELATED APPLICATIONS

This U.S. Application is a National Stage Entry of PCT/EP2015/076008 which claims priority to European Application No.: 14192882.0 filed Nov. 12, 2014, entitled "DISRUPTION OF ROCK1 GENE LEADS TO PLANTS WITH IMPROVED TRAITS" the entirety of which is incorporated herein by reference.

REFERENCE TO A SEQUENCE LISTING SUBMITTED IN COMPUTER READABLE FORM

This application includes a "Sequence Listing" which is provided in computer readable form (CRF). The file "3975-159_ST25.txt" was created Aug. 10, 2018, and is 117,649 bytes, which is herein incorporated by reference in its entirety.

In order to be able to supply a continuously growing population with food and other plant-derived products, people have always been interested in improving the productivity in agriculture.

The productivity of a plant can be influenced in various different ways, e.g. by improving plant growth characteristics or by delaying leaf senescence. There are many mechanisms and pathways known which are involved in plant growth and development.

Cytokinin is a plant hormone that plays positive and negative regulatory roles in many aspects of plant growth and development. It stimulates the formation and activity of shoot meristems, is able to establish sink tissues, retard leaf senescence, inhibits root growth and branching, and plays a role in seed germination and stress responses. Analysis of cytokinin-deficient plants has shown that cytokinin plays opposite roles in shoot and root meristems and suggests that the hormone has an essential function in quantitative control of organ growth.

It has been shown that cytokinin oxidases/dehydrogenases (CKX) are an important factor to regulate the homeostasis of the plant hormone cytokinin. The genome of Arabidopsis encodes seven CKX genes, which have distinct expression domains. Recently it was shown that in a rice plant inhibition of the function of a particular CKX gene, the rice orthologue to CKX3 of *Arabidopsis thaliana*, has led to an increase in particle-bearing number of said rice plant (see US 2006/0123507 A1). Since modern crop plants are the result of recent genome-hybridization events it is beneficial to identify genes that are controlling the activity of a whole group of gene products at once.

The economic focus can lie on different parts of the plant thus defining the yield-related traits. In the case of ornamental plants, the number of flowers can be a central trait. The same is true in the case where flower organs are the economically used part. Furthermore, one of the parameters influencing the seed yield is the number of flowers. Additionally, the production of biomass is influenced by the growth rate of the stem.

It is an object of the present invention to provide means and methods suitable to provide plants with improved yield-related traits.

This object is achieved by the present invention as set out in detail below.

The present invention provides means and methods for improving a trait in a plant, e.g. improving yield-related traits in a plant, the method comprising disruption of endogenous ROCK1 gene in a plant cell, wherein said disruption inhibits expression and/or activity of a product of said endogenous ROCK1 gene compared to a corresponding control plant cell lacking such a disruption.

In a first aspect, the present invention is directed to a method for improving a trait in a plant, the method comprising disruption of endogenous ROCK1 gene in a plant cell, wherein said disruption inhibits expression and/or activity of a product of said endogenous ROCK1 gene compared to a corresponding control plant cell lacking such a disruption.

In a second aspect, the invention refers to a plant cell or a plant obtainable or obtained by the method of the present invention or to progeny thereof, wherein said progeny comprises or consists of plant cells with a disruption in endogenous ROCK1 gene.

In a third aspect, the present invention is directed to the use of the method of the present invention for production of a plant with improved yield-related traits compared to a plant which lacks a disruption in its endogenous ROCK1 gene.

In a forth aspect, the present invention provides an isolated ROCK1 protein and an isolated nucleic acid encoding such ROCK1 protein.

It has surprisingly been found that in a plant disruption of endogenous ROCK1 gene leads to plants with yield-related traits that are improved compared to a plant lacking such disruption. It has been shown that disruption of endogenous ROCK1 gene leads to plants with a significant increase in yield-related traits like e.g. total number of flowers, total number of siliques, and/or shoot growth compared to wild type plants or plants lacking such a disruption in its endogenous ROCK1 gene.

Thus, the present invention provides a method for improving a trait in a plant, wherein the method comprises the step of disrupting endogenous ROCK1 gene in a plant cell, wherein said disruption inhibits expression and/or activity of a product of said endogenous ROCK1 gene compared to a corresponding plant cell lacking such a disruption, wherein the endogenous ROCK1 gene comprises or consists of:
(a) a nucleic acid encoding a ROCK1 protein comprising or consisting of the amino acid sequence of SEQ ID NO: 1 or 2 or an orthologue thereof;
(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence with SEQ ID NO: 1 or 2;
(c) a nucleic acid comprising or consisting of one of the nucleic acid sequences with SEQ ID NO: 4, 5, 6, 7 and/or 8;
(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence with one of SEQ ID NO: 4, 5, 6, 7 and/or 8; or
(e) a nucleic acid hybridizing under stringent conditions to one of the nucleic acid sequences defined under (a), (b), (c), and/or (d).

The method of the invention can comprise further steps. Preferably the method of the invention comprises the steps of introducing into the genome of a plant cell a disruption of endogenous ROCK1 gene, and regenerating a plant with such an altered genome from said plant cell.

The endogenous ROCK1 gene disrupted in the method of the invention encodes for a ROCK1 protein, wherein said ROCK1 protein is a member of the nucleotide sugar transporter (NST) family of proteins and exhibits essentially the same function as ROCK1 protein with SEQ ID NO: 1. The ROCK1 protein with SEQ ID NO: 1 is a member of NST family with UDP-GlcNAc and UDP-GalNAc being main substrates. Preferably, the endogenous ROCK1 gene disrupted in the method of the invention encodes for a ROCK1 protein comprising the amino acid motif GGILVGLVT with SEQ ID NO. 3. In the method of the invention, the ROCK1 protein with SEQ ID NO. 1 or an orthologue thereof preferably comprises the amino acid sequence GGILVGLVT with SEQ ID NO. 3.

In the method of the invention, one, more than one or all disruptions can be introduced by structural disruption, T-DNA insertion, antisense polynucleotide gene suppression, double stranded RNA induced gene silencing, ribozyme techniques, genomic disruption, tilling, transcription activator-like effector nucleases (TALENs), CRISPR/Cas, designer zinc finger nucleases (ZFNs), homing meganucleases and/or homologous recombination.

Preferably, one, more than one or all disruptions in endogenous ROCK1 gene are homozygous disruptions.

In the method of the invention, the endogenous ROCK1 gene preferably comprises or consists of:
(a) a nucleic acid encoding a ROCK1 protein comprising or consisting of one of the amino acid sequences with SEQ ID NO: 1, 2, and/or 9 to 39;
(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence of one of SEQ ID NO: 1, 2, and/or 9 to 39;
(c) a nucleic acid comprising or consisting of one of the nucleic acid sequences with SEQ ID NO: 4, 5, 6, 7 and/or 8;
(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence of one of SEQ ID NO: 4, 5, 6, 7 and/or 8; or
(e) a nucleic acid hybridizing under stringent conditions to one of the nucleic acid sequences defined under (a), (b), (c), and/or (d).

The method of the invention allows for improvement of a trait in a plant. Preferably, the trait improved is a yield-related trait like e.g. number of flowers, number of siliques, and/or shoot growth.

The present invention also provides for a plant cell obtainable or obtained by the method of the invention or progeny thereof comprising a disruption in its endogenous ROCK1 gene, wherein the endogenous ROCK1 gene comprises or consists of:
(a) a nucleic acid encoding a ROCK1 protein comprising or consisting of the amino acid sequence of SEQ ID NO: 1 or 2 or an orthologue thereof;
(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence with SEQ ID NO: 1 or 2;
(c) a nucleic acid comprising or consisting of one of the nucleic acid sequences with SEQ ID NO: 4, 5, 6, 7 and/or 8;
(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence of one of SEQ ID NO: 4, 5, 6, 7 and/or 8; or
(e) a nucleic acid hybridizing under stringent conditions to one of the nucleic acid sequences defined under (a), (b), (c), and/or (d).

The present invention is also directed to a plant obtainable or obtained by the method of the invention or progeny thereof comprising a disruption in endogenous ROCK1 gene. The endogenous ROCK1 gene comprises or consists of:
(a) a nucleic acid encoding a ROCK1 protein comprising or consisting of the amino acid sequence of SEQ ID NO: 1 or 2 or an orthologue thereof;
(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence with SEQ ID NO: 1 or 2;
(c) a nucleic acid comprising or consisting of one of the nucleic acid sequences with SEQ ID NO: 4, 5, 6, 7 and/or 8;
(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence with one of SEQ ID NO: 4, 5, 6, 7 and/or 8; or
(e) a nucleic acid hybridizing under stringent conditions to one of the nucleic acid sequences defined under (a), (b), (c), and/or (d).

The progeny of the plant of the present invention comprises mature plants, seeds, tubers, beets/swollen tap roots, fruits, shoots, seedlings and/or parts thereof.

The plant of the present invention can be a monocotyledonous, a dicotyledonous plant, a moss or an algae.

Preferably, the plant or the plant cell of the present invention is selected from the family of Brassicaceae, Rosaceae, Fabaceae, Poaceae, Vitaceae, Solanaceae, Salicaceae, Malvaceae, Pinaceae, Funariaceae, Rutaceae, Rubiacea, Musaceae and/or Selaginellaceae, more preferably of Brassicaceae, Poaceae, Rosaceae, Solanaceae, Malvaceae and/or Fabaceae.

The method of the present invention can be used for production of a plant with increased yield-related traits compared to a plant which lacks a disruption in its endogenous ROCK1 gene.

Furthermore, the present invention is directed to an isolated nucleic acid encoding a ROCK1 protein comprising or consisting of an amino acid sequence with one of SEQ ID NO: 1, 2, and/or 9 to 39 and to an isolated ROCK1 protein comprising or consisting of an amino acid sequence with one of SEQ ID NO: 1, 2, and/or 9 to 39.

Unless defined otherwise, all technical and scientific terms used herein have the same meaning as commonly understood by one of ordinary skill in the art to which the invention pertains. In describing and claiming the present invention, the following terminology will be used in accordance with the definitions set out below.

As used in this specification and appended claims, the singular forms "a", "an" and "the" include singular and plural referents unless the content clearly dictates otherwise. Thus, for example, reference to "a cell" includes one cell and a combination of two or more cells, and the like.

In the method of the present invention a trait of a plant is improved. The trait improved may be one or more yield-related traits. Yield-related traits are known to the person skilled in the art; however, for the purpose of the present invention yield-related traits comprise number of flowers, number of siliques, seed yield, stem growth, shoot growth and/or other seed-related traits.

The term "plant" refers generically to any of: whole plants, plant parts or organs (e. g. leaves, stems, roots, etc.), shoot vegetative organs/structures (e. g. leaves, stems and tubers), roots, flowers and floral organs/structures (e. g. bracts, sepals, petals, stamens, carpels, anthers and ovules), seed (including embryo, endosperm, and seed coat), fruit (the mature ovary), plant tissue (e. g. vascular tissue, ground tissue, and the like), tissue culture callus, and plant cells (e. g. guard cells, egg cells, trichomes and the like), and progeny of same. The term "plant" generally means all those organisms which are capable of photosynthesis. Included as plant within the scope of the invention are all genera and species of the higher and lower plants of the plant kingdom. Mature plants means plants at any developmental stage beyond the seedling. Seedling means a young immature plant in an early developmental stage. The plants of the invention may be annual, perennial, monocotyledonous and/or dicotyledonous or algae or moss plants. In particular, the plants of the invention can be plants of the families Brassicaceae, Rosaceae, Fabaceae, Poaceae, Vitaceae, Solanaceae, Salicaceae, Malvaceae, Pinaceae, Funariaceae, Rutaceae, Rubiacea, Musaceae and/or Selaginellaceae, preferably plants of the families Brassicaceae, Fabaceae, Rosaceae, Solanaceae, Malvaceae, Salicaceae and/or Poaceae, most preferably *Arabidopsis thaliana, Brassica napus, Brassica rapa, Brassica oleracea, Triticum aestivum, Hordeum vulgare, Zea mays, Oryza sativa, Nicotiana* spec., *Gossypium* spec., *Populus* spec., *Salix* spec and/or *Glycine max*.

Plant cell, as used herein, further includes, without limitation, cells obtained from or found in a plant or a part thereof: seeds, cultures, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

The term "progeny" as used herein refers to a product or part of a plant or plant cell of the invention, wherein said product or part comprises a disruption of an endogenous ROCK1 gene and is suitable for or is capable of producing or regenerating a plant or plant cell of the invention. Progeny of a plant cell of the invention can be e.g. a plant cell derived by cell division from a plant cell of the invention or a plant regenerated from a plant cell of the invention. Progeny of a plant of the invention is e.g. mature plants, seeds, tubers, beets/swollen tap roots, fruits, shoots, seedlings and/or parts thereof.

The present invention refers to a plant obtainable or obtained by the method of the invention. The plant of the invention may be a transgenic plant. The term "transgenic" refers to a plant that has incorporated nucleic acid sequences, including but not limited to genes, polynucleotides, DNA, RNA, etc., and/or alterations thereto (e.g. mutations, point mutations or the like), which have been introduced into a plant compared to a non-introduced plant by processes which are not essentially biological processes for the production of plants. Thus, the term "transgenic plant" encompasses not only plants comprising non-endogenous nucleic acids, but explicitly refers also to plants that bear mutations in an endogenous gene, e.g. point mutations, which have been introduced into said transgenic plant compared to a control plant by processes which are not essentially biological processes for the production of plants.

In the method of the invention a trait is improved in a plant by disruption of endogenous ROCK1 gene.

The term "gene" or "gene sequence" is used broadly to refer to any nucleic acid associated with a biological function. Genes typically include coding sequences and/or the regulatory sequences required for expression of such coding sequences. The term "gene" applies to a specific genomic sequence, as well as to a cDNA or an mRNA encoded by that genomic sequence. Genes also include non-expressed nucleic acid segments that, for example, form recognition or target sequences for other molecules like e.g. nucleic acids and/or proteins. Non-expressed regulatory sequences include promoters and enhancers, to which regulatory proteins such as transcription factors bind, resulting in transcription of adjacent or nearby sequences.

The term "endogenous" relates to any gene or nucleic acid sequence that is already present in a given wild type cell or organism like e.g. a plant. The term "exogenous" relates to any gene or nucleic acid sequences that is not endogenous.

The ROCK1 gene is first described in *Arabidopsis thaliana* and encodes for a ROCK1 protein, also called Repressor of Cytokinin Deficiency 1 (ROCK1). ROCK1 protein is a member of the structural family of nucleotide sugar transporters (NST). ROCK1 is an ER (endoplasmatic reticulum)-resident protein with multiple transmembrane domains and with a C-terminal di-lysine motif which is thought to control exact localisation of the protein.

ROCK1 protein functions as a NST transporting UDP-GalNAc and UDP-GlcNAc as main substrates.

There are tests available to the skilled person which allow testing whether a given protein may function as NST and determining what are the main substrates. A test system commonly used is described in Gerardy-Schahn et al (2001) Nucleotide sugar transporters: biological and functional aspects; *Biochimie* 83(8): 775-782 and Ashikov et al (2005) The human solute carrier gene SLC35B4 encodes a bifunctional nucleotide sugar transporter with specificity for UDP-xylose and UDP-N-acetylglucosamine. *J. Biol. Chem.* 280 (29): 27230-27235. It is a heterologous test system, wherein the protein of interest is introduced into a test organism, e.g. *Saccharomyces cerevisiae*, and transport activity is tested in vitro with radiolabeled nucleotide sugars.

Such a test system is suitable to determine whether a given nucleic acid encodes for a protein which represents an orthologue to ROCK1 with SEQ ID NO: 1 and exhibits essentially the same function as ROCK1 protein of *Arabidopsis thaliana* with SEQ ID NO: 1. A ROCK1 protein exhibits essentially the same function as the ROCK1 protein with SEQ ID NO: 1, if said protein is an NST transporting UDP-GalNAc and UDP-GlcNAc when measured in above mentioned biochemical in vitro test of Gerardy-Schahn et al or Ashikov et al.

The ROCK1 protein of *Arabidopsis thaliana* exists in two alternatively spliced forms, whereas the two splice forms differ in the length of their C-terminal part. As used herein and if not denoted otherwise, the term "ROCK1" refers to both spliced forms; however, the splice form of ROCK1 protein with SEQ ID NO. 1 is preferred. The ROCK1 protein of *Arabidopsis thaliana* comprises an amino acid sequence of SEQ ID NO: 1 for the spliced form denoted Atg65000.1 and of SEQ ID NO 2 for the spliced form denoted At5g65000.2. The genomic sequence of the ROCK1 gene of *Arabidopsis thaliana* comprises the nucleic acid sequence of SEQ ID NO: 4, the coding sequence of ROCK1 gene of *Arabidopsis thaliana* comprises the nucleic acid sequence of SEQ ID NO: 5 for ROCK1 protein with SEQ ID NO. 1 (At5g65000.1) and SEQ ID NO: 6 for ROCK1 protein with SEQ ID NO. 2 (At5g65000.2) and the cDNA of the ROCK1 gene of *Arabidopsis thaliana* comprises the nucleic acid sequence with SEQ ID NO: 7 for ROCK1 protein with SEQ ID NO. 1 (At5g65000.1) and SEQ ID NO: 8 for ROCK1 protein with SEQ ID NO. 2 (At5g65000.2).

The endogenous ROCK1 gene to be disrupted in the method of the invention may comprise or consist of:
(a) a nucleic acid encoding a ROCK1 protein comprising or consisting of the amino acid sequence of SEQ ID NO: 1 or 2 or an orthologue thereof;
(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence with SEQ ID NO: 1 or 2;
(c) a nucleic acid comprising or consisting of one of the nucleic acid sequences with SEQ ID NO: 4, 5, 6, 7 and/or 8;
(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence with one of SEQ ID NO: 4, 5, 6, 7 and/or 8; or
(e) a nucleic acid hybridizing under stringent conditions to one of the nucleic acid sequences defined under (a), (b), (c), and/or (d).

The term "nucleic acid" or "polynucleotide" is generally used in its art-recognized meaning to refer to a ribose nucleic acid (RNA) or deoxyribose nucleic acid (DNA) polymer, or analogue thereof, e. g., a nucleotide polymer comprising modifications of the nucleotides, a peptide nucleic acid, or the like. In certain applications, the nucleic acid can be a polymer that includes multiple monomer types, e. g., both RNA and DNA subunits. A nucleic acid can be e.g. a chromosome or chromosomal segment, a vector (e. g., an expression vector), an expression cassette, a naked DNA or RNA polymer, the product of a polymerase chain reaction (PCR), an oligonucleotide, a probe, combinations thereof, etc. A nucleic acid can be e.g. single-stranded and/or double-stranded. Unless otherwise indicated, a particular nucleic acid sequence of the invention optionally comprises or encodes complementary sequences, in addition to any sequence explicitly indicated.

The term "polynucleotide sequence", "nucleic acid sequence", "nucleic acid" or "nucleotide sequence" refers to a contiguous sequence of nucleotides in a single nucleic acid or to a representation, e. g., a character string, thereof. That is, a "polynucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g. the complementary nucleic acid) can be determined.

The term "subsequence" or "fragment" is any portion of an entire sequence.

The term "orthologue" as used herein refers to a gene from a second species which shows highest similarity, i.e. highest sequence identity, to the specified gene of a first species (e.g. of *Arabidopsis thaliana*) and which encodes for a protein exhibiting essentially the same function as the protein encoded by the specified gene of the first species because both genes originated from a common ancestor. Since during evolution of plants gene or whole genome duplication events occurred, the skilled person is well aware of the fact that a given plant species may comprise more than one orthologuous gene or protein. Thus, a given plant species may comprise multiple paralogous genes wherein said paralogous genes may encode for orthologous proteins which differ in sequence.

The term "orthologue" may denote an endogenous gene encoding for a protein having essentially the same function and comprising a sequence (polypeptide or nucleic acid) with at least 55%, at least 65%, at least 69%, at least 75%, or at least 90% sequence identity to a given sequence the respective orthologue refers to, e.g. over the whole sequence length.

In particular the term "orthologue" as used herein denotes an endogenous ROCK1 gene, which is derived from a species different from *Arabidopsis thaliana*, encoding for a protein with essentially the same function as ROCK1 protein of *Arabidopsis thaliana* with SEQ ID NO. 1 and comprising an amino acid sequence with at least 55%, at least 65%, at least 69%, at least 75%, or at least 90% sequence identity to the ROCK1 protein of *Arabidopsis thaliana* with SEQ ID NO. 1 over the whole sequence length. Preferably, the orthologuous ROCK1 gene encodes for a ROCK1 protein which has the amino acid motif GGILVGLVT with SEQ ID NO. 3 in common with ROCK1 protein of *Arabidopsis thaliana* with SEQ ID NO. 1.

The skilled person can easily and rapidly identify the respective orthologous gene in a given species based on the information provided herewith for ROCK1 gene of *Arabidopsis thaliana*. There are numerous techniques available which are applied routinely by the person skilled in the art in order to successfully identify orthologous genes. This can be done as follows: Use the ROCK1 protein sequence as query and perform a global BLASTP search (Altschul, S. F., Gish, W., Miller, W., Myers, E. W. and Lipman, D. J. (1990) Basic local alignment search tool. J Mol Biol, 215, 403-410) against the database containing the predicted protein sequences of a given species. The obtained sequences with the highest scores are aligned to the ROCK1 protein sequence using Clustal Omega to determine the identity between the protein sequences (Sievers, F., Wilm, A., Dineen, D., Gibson, T. J., Karplus, K., Li, W., Lopez, R., McWilliam, H., Remmert, M., Soding, J., Thompson, J. D. & Higgins, D. G. (2011) Fast, scalable generation of high-quality protein multiple sequence alignments using Clustal Omega. Mol Syst Biol, 7, 539). The proteins showing a sequence identity of at least 55%, at least 65%, at least 69%, at least 75%, or at least 90% with the ROCK1 protein sequence are defined as proteins orthologous to ROCK1.

The orthologue as used herein can refer to an endogenous gene, which is derived from a species different from *Arabidopsis thaliana*, encoding for an orthologous ROCK1 protein with essentially the same function as ROCK1 protein of *Arabidopsis thaliana* with SEQ ID NO. 1. Preferably, the orthologous protein comprises an amino acid sequence with at least 55%, at least 65%, at least 69%, at least 75%, or at least 90% sequence identity over the whole sequence length to ROCK1 protein of *Arabidopsis thaliana* with SEQ ID NO: 1. Preferably, the ROCK1 protein of *Arabidopsis thaliana* with SEQ ID NO. 1 and orthologous ROCK1 proteins thereof share the amino acid sequence motif GGIL-VGLVT (SEQ ID NO. 3).

Some specific examples of orthologous ROCK1 proteins of different species are given below:

Brassicaceae:
  ROCK1 protein of *Arabidopsis thaliana* with SEQ ID NO: 1 or 2;
  ROCK1 protein of *Brassica napus* with SEQ ID NO: 9, 10, 11 or 12;
  ROCK1 protein of *Brassica oleracea* with SEQ ID NO: 13 or 14;
  ROCK1 protein of *Brassica rapa* with SEQ ID NO: 15 or 16;
Rosaceae:
  ROCK1 protein of *Fragaria vesca* with SEQ ID NO: 17;
  ROCK1 protein of *Prunus persica* with SEQ ID NO: 18;
  ROCK1 protein of *Malus domestica* with SEQ ID NO: 19;
Poaceae:
  ROCK1 protein of *Sorghum bicolor* with SEQ ID NO: 21;
  ROCK1 protein of *Hordeum vulgare* with SEQ ID NO: 22;
  ROCK1 protein of *Oryza sativa* with SEQ ID NO: 27;
  ROCK1 protein of *Brachypodium distachyon* with SEQ ID NO: 20;
  ROCK1 protein of *Zea mays* with SEQ ID NO: 24 or 25;
  ROCK1 protein of *Setaria italic* with SEQ ID NO: 23;
  ROCK1 protein of *Triticum aestivum* with SEQ ID NO: 26;
Fabaceae:
  ROCK1 protein of *Glycine max* with SEQ ID NO: 28;
  ROCK1 protein of *Phaseolus vulgaris* with SEQ ID NO: 29;
  ROCK1 protein of *Cicer arietinum* with SEQ ID NO: 30;
Vitaceae:
  ROCK1 protein of *Vitis vinifera* with SEQ ID NO: 31;
Solanaceae:
  ROCK1 protein of *Solanum lycopersicum* with SEQ ID NO: 32;
Malvaceae:
  ROCK1 protein of *Theobroma cacao* with SEQ ID NO: 33;
Rutaceae:
  ROCK1 protein of *Citrus sinensis* with SEQ ID NO: 34;
  ROCK1 protein of *Citrus clementina* with SEQ ID NO: 35;
Pinaceae:
  ROCK1 protein of *Picea sitchensis* with SEQ ID NO: 36;
Rubiaceae:
  ROCK1 protein of *Coffea canephora* with SEQ ID NO: 37;
Musaceae:
  ROCK1 protein of *Musa acuminate* with SEQ ID NO: 38; and
Funariaceae:
  ROCK1 protein of *Physcomitrella patens* with SEQ ID NO: 39.

In Table 1 sequence homology for above mentioned orthologous ROCK1 proteins is given relative to ROCK1 of *Arabidopsis thaliana* with SEQ ID NO: 1.

TABLE 1

Comparison of the identity of the protein sequences of ROCK1 At5g65000.1 homologous proteins in different plant species.

| Protein origin and paralogue number | % identity with ROCK1 protein sequence |
|---|---|
| Arabidopsis_thaliana (SEQ ID NO: 1) | 100.00 |
| Physcomitrella_patens (SEQ ID NO: 39) | 58.02 |
| Picea_sitchensis (SEQ ID NO: 36) | 66.87 |
| Brachypodium_distachyon (SEQ ID NO: 20) | 70.50 |
| Hordeum_vulgare (SEQ ID NO: 22) | 69.25 |
| Triticum_aestivum (SEQ ID NO: 26) | 69.66 |
| Oryza_sativa (SEQ ID NO: 27) | 71.12 |
| Setaria_italica (SEQ ID NO: 23) | 71.34 |
| Zea_mays2 (SEQ ID NO: 25) | 69.66 |
| Sorghum_bicolor (SEQ ID NO: 21) | 70.28 |
| Zea_mays1 (SEQ ID NO: 24) | 70.59 |
| Musa_acuminata (SEQ ID NO: 38) | 76.16 |
| Cicer_arietinum (SEQ ID NO: 30) | 76.32 |
| Glycine_max (SEQ ID NO: 28) | 77.26 |
| Phaseolus_vulgaris (SEQ ID NO: 29) | 76.16 |
| Fragaria_vesca (SEQ ID NO: 17) | 77.09 |
| Prunus_persica (SEQ ID NO: 18) | 77.64 |
| Malus_domestica (SEQ ID NO: 19) | 77.09 |
| Brassica_napus3 (SEQ ID NO: 11) | 92.31 |
| Brassica_oleracea1 (SEQ ID NO: 13) | 92.92 |
| Brassica_napus4 (SEQ ID NO: 12) | 92.24 |
| Brassica_rapa2 (SEQ ID NO: 16) | 92.52 |
| Brassica_napus1 (SEQ ID NO: 9) | 92.62 |
| Brassica_oleracea2 (SEQ ID NO: 14) | 92.62 |
| Brassica_napus2 (SEQ ID NO: 10) | 92.31 |
| Brassica_rapa1 (SEQ ID NO: 15) | 91.98 |
| Coffea_canephora (SEQ ID NO: 37) | 75.23 |
| Solanum_lycopersicum (SEQ ID NO: 32) | 78.64 |
| Vitis_vinifera (SEQ ID NO: 31) | 75.54 |
| Theobroma_cacao (SEQ ID NO: 33) | 82.64 |
| Citrus_sinensis (SEQ ID NO: 34) | 75.23 |
| Citrus_clementina (SEQ ID NO: 35) | 75.23 |

Proteins were identified by BLASTP search and percent identity is derived from ClustalOmega alignment.

The orthologous ROCK1 protein exhibits essentially the same function as the ROCK1 protein of *Arabidopsis thaliana* comprising of the amino acid sequence with SEQ ID NO: 1.

An orthologue of ROCK1 protein exhibits preferably at least 50% of the activity of ROCK1 protein of *Arabidopsis thaliana* with SEQ ID NO: 1 when measured in above mentioned biochemical in vitro test of Gerardy-Schahn et al or Ashikov et al, more preferably at least 70%, even more preferred at least 90%.

For the purpose of the present invention, sequence "identity" is objectively determined by any of a number of methods. The skilled person is well aware of these methods and can choose a suitable method without undue burden. A variety of methods for determining relationships between two or more sequences (e.g. identity, similarity and/or homology) are available and well known in the art. The methods include manual alignment, computer assisted sequence alignment and combinations thereof, for example. A number of algorithms (which are generally computer implemented) for performing sequence alignment are widely available or can be produced by one of skill. The degree of identity of one amino acid sequence or nucleotide sequence to another can be determined by following the algorithm BLAST by Karlin and Altschul (Proc. Natl. Acad. Sci. USA 90: 5873-5877, 1993). Programs such as BLASTN and BLASTX developed based on this algorithm (Altschul et al. (1990) J. Mol. Biol. 215: 403-410) may be used. To analyze a nucleotide sequence according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art (see http://www.ncbi.nlm.nih.gov.).

The endogenous ROCK1 gene may comprise or consist of a nucleic acid hybridizing under stringent conditions to one of the nucleic acids defined supra under (a), (b), (c), and/or (d).

Stringent hybridization conditions of the present invention include conditions such as: 6 M urea, 0.4% SDS, and 0.5×SSC; and those which yield a similar stringency to the conditions. Nucleic acid sequences with higher homology are expected when hybridization is performed under conditions with higher stringency, for example, 6 M urea, 0.4% SDS, and 0.1×SSC. Those nucleic acid sequences isolated under such conditions are expected to encode a protein having a high amino acid level homology with ROCK1 protein with SEQ ID NO: 1 or 2. Herein, high homology means an identity of at least 50% or more, 70% or more, or 90% or more (e.g. 95% or more), through the entire amino acid sequence.

The term "disruption" or "disrupted" as used herein means that a gene can be structurally disrupted so as to comprise at least one mutation or structural alteration such that the disrupted gene is incapable of directing the efficient expression of a full-length and/or fully functional gene product. An endogenous gene usually is disrupted in the sense of the present invention when the endogenous gene comprises one or more mutations, such as:
(i) a "missense mutation", which is a change in the nucleic acid sequence that results in the substitution of an amino acid for another amino acid;
(ii) a "nonsense mutation" or "STOP codon mutation", which is a change in the nucleic acid sequence that results in the introduction of a premature STOP codon and, thus, the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
(iii) an "insertion mutation" of one or more amino acids, due to one or more codons having been added in the coding sequence of the nucleic acid;
(iv) a "deletion mutation" of one or more amino acids, due to one or more codons having been deleted in the coding sequence of the nucleic acid;
(v) a "frameshift mutation", resulting in the nucleic acid sequence being translated in a different frame downstream of the mutation. A frameshift mutation can have various causes, such as the insertion, deletion or duplication of one or more nucleotides.

As already mentioned, it is desired that the mutation(s) in the endogenous gene preferably result in a mutant protein comprising significantly reduced or no biological activity in vivo or in the production of no protein. Basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant ROCK1 protein, such as mutations leading to truncated proteins, whereby significant portions of the functional domains are lacking.

The term "disruption" or "disrupted" also encompasses that the disrupted gene or one of its products can be functionally inhibited or inactivated such that a gene is either not expressed or is incapable of efficiently expressing a full-length and/or fully functional gene product. Functional inhibition or inactivation can result from a structural disruption and/or interruption of expression at either level of transcription or translation. Functional inhibition or inactivation can also be achieved e.g. by methods such as antisense polynucleotide gene suppression, double stranded RNA induced gene silencing, ribozyme techniques, and the like as specified in detail further below. The inhibition of expression and/or activity can be the result of, e.g. antisense constructs, sense constructs, RNA silencing constructs, RNA interference, genomic disruptions (e.g. transposons, tilling, homologous recombination, etc.), transcriptional activator-like effectors and transcription activator-like effector nucleases, CRISPR/Cas, designer zinc finger nucleases (ZFNs), homing meganucleases and/or the like. The inhibition of expression and/or activity can be measured by determining the presence and/or amount of transcript (e.g. by Northern blotting or quantitative or semi-quantitative RT-PCR techniques) and/or by determining the presence and/or amount of full length or truncated polypeptide encoded by said gene (e.g. by ELISA or Western blotting) and/or by determining presence and/or amount of protein activity of the product of the disrupted gene.

The term "disruption" or "disrupted" as used herein is to be understood that a disruption also encompasses a disruption which is effective only in a part of a plant, in a particular cell type or tissue like e.g. the reproductive meristem or the shoot apex. A disruption may be achieved by interacting with or affecting within a coding region, within a non-coding region and/or within a regulatory region like e.g. a promoter region of a particular gene. A disruption in the sense of the present invention preferably results in complete or partial loss-of-function of the disrupted gene and/or its product.

At least one of the disruptions of the method of the invention can be produced by introducing at least one polynucleotide sequence comprising a nucleic acid sequence which has at least about 90%, at least about 95%, at least about 99%, about 99.5% or more sequence identity to one of SEQ ID NO: 4, 5, 6, 7 and/or 8 or a subsequence thereof, or a complement thereof, into the genome of a plant cell, such that the at least one polynucleotide sequence is linked to a promoter in a sense or antisense orientation. In another embodiment, the disruption is introduced into the genome of a plant cell by introducing at least one polynucleotide sequence configured for RNA silencing or interference.

One, more than one or all disruptions of at least one of the endogenous genes may comprise insertion of one or more transposons. A "transposable element" (TE) or "transposable genetic element" is a DNA sequence that can move from one location to another in a cell. Movement of a transposable element can occur from episome to episome, from episome to chromosome, from chromosome to chromosome, or from chromosome to episome. Transposable elements are characterized by the presence of inverted repeat sequences at their termini. Mobilization is mediated enzymatically by a "transposase". Structurally, a transposable element is categorized as a "transposon" (TN) or an "insertion sequence element" (IS element) based on the presence or absence, respectively, of genetic sequences in addition to those necessary for mobilization of the element. A mini-transposon or mini-IS element typically lacks sequences encoding a transposase.

A disruption in the sense of the present invention can comprise one or more point mutations in at least one of the endogenous genes.

One, more than one or all disruptions of the endogenous ROCK1 gene can be homozygous disruptions. Alternatively, one, more than one or all disruptions can be heterozygous disruptions. In certain embodiments, the disruptions of the endogenous ROCK1 gene can include homozygous disruptions, heterozygous disruptions or a combination of homozygous disruptions and heterozygous disruptions.

The disruption may be introduced by way of introduction of an expression cassette into the genome of the plant. An "expression cassette" is a nucleic acid construct, e.g. a vector, such as a plasmid, a viral vector, etc., capable of producing transcripts and, potentially, polypeptides encoded by a polynucleotide sequence. An expression vector is capable of producing transcripts in an exogenous cell, e.g. a bacterial cell, or a plant cell, in vivo or in vitro, e.g. a cultured plant protoplast. Expression of a product can be either constitutive or inducible depending, e.g. on the promoter selected. Antisense, sense or RNA interference or silencing configurations that are not or cannot be translated are expressly included by this definition. In the context of an expression vector, a promoter is said to be "operably linked" or "functionally linked" to a polynucleotide sequence if it is capable of regulating expression of the associated polynucleotide sequence. The term also applies to alternative exogenous gene constructs, such as expressed or integrated transgenes. Similarly, the term operably or functionally linked applies equally to alternative or additional transcriptional regulatory sequences such as enhancers, associated with a polynucleotide sequence.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

A polynucleotide sequence, nucleic acid sequence or gene is said to "encode" a sense or antisense RNA molecule, or RNA silencing or interference molecule or a polypeptide, if the polynucleotide sequence can be transcribed (in spliced or unspliced form) and/or translated into the RNA or polypeptide, or a subsequence thereof. The skilled person is well aware of the degeneracy of the genetic code, allowing for a number of different nucleic acid sequences encoding for the same amino acid sequence or polypeptide and has no difficulties in determining whether a given nucleic acid sequence encodes for a given amino acid sequence or polypeptide.

"Expression of a gene" or "expression of a nucleic acid" means transcription of DNA into RNA (optionally including modification of the RNA, e.g. splicing), translation of RNA into a polypeptide (possibly including subsequent modification of the polypeptide, e.g. posttranslational modification), or both transcription and translation, as indicated by the context.

The method of the invention can further comprise the steps of introducing into the plant genome or the genome of a plant cell a disruption of endogenous ROCK1 gene, and regenerating a plant having such an altered genome. Said disruption may be stably introduced into the genome of the plant or plant cell in order to generate a plant. A disruption is considered stably introduced into the genome of a plant or plant cell, if said disruption is copied and segregated during cell division and is passed on to the progeny of said plant or plant cell.

The method of the invention can be used to produce a plant with an increase in yield-related traits per plant and, thereby, an increase in yield in a plant and the progeny derived therefrom. Preferably, the method of the invention can be used to achieve an increase in number of siliques per plant and, thereby, an increase in seed yield in a plant and the progeny derived therefrom.

The present invention is also directed to a plant obtainable or obtained by the method of the invention or progeny thereof comprising a disruption of the endogenous ROCK1 gene. The endogenous ROCK1 gene may comprise or consist of:

(a) a nucleic acid encoding a ROCK1 protein comprising or consisting of the amino acid sequence of SEQ ID NO: 1 or 2 or an orthologue thereof;

(b) a nucleic acid encoding a ROCK1 protein comprising or consisting of an amino acid sequence with a sequence identity of at least 55%, preferably of at least 65%, more preferably of at least 69%, even more preferably of at least 75%, most preferably of at least 90% over the entire amino acid sequence with SEQ ID NO: 1 or 2;

(c) a nucleic acid comprising or consisting of one of the nucleic acid sequence with SEQ ID NO: 4, 5, 6, 7 and/or 8;

(d) a nucleic acid comprising or consisting of a nucleic acid with a sequence identity of at least 60%, preferably of at least 65%, more preferably of at least 69%, even more preferably of at least 75%, most preferably of at least 90% over the entire nucleic acid sequence with one of SEQ ID NO: 4, 5, 6, 7 and/or 8; or (e) a nucleic acid hybridizing under stringent conditions to one of the nucleic acid sequences defined under (a), (b), (c), and/or (d).

The plant of the invention can be produced by conventional means like e.g. transformation. The transformation of plant cells and protoplasts can be carried out in essentially any of the various ways known to those skilled in the art of plant molecular biology, including, but not limited to, the methods described herein. See, in general, Methods in Enzymology, Vol. 153 (Recombinant DNA Part D) Wu and Grossman (eds.) 1987, Academic Press. As used herein, the term "transformation" means alteration of the genotype of a host plant or plant cell by the introduction of a nucleic acid sequence, e.g. a "heterologous", "exogenous" or "foreign" nucleic acid sequence. The heterologous nucleic acid sequence need not necessarily originate from a different source but it will, at some point, have been external to the cell into which is introduced.

In the method of the invention and in the plant of the invention, the disruption of the endogenous gene can be facilitated by a number of different known techniques.

One, more than one or all of the disruptions of the endogenous ROCK1 gene can be facilitated by introducing into the genome and expressing in a plant cell or a plant a transgenic polynucleotide sequence, e.g. in antisense or sense configurations, or RNA silencing or interference configurations, etc., wherein the transgenic polynucleotide sequence comprises a nucleic acid sequence being or being complementary to one of the endogenous genes to be disrupted. In addition, said polynucleotide sequence may comprise a promoter, thereby inhibiting expression and/or activity of at least the disrupted endogenous gene compared to a corresponding control plant cell or plant lacking such disruptions (e.g. its non-transgenic parent or a non-transgenic plant of the same species). The transgenic polynucleotide sequence can be introduced by techniques including, but not limited to, e.g. electroporation, micro-projectile bombardment, *Agrobacterium*-mediated transfer, or other available methods. In certain aspects of the invention, the polynucleotide is linked to the promoter in a sense orientation or in an antisense orientation or is configured for RNA silencing or interference.

The disruption of one or more of the endogenous genes can be facilitated by the application of homology-dependent gene silencing, a technique already well described in the literature.

Alternatively, another approach to gene silencing can be with the use of antisense technology. Use of antisense nucleic acids is well known in the art. An antisense nucleic acid has a region of complementarity to a target nucleic acid, e.g. a particular genomic gene sequence, an mRNA, or cDNA. The antisense nucleic acid can be RNA, DNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced and tested by a number of well-established techniques.

Catalytic RNA molecules or ribozymes can also be used to inhibit expression of particular selected genes. It is possible to design ribozymes that specifically pair with virtually any desired target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs. A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes has been described. See, e. g., Haseloff et al. (1988) Nature, 334: 585-591.

Another method to inactivate a particular selected gene by inhibiting expression is by sense suppression. Introduction of expression cassettes in which a nucleic acid is configured in the sense orientation with respect to the promoter has been shown to be an effective means by which to block the transcription of a desired target gene. See, e. g., U.S. Pat. Nos. 5,034,323, 5,231,020 and 5,283,184.

A disruption of an endogenous ROCK1 gene can also be produced by using RNA silencing or interference (RNAi), which can also be termed post-transcriptional gene silencing (PTGS) or co-suppression. In the context of this invention, "RNA silencing" (also called RNAi or RNA-mediated interference) refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g. histone acetylation and heterochromatin formation leading to inhibition of transcription of the target mRNA). In "RNA interference" the presence of the single-stranded or double-stranded RNA in the cell leads to endonucleolytic cleavage and then degradation of the target mRNA.

A transgene (e.g. a sequence and/or subsequence of a gene or coding sequence of interest) can be introduced into a plant cell to disrupt one or more genes by RNA silencing or interference (RNAi). For example, a sequence or subsequence (the transgene) includes a small subsequence, e.g. about 21-25 bases in length, a larger subsequence, e.g. about 25-100 or about 100-2000 (or about 200-1500, about 250-1000, etc.) bases in length, and/or the entire coding sequence or gene selected from or being complementary to the endogenous gene to be disrupted. Such a transgene can include a region in the sequence or subsequence that is about 21-25 bases in length with at least 80%, at least 90%, or at least 99% identity to a subsequence of one of the nucleic acid sequences with the SEQ ID NO: 4, 5, 6, 7 and/or 8.

Use of RNAi for inhibiting gene expression in a number of cell types (including, e.g. plant cells) and organisms, e.g. by expression of a hairpin (stem-loop) RNA or of the two strands of an interfering RNA, for example, is well described in the literature, as are methods for determining appropriate interfering RNA (s) to target a desired gene, and for generating such interfering RNAs. For example, RNA interference is described e.g. in US patent application publications 2002/0173478, 2002/0162126, and 2002/0182223.

The polynucleotide sequence(s) or subsequence(s) to be expressed to induce RNAi can be expressed, e. g., under control of a constitutive promoter, an inducible promoter, or a tissue specific promoter. Expression from a tissue-specific promoter can be advantageous in certain embodiments. A "promoter", as used herein, includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds or spatially in regions such as endosperm, embryo, or meristematic regions. Such promoters are referred to as "tissue-preferred" or "tissue-specific". A temporally regulated promoter drives expression at particular times, such as between 0-25 days after pollination. A "cell-type-preferred" promoter primarily drives expression in certain cell types in one or more organs, for example, vascular cells in roots or leaves. An "inducible" promoter is a promoter that is under environmental control and may be inducible or de-repressible. Examples of environmental conditions that may effect transcription by inducible promoters include anaerobic conditions or the presence of light. Tissue-specific, cell-type-specific, and inducible promoters constitute the class of "non-constitutive" promoters. A "constitutive" promoter is a promoter that is active under most environmental conditions and in all or nearly all tissues, at all or nearly all stages of development.

One, more than one or all disruptions of the endogenous ROCK1 gene can be introduced by transposon-based gene inactivation like e.g. T-DNA insertion. The one or more mutations in the gene sequence can comprise one or more transposon insertions and the disruptions inhibit expression and/or activity of at least the disrupted endogenous gene compared to a corresponding control plant cell or plant lacking such disruptions. For example, the one or more mutations comprise a homozygous disruption of one or more genes mentioned above or the one or more mutations comprise a heterozygous disruption of one or more genes mentioned above or a combination of both homozygous disruptions and heterozygous disruptions.

Transposons were first identified in maize by Barbara McClintock in the late 1940s. The Mutator family of transposable elements, e.g. Robertson's Mutator (Mu) transposable elements, are typically used in plant gene mutagenesis, because they are present in high copy number (10-100) and insert preferentially within and around genes.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e. they are retroelements. There are at least three types of Class I transposable elements, e.g. retrotransposons, retroposons, SINE-like elements. Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalysed by reverse transcriptase and RNase H encoded by the transposon. Examples fall into the Ty1-copia and Ty3-gypsy groups as well as into the SINE-like and LINE-like classifications. A more detailed discussion can be found in Kumar and Bennetzen (1999) Plant Retrotransposons in Annual Review of Genetics 33: 479.

In addition, DNA transposable elements such as Ac, TamI and En/Spm are also found in a wide variety of plant species, and can be utilized in the invention.

Transposons (and IS elements) are common tools for introducing mutations in plant cells. These mobile genetic elements are delivered to cells, e.g. through a sexual cross, transposition is selected for and the resulting insertion mutants are screened, e.g. for a phenotype of interest. The disrupted genes can then be introduced into other plants by crossing the disrupted plants with a non-disrupted plant, e.g. by a sexual cross. Any of a number of standard breeding techniques can be used, depending upon the species to be crossed. The location of a TN within a genome of a plant can be easily determined by known methods, e.g. sequencing of flanking regions. For example, a PCR reaction from the plant can be used to amplify the sequence, which can then be diagnostically sequenced to confirm its origin. Optionally, the insertion mutants are screened for a desired phenotype, such as the inhibition of expression or activity of a gene of interest compared to a control plant.

TILLING can also be used to introduce and identify a disruption of an endogenous ROCK1 gene. TILLING is Targeting Induced Local Lesions In Genomes. See, e. g., McCallum et al., (2000), "Targeting Induced Local Lesions In Genomes (TILLING) for Plant Functional Genomics" Plant Physiology 123: 439-442; McCallum et al., (2000), "Targeted screening for induced mutations" Nature Biotechnology 18: 455-457; and, Colbert et al., (2001), "High-Throughput Screening for Induced Point Mutations" Plant Physiology 126: 480-484.

TILLING combines high density point mutations with rapid sensitive detection of the mutations. Typically, ethyl methanesulfonate (EMS) is used to mutagenize plant seed. EMS alkylates guanine, which typically leads to mis-pairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes. For example, DNA from M2 plants is pooled and mutations in a gene of interest are detected by detection of heteroduplex formation. Typically, DNA is prepared from each M2 plant and pooled. The desired gene is amplified by PCR. The pooled sample is then denatured and annealed to allow formation of heteroduplexes. If a mutation is present in one of the plants; the PCR products will be of two types: wild-type and mutant. Pools that include the heteroduplexes are identified by separating the PCR reaction, e.g. by Denaturing High Performance Liquid Chromatography (DPHPLC). DPHPLC detects mismatches in heteroduplexes created by melting and annealing of heteroallelic DNA. Chromatography is performed while heating the DNA. Heteroduplexes have lower thermal stability and form melting bubbles resulting in faster movement in the chromatography column. When heteroduplexes are present in addition to the expected homoduplexes, a double peak is seen. As a result, the pools that carry the mutation in a gene of interest are identified. Individual DNA from plants that make up the selected pooled population can then be identified and sequenced. Optionally, the plant possessing a desired mutation in a gene of interest can be crossed with other plants to remove background mutations.

Other mutagenic methods can also be employed to introduce a disruption of an endogenous ROCK1 gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

The plant containing the desired disruption(s) can be crossed with other plants to introduce the disruptions into another plant. This can be done using standard breeding techniques.

Homologous recombination can also be used to introduce a disruption of an endogenous ROCK1 gene. Homologous recombination has been demonstrated in plants. Homologous recombination can be used to induce targeted gene modifications by specifically targeting a gene of interest in vivo. Mutations in selected portions of a selected gene sequence (including 5' upstream, 3' downstream, and intragenic regions) are made in vitro and introduced into the desired plant using standard techniques. The mutated gene will interact with the target wild-type gene in such a way that homologous recombination and targeted replacement of the wild-type gene will occur in transgenic plants.

Furthermore, the endogeneous ROCK1 gene might be disrupted using different technologies based to the site-specific introduction of DNA double-strand breakages that might be followed by imperfect repair by non-homologous end-joining or homology-directed repair mechanisms that might lead to the disruption of the respective target gene.

Among them is the CRISPR/Cas technology. This is based on a Cas DNA nuclease that is guided to the DNA target sequence by a combination of two or one sequence-specific RNAs, which can be adapted to fit for the specific target sequence.

Another technology is based on designer zinc finger nucleases (ZFNs), which consist of a zink finger DNA binding domain and a DNA cleavage domain. The DNA binding domain can be modified to recognize the respective target DNA sequence within a given gene.

A third technology is based on transcription activator-like effector nucleases (TALENs). TALEN are consisting of DNA binding domain fused to a DNA cleavage domain. The DNA binding domain can be modified to recognize the respective target DNA sequence within a given gene.

A further technology is based on naturally occurring endonucleases having a large recognition site. The sequence specificity of the naturally occurring meganucleases might be adapted to the specific target gene by genetic engineering.

The plants of the invention, which can be consumed by humans and animals, may also be used, for example directly or after preparation known per se, as foodstuffs or feedstuffs. The invention further relates to the use of the above-described plants of the invention and of the cells, cell cultures, parts, such as, for example, roots, leaves, and propagation material such as seeds, tubers, beets/swollen tap roots or fruits derived therefrom for the production of food- or feedstuffs, pharmaceuticals or fine chemicals.

In the following the present invention is further described by way of examples.

FIGURES

FIG. 1. rock1 suppresses the cytokinin deficiency phenotype by repressing CKX activity. (A) Suppression of the 35S:CKX1 shoot phenotype by rock1-1 mutation in 4-week-old plants. (B) Relative transcript abundance of A-type ARR genes in shoots of soil-grown seedlings 10 days after germination (dag) measured by quantitative real-time PCR. Data are means±SD (n=4; *, P<0.05, t test). (C) Effect of rock1-1 on shoot development in plants expressing 35S:CKX2 or 35S:CKX3. The shoot fresh weight of soil-grown plants was determined 17 dag (means±SD, n 15). Significant differences to wild type were determined by t test (*, P<0.05). (D) CKX activity measured in total protein extracts. Activity is expressed relative to wild type. Values are means±SD (n≥3). Significant differences to the respective CKX overexpression line were determined by t test (*, P<0.05).

Figure 2:
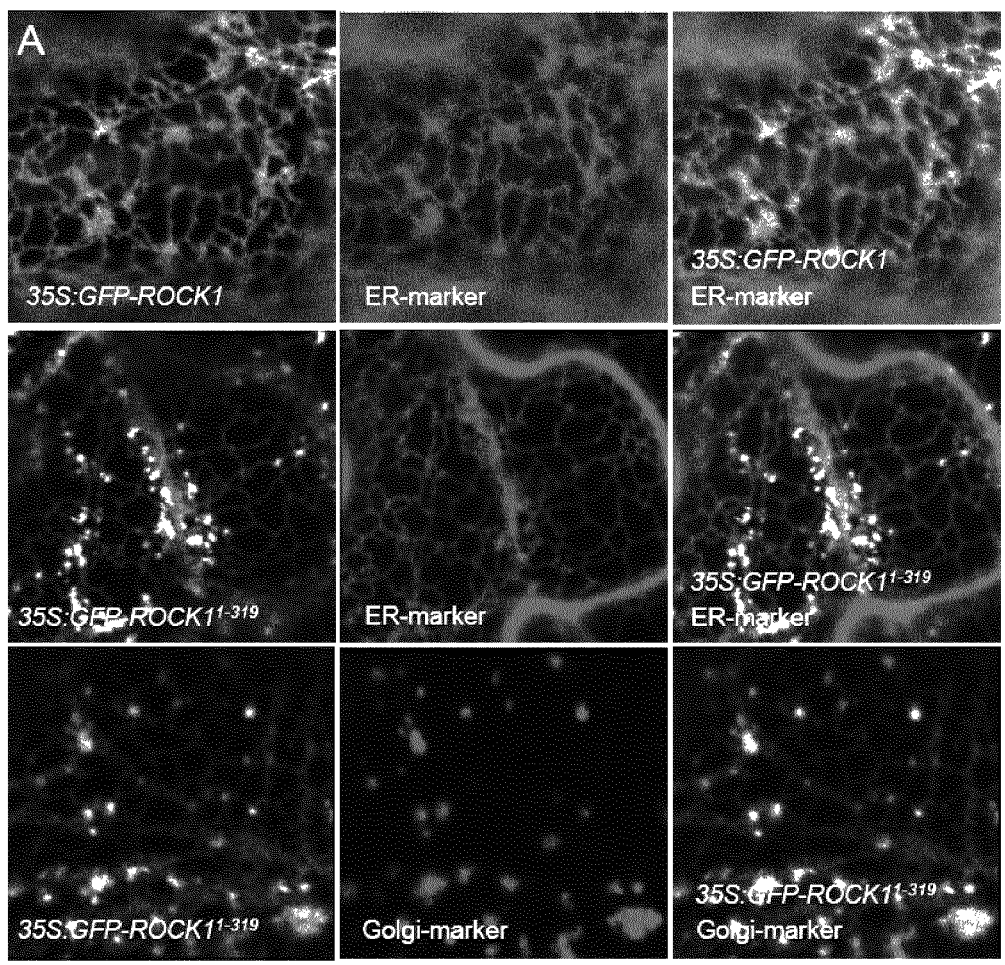
Figure 2:
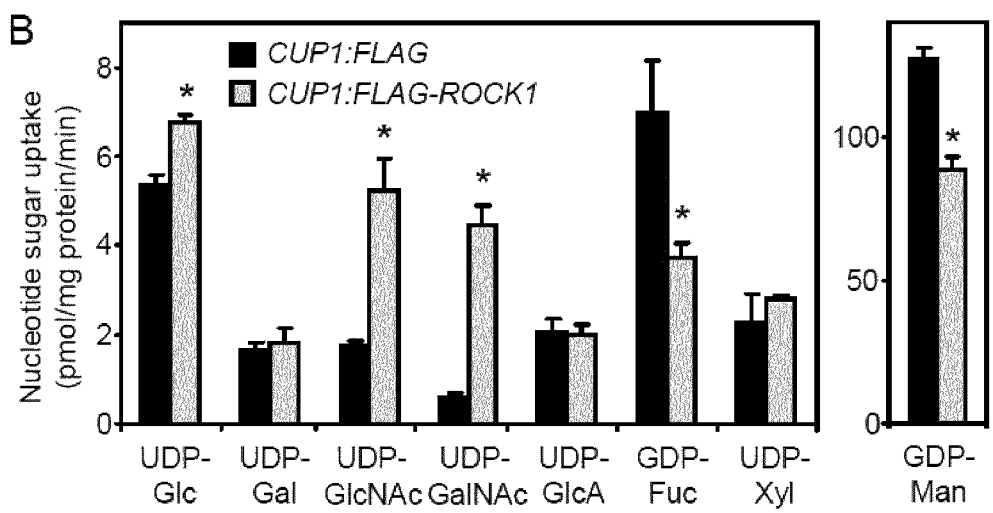

FIG. 2. ROCK1 encodes an ER-localised nucleotide sugar transporter. (A) Subcellular localization of ROCK1. 35S:GFP-ROCK1 (upper) and 35S:GFP-ROCK1$^{1-319}$ lacking the putative di-lysine signal (middle and lower row) were transiently expressed in N. benthamiana leaves and colocalization with marker proteins for ER and Golgi (red) analyzed. (B) Measurement of ROCK1-mediated uptake of radiolabeled nucleotide sugars into yeast microsomes expressing FLAG-ROCK1 or empty vector. Means±SEM (n=3; *, P<0.05, t test). UDP, uridine diphosphate; GDP, guanosine diphosphate; Glc, glucose; Gal, galactose; GlcNAc, N-acetylglucosamine; GalNAc, N-acetylgalactosamine; GlcA, glucuronic acid; Fuc, fucose; Xyl, xylose; Man, mannose.

Figure 3:
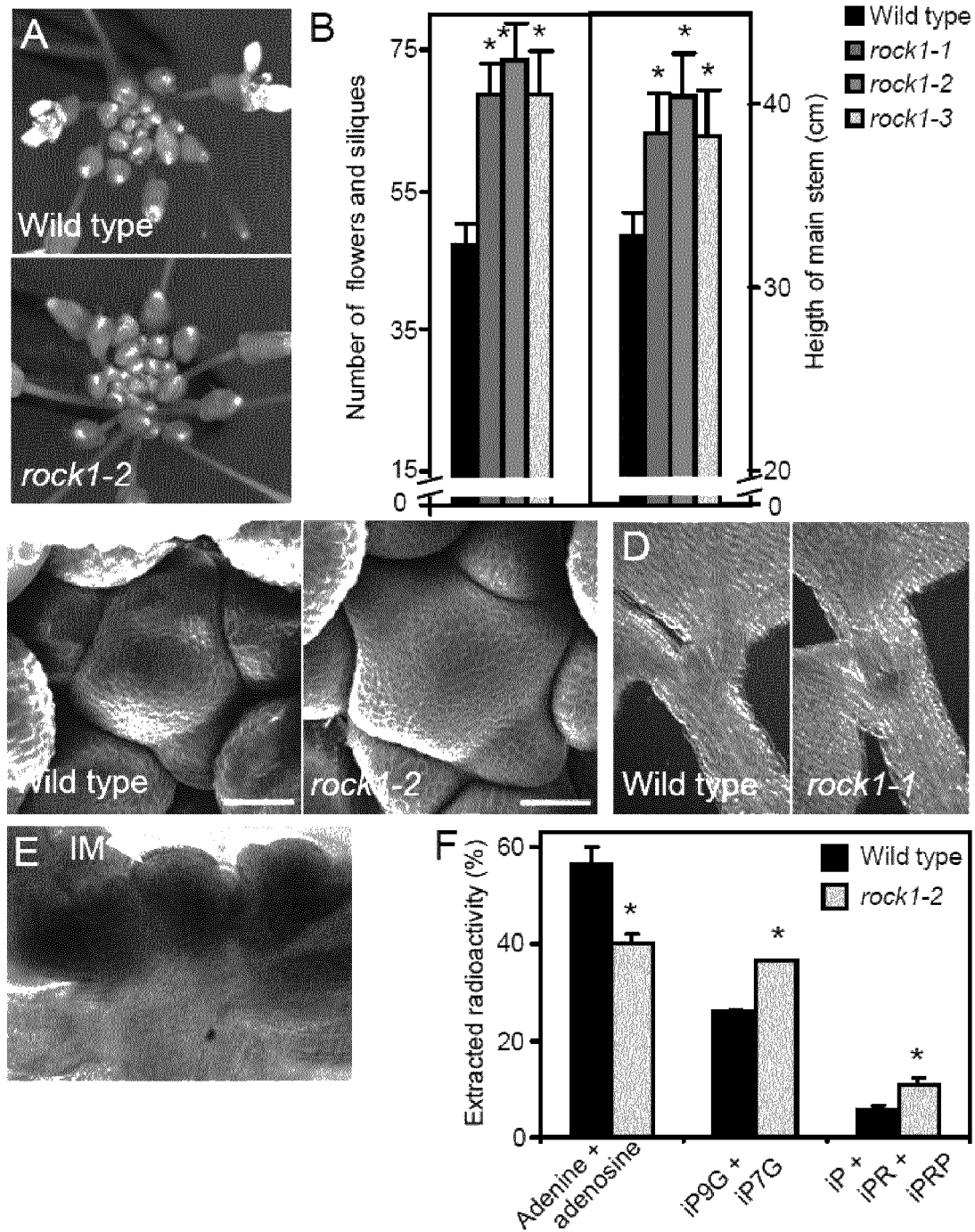

FIG. 3. ROCK1 regulates the activity of the shoot apical meristem. (A) The main inflorescence of the wild-type and rock1-2 plants 5 weeks after germination. (B) Number of flowers and siliques (stage 13-18) and height of the main stem of 7-week-old rock1 mutants and wild type. Values are means±SD (n≥20; *, P<0.05, t test). (C) Scanning electron micrographs of inflorescence meristems (IM) of 4-week-old wild-type and rock1-2 plants. Scale bar=30 μm. (D) Activity of the cytokinin reporter construct ARR5:GUS in the shoot meristems of Arabidopsis seedlings 2 dag. Staining performed for 1 h. (E) Histochemical detection of ROCK1: ROCK1-GUS activity in the IM and young flowers. (F) Analysis of cytokinin metabolic profiles in wild-type and rock1 seedlings after feeding with $^3$H[iP] for 2 h. Values are means±SD (n=3; *, P<0.05, t test). iP9G/iP7G, iP-N9/7-glucoside; iPR, iP riboside; iPRP, iPR 5'-phosphate.

Figure 4:
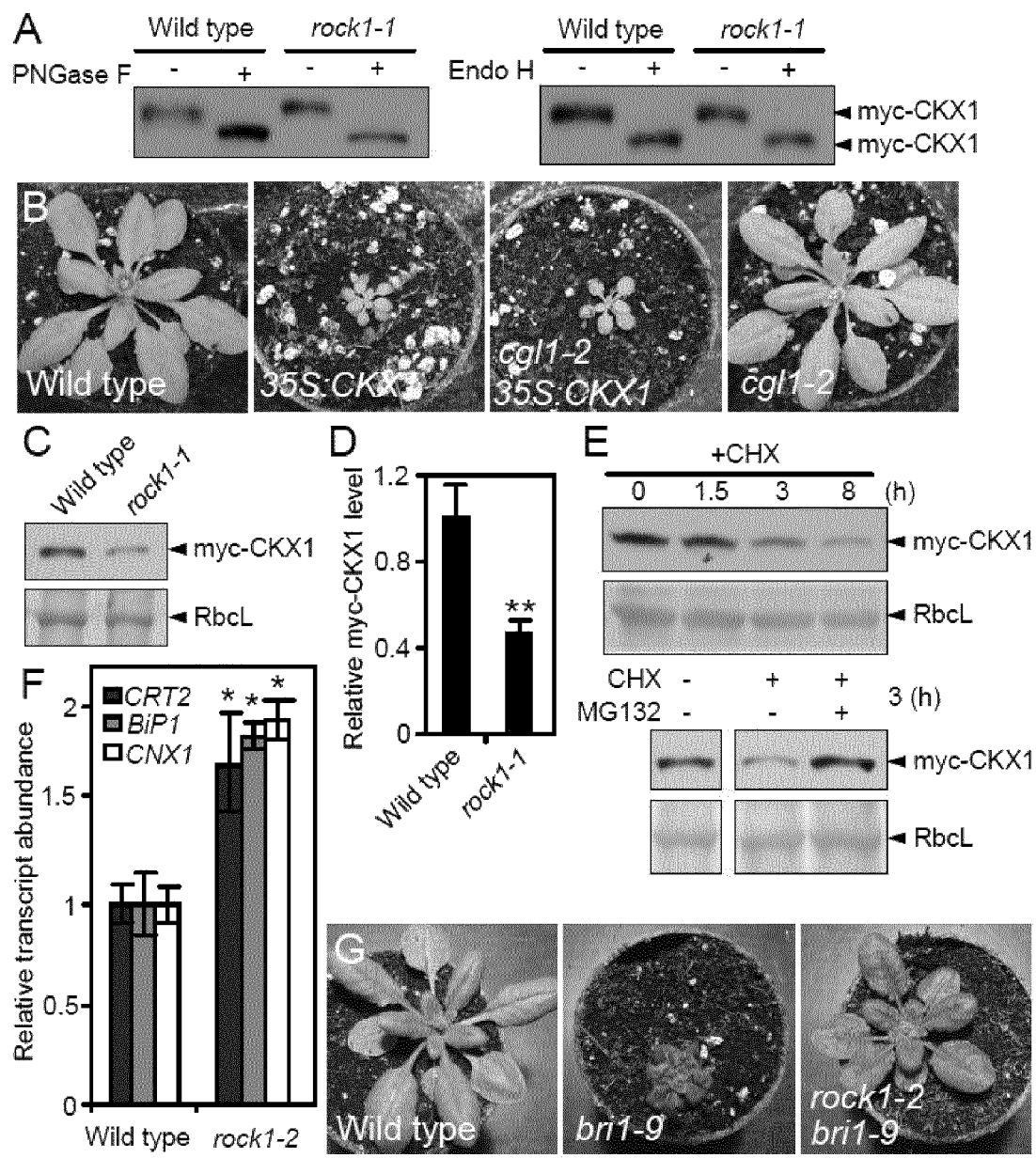

FIG. 4. ROCK1 regulates ERQC and CKX protein stability. (A) N-glycosylation status of myc-CKX1 protein in wild-type and rock1 seedlings. Protein extracts were treated with PNGase F or EndoH and the size of myc-CKX1 was compared to mock-treated control by SDS-PAGE and immunoblot with anti-myc antibody. (B) The loss of GnT-I activity in cgl1 mutants has no influence on the shoot phenotype of 35S:CKX1 plants (21 dag). (C) The level of myc-CKX1 is decreased in rock1 compared to wild type. Total protein extracts were analyzed by immunoblot with anti-myc antibody. Coomassie blue staining of Rubisco large subunit (RbcL) was used as loading control. Relative densitometric analysis of the myc-CKX1 signal is shown. Values are means±SEM (n=10; , P<0.01, t test). (D) Analysis of myc-CKX1 stability. Protein extracts were prepared from 7-d-old seedlings treated with mock or 100 μM CHX for indicated times and analyzed by immunoblotting. (E) myc-CKX1 is degraded in proteasome-dependent manner. Seedlings were treated with 100 μM MG132 and myc-CKX1 analyzed by immunoblotting and densitometry. Means±SEM (n=4; , P<0.01, t test). (F) Quantitative real-time PCR analysis of UPR genes in shoots of soil-grown seedlings 9 dag measured by. Means±SD are shown (n=4; *, P<0.05, t test). (G) The rock1 mutation suppresses the brassinosteroid deficiency shoot phenotype of bri1-9 mutant plants (26 dag).

EXAMPLES

Materials and Methods
Plant Material, Growth Conditions, Genotyping and Plant Transformation If not otherwise denoted, Arabidopsis thaliana Columbia-0 was used as the wild type. The T-DNA insertion lines rock1-2 (SALK_001259) and rock1-3 (901C01) were used. The following lines were described previously: 35S:CKX1-11, 35S:CKX2-9, 35S:CKX3-9, 35S:CKX7-GFP-26, ahk2-5, ahk3-7, cre1-2, atipt1, atipt3-2, atipt5-2, atipt7-1, cgl1 C6 (cgl1-2) and ARR5:GUS. Mutant lines were genotyped by PCR and dCAPS analysis using primers listed in Table S6 and S7, respectively. Plants were grown in vitro on half-strength Murashige and Skoog (MS) medium containing 10 g/L sucrose, 0.5 g/L MES and 8 g/L phytagel. For analysis of root growth, 12 g/L phytagel and cytokinin or DMSO as solvent control were added to the medium. Plants were grown under long day conditions (16 h light/8 h dark; 21/18° C.) in vitro or in the green house. Shoots of soil grown plants were sprayed with 10 μM INCYDE and 0.01% Silwet L-77 every 3 days starting 3 days after germination. The binary vector constructs were transformed into Arabidopsis plants by Agrobacterium tumefaciens (strain GV3101:pMP90) mediated floral dip method.

EMS Mutagenesis and Mapping

35S:CKX1 seeds were incubated with 0.2% ethyl methanesulfonate for 16 h and progeny of 1,100 M1 individuals were analyzed. By analyzing 1164 F2 recombinants from the cross between rock1-1 35S:CKX1 and Arabidopsis Landsberg erecta, rock1-1 was mapped to a 49-kb region (~0.13 cM) on the BAC clone MXK3. rock1-1 mutation was identified by sequencing candidate genes.

DNA Cloning

All primers used are listed in table S9. The ROCK1:ROCK1 construct used for complementation was prepared by amplifying a 4.3 kb large genomic fragment using primer 1 and 2. The fragment was cloned into the SacI site of pCB302. ROCK1:ROCK1-GUS was cloned by amplifying a genomic fragment including a 1.8 kb promoter region of ROCK1 and the whole coding region without the stop codon using primer 3 and 4. The amplicon was digested with NdeI and ligated into the XbaI site of the vector pCB308. For obtaining the construct CUP1:FLAG-ROCK1, the ROCK1 cDNA was amplified with the primer 5 and 6 using the SALK clone U87105 as template and cloned into the KpnI and EcoRI sites of pYEScupFLAGK. To generate the construct 35S:myc-CKX1, the CKX1 cDNA was PCR-amplified in two steps by using primer pairs 7/8 and 9/10. The final amplicon was cloned into the vector pDONR221 (Invitrogen) and subsequently pGWB18. To create 35S:GFP-ROCK1, the ROCK1 genomic coding sequence was PCR-amplified in two steps by using primer pairs 11/12 and 9/10 and cloned into pDONR222 (Invitrogen) and subsequently into pK7WGF2. The primer pair 11/13 was used for cloning the truncated ROCK1 version in the 35S:GFP-ROCK1 1-319 construct. To create 35S:ROCK1-GFP, the ROCK1 genomic coding sequence was PCR-amplified by using primer pairs 11/14 and 9/10 and cloned into pDONR222 and subsequently into pB7FWG2. To create ROCK1:ROCK1-GFPin, the sequence encoding eGFP was amplified with primer 15 and 16 using the vector pB7FWG2 as template and cloned into the VspI site of the vector pCB302-ROCK1:ROCK1 described above. To create ROCK1:ROCK1 1-319-GFPin, the GFP and the 0.4 kb EcoRI fragment were deleted from the vector pCB302-ROCK1:ROCK1-GFPin by partial digestion with VspI and EcoRI creating part 1. A fusion construct consisting of GFP and the ROCK1 3' part was PCR-amplified using the primer 15 and 17 and pCB302-ROCK1:ROCK1-GFPin as template, further digested by VspI and partially disgested by EcoRI. The resulting 0.7 kb fragment was ligated with part 1 and GFP inserted into the VspI site. All cloned sequences were verified by sequencing.

RNA Extraction, cDNA Synthesis and qPCR

Whole RNA was extracted from tissues by TRIzol method. Samples were treated with DNase I (Thermo Scientific) and 2 µg RNA were transcribed into cDNA by Superscript III reverse transcriptase (Invitrogen) using a 25-mer oligo-dT primer at 2.5 µM and a 9-mer random primer at 4.5 µM. 50 ng cDNA were used as template in a qPCR reaction consisting of 0.01 U/µL Immolase DNA-Polymerase (BioLine), the corresponding 1× buffer, 2 mM MgCl2, 100 µM each dNTP, 0.1×SYBR Green I (Fluka), 50 nM ROX (Sigma) and 300 nM each primer (Table S8) in a final volume of 20 µL. qPCR analysis was done using a 7500 Fast Real-Time PCR system (Applied Biosystems). The qPCR temperature program consisted of the following steps: 95° C. for 15 min; 40 cycles of 95° C. 15 s, 55° C. 15 s, 72° C. 15 s; followed by melting curve analysis. Relative transcript abundance of each gene was calculated based on the $\Delta\Delta Ct$ method. β-Tubulin or UBC10 were used for normalization.

CKX Activity Assay

CKX activity in seedling extracts was determined by a modified end-point method. Seedlings were frozen in liquid nitrogen and grinded in a tissue-mill (Retsch) to a fine powder. 1.5 to 2 mL extraction buffer (0.2 M Tris-HCl pH 7.5, 0.3% Triton X-100, complete protease inhibitor cocktail without EDTA (Roche)) was added per 1 g of plant material and incubated for 20 min on ice followed by centrifugation at 2,000 g for 5 min. The protein concentrations in the supernatants were measured using a bicinchoninic acid protein assay kit (Pierce). 200 µL (35S:CKX1 and 35S:CKX3 plants) or 50 µL (35S:CKX2 plants) of the extract were incubated with 500 µL ferricyanide (CKX1 and CKX3) or 2,6-dichlorophenol indophenol (CKX2), 100 mM McIlvaine buffer (CKX1 and CKX3 pH 5, CKX2 pH 6.5) and 250 µM iP9G (CKX1) or iP (CKX2 and CKX3) in a final volume of 600 µL. The reaction was incubated for 1-2 h at 37° C., stopped by 0.3 mL 40% trichloroacetic acid (TCA) and centrifuged at 16,000 g for 5 min. 850 µL of the supernatant were mixed with 200 µL 2% 4-aminophenol (dissolved in 6% TCA), incubated for 1 min and the concentration of the formed Schiff base determined by measuring the absorption at 352 nm.

Transient Expression in N. benthamiana and Confocal Laser Scanning Microscopy

Infiltration was performed as described previously using A. tumefaciens strain GV3101:pMP90 and 6-weeks-old N. benthamiana plants. For co-expression, the Agrobacterium cultures harbouring different expression constructs were mixed in infiltration medium to a final OD600 of 0.05 for each. 35S:p19 was included in all infiltrations. GFP-fusion proteins and mCherry-marker proteins were analyzed by confocal laser scanning microscope (TCS SPS, Leica) 3-5 days after infiltration. GFP and mCherry were excited at 488 nm and 561 nm and the fluorescence detected at 498-538 nm and 600-630 nm, respectively.

Deglycosylation Assays and Immunoblot Analysis

Proteins were extracted and the concentration determined as described for the CKX activity assay. Proteins were separated by 10% SDS-PAGE and blotted on PVDF membrane (Millipore). Membranes were blocked with 5% skim milk in PBS containing 0.1% Tween-20. A mouse monoclonal anti-myc antibody (clone 4A6, Millipore, dilution 1:2500) followed by a goat anti-mouse antibody coupled to horse radish peroxidase (sc-2005, Santa-Cruz, dilution 1:5000) was used to detect myc-CKX1. Bound antibodies were visualized with SuperSignal West Pico chemiluminescent substrate (Thermo Scientific). Densitometric analysis was performed using the ImageJ software v.1.47 (http://imagej.nih.gov/ij/). Intensities were normalized to the loading control and calculated relative to wild type samples. For analysis of the N-glycosylation total proteins were treated by Endoglycosidase Hf and PNGase F (New England Biolabs) according to the manufacturer prior to SDS-PAGE.

GUS Staining, Microscopy and Scanning Electron Microscopy

GUS staining was performed as described before. For microscopic analysis, tissues were cleared. The inflorescence meristem of the main stem from 4 weeks old soil grown plants was dissected and analyzed by scanning electron microscopy as described before.

Quantification of Endogeneous Cytokinins

Extraction, purification and quantification by ultraperformance liquid chromatography-electrospray tandem mass spectrometry was performed as described previously. At least three independent biological replicates were analyzed for each genotype and tissue.

Cytokinin-Feeding Experiments

Wild-type and rock1 seedlings were grown for 8 days in ½ MS liquid medium with 0.1% sucrose. 200 mg seedlings were transferred into medium containing 39 nM 3H[iP] (32

Ci/mmol, obtained from the Isotope Laboratory of the Institute of Experimental Botany AS CR, Prague, Czech Republic) and incubated for 2 h. Seedlings were washed twice in water and snap-frozen. Cytokinins were extracted and purified, vacuum evaporated at 40° C. and resolved in 500 µL 10% methanol. After dephosphorylation, HPLC analyses was performed on an Alliance 2690 Separations Module (Waters, Milford, Mass., USA) linked to PDA 996 (Waters, Milford, Mass., USA). Samples were separated on a Symmetry C18 column (150×2.1 mm, 5 µm, Waters, Milford, Mass., USA) at 30° C. The mobile phase consisted of the following sequence of linear gradients and isocratic flows of solvent A (water) and solvent B (methanol with 5 mM HCOOH) at a flow rate of 0.25 mL/min-1: 3-60% B over 3 min, 60% B for 5 min, 60-100% B over 2 min, and 100-3% B over 2 min and equilibrated to initial conditions for 4 min. The absorbance was monitored at 268 nm and effluent was collected at 30 sec intervals. The radioactivity was measured with a scintillation counter (Beckman, Ramsey, Minn., USA) and assigned to iP metabolites and degradation products by comparison to the retention time of unlabeled standards (adenosine, adenine, iP7G, iP9G, iP, iPR).

Nucleotide-Sugar Transport Assay

Nucleotide-sugar transport into *Saccharomyces cerevisiae* (BY4741) transformed with the construct pYEScup-FLAGK-ROCK1 or the empty vector control was measured as described by Ashikov et al. (2005): "cultured cells were harvested by centrifugation (5 min at 1,500×g) and washed twice with ice-cold 10 mm NaN$_3$. The weight of wet cells was measured, and cells were resuspended in zymolyase buffer (3 ml/g of cells; 50 mm potassium phosphate, pH 7.5; 1.4 m sorbitol; 10 mm NaN$_3$ and 0.3% β-mercaptoethanol) containing 0.6 mg/ml of zymolyase-100T. The suspension was incubated for 20 min at 30° C. Spheroplasts were collected by centrifugation (5 min at 1,000×g) and resuspended in lysis buffer (4 ml/g of cells; 10 mm Hepes-Tris, pH 7.4; 0.8 m sorbitol; 1 mm EDTA) containing complete EDTA-free protease inhibitor mixture (Roche Applied Science). After homogenization with 10 strokes in a Dounce homogenizer, the lysate was centrifuged (5 min, 1,500×g) to remove unlysed cells and debris. Endoplasmic reticulum- and Golgi-rich fractions were then obtained by centrifugation at 10,000×g for 10 min (endoplasmic reticulum) and 100,000×g for 1 h (Golgi). The 100,000×g pellet was carefully resuspended in lysis buffer (0.8 ml/g of cells), and aliquots of 100 µl were snap-frozen and kept at −80° C. Protein concentrations were determined using the BCA™ kit (Pierce). For transport assay reactions, equal volumes (50 µl of each) of 2 mm radioactive nucleotide sugar (2,000-4,000 dpm/pmol) in assay buffer (10 mm Tris-HCl, pH 7.0; 0.8 m sorbitol; 2 mm MgCl$_2$) and vesicle preparation (equivalent to 75-100 µg of protein) were incubated for 30 s at 30° C. Reactions were stopped by dilution with 1 ml of assay buffer containing 1 µm respective cold nucleotide sugar. The separation of vesicles and nucleotide sugars was achieved by filtration trough nitrocellulose filter (MF™ membrane filters Millipore, Bedford, Mass.). Filters were washed three times with 2 ml of ice-cold assay buffer containing the corresponding cold nucleotide sugar at a concentration of 1 µm, and radioactivity associated with the vesicular fraction was measured by liquid scintillation in a LS 5000CE counter (Beckman Coulter). Golgi vesicles from yeast cells transformed with an empty vector were used to measure endogenous transport."

Results

Repressor of Cytokinin Deficiency1 Decreases the CKX Activity

To identify new molecular components required for the proper activity of the CK system, we carried out a genetic screen for suppressor alleles of the CK deficiency syndrome displayed by 35S:CKX1 plants. The isolated mutant line repressor of cytokinin deficiency1 (rock1) was characterized by restored rosette size, leaf and flower number, flowering time and, to lesser extent, root growth (FIG. 1A). Genetic analysis showed that rock1-1 is a recessive second-site allele (Table S1) not affecting 35S:CKX1 transgene expression.

To understand whether rock1 directly influenced the CK status, the transcript levels of primary CK response genes, A-type *Arabidopsis* response regulators (ARRs), were analyzed in the suppressor line. The mRNA levels of all analyzed ARR genes were restored almost to those found in wild type (FIG. 1B). Next, we analyzed the impact of rock1 mutation on the endogenous CK content. Because rock1-1 had stronger effects on shoot than on root development, we determined the CK content specifically in seedling shoots and inflorescences of the suppressor line. CK levels in the rock1-1 suppressor line were five- and two-fold increased in comparison to shoots and inflorescences of the parental 35S:CKX1 line, respectively (Table S2 and S3), however, the restoration of the CK content was not complete.

To gain information about the specificity of rock1 in suppressing CKX overexpression phenotypes, rock1-1 was introgressed into 35S:CKX2, 35S:CKX3 and 35S:CKX7 plants. Whereas rock1-1 fully suppressed phenotypes caused by overexpression of CKX2 and CKX3 proteins localizing to the secretory pathway (FIG. 10), it had no effect on the phenotypes caused by the overexpression of the cytosolic CKX7 isoform. Further genetic analysis revealed that rock1 had only weak or no effect in suppressing shoot phenotypes of mutant plants lacking two or all three CK receptors, respectively. Similarly, the phenotype of mutants lacking multiple CK biosynthetic isopentenyltransferase (IPT) genes was only partially suppressed by rock1-1. Interestingly, comparable restoration of ipt3,5,7 growth was induced by the application of a chemical inhibitor of CKX activity.

Together, the extensive genetic analysis indicated that the main molecular targets of rock1 in suppressing CK deficiency are CKX proteins associated with the secretory pathway. To test this hypothesis biochemically, the CKX activity in 35S:CKX1 parental line and rock1 suppressor was compared. Whereas the CKX activity in 35S:CKX1 seedlings was 22-fold higher in comparison to wild type, rock1 reduced the activity to a level only three-fold higher than that of wild type (FIG. 1D). Likewise, the CKX activities in 35S:CKX2 and 35S:CKX3 plants were reduced through rock1 introgression by 64% and 100%, respectively (FIG. 1D), supporting the notion of rock1 affecting CKX proteins.

ROCK1 Encodes an NST Transporting UDP-GlcNAc and UDP-GalNAc

The rock1-1 mutation was mapped to a 49-kb interval on chromosome 5. Sequencing candidate genes revealed a G-to-A transition in the first exon of the At5g65000 gene leading to a Gly-to-Arg substitution at amino acid position 29. This substitution localizes into the first predicted transmembrane domain of the previously uncharacterized protein of the NST family. A mutation, thin-exine2 (tex2), in At5g65000 gene was previously linked to defective pollen exine production. Introduction of a genomic complementation construct into rock1-1 35S:CKX1 plants resulted in a full recapitulation of 35S:CKX1 phenotypes, confirming that the rock1-1 mutation was causative for the suppression phenotype. This was further corroborated by isolating two T-DNA insertion null alleles, rock1-2 and rock1-3, which displayed similar developmental changes as rock1-1 (see below).

To identify the subcellular compartment in which ROCK1 functions, we transiently expressed ROCK1 N- and C-terminally fused to GFP under control of the 35S promoter in Nicotiana benthamiana and studied the cellular distribution of the fluorescence signal. The expression of GFP-ROCK1 led to a reticulate GFP signal that co-localized with an ER, but not Golgi, marker (FIG. 2A). In contrast, the ROCK1-GFP fusion clearly colocalized with the Golgi marker, suggesting the possible presence of a C-terminal ER retention/retrieval signal. Indeed, after deleting six C-terminal amino acids in GFP-ROCK1 (GFP-ROCK1$^{1-319}$) containing a cluster of five Lys-residues, the GFP signal localized mainly in motile dots colocalizing with a Golgi marker and only a very weak ER signal was observed (FIG. 2A). To rule out the possibility that the N-terminal GFP fusion masked an important localization signal, ROCK1 was internally fused with GFP (ROCK1-GFPin) and expressed stably under the ROCK1 promoter in rock1-1 plants. A characteristic net-like GFP signal was detected indicating that the fusion protein localized to the ER. Again, a C-terminal truncation (ROCK1ROCK1$^{1-319}$-GFPin) re-localized the GFP signal into the Golgi and only weak ER signal was detected. Interestingly, both constructs were able to fully complement rock1-1 35S:CKX1 plants. Together, these results revealed that ROCK1 is an ER-resident protein whose localisation is largely controlled by its C-terminal di-lysine motif.

The molecular function of ROCK1 has so far not been directly studied. The sequence analysis showed that the closest homologos in Arabidopsis are two proteins with unknown function, AT2G43240, AT4G35335, and CMP-sialic acid transporter AT5G41760 with only low, ~15%, sequence identity to ROCK1 suggesting that the substrate cannot be inferred from the sequence comparison and, also, that no functional paralogs may exists in Arabidopsis. Consistently, usually a single orthologous sequence was identified in other sequenced plant species. To directly test the transport specificity of ROCK1, a FLAG-tagged ROCK1 protein was expressed in Saccharomyces cerevisiae, which has, with the exception of GDP-Man, a low background for most nucleotide sugar transport activities and is commonly used as a heterologous test system for NSTs. ER/Golgi microsomal vesicles isolated from ROCK1 and empty vector control transformed cells were in vitro tested for transport activity with a range of commercially available radiolabeled nucleotide sugars (FIG. 2B). In vesicles expressing ROCK1 the uptake of UDP-GalNAc and UDP-GlcNAc was 7- and 3-fold increased, respectively, in comparison to the control (FIG. 2B). A low but significant increase was also detected for UDP-Glc. Interestingly, the relative transport of GDP-Man and GDP-Fuc, which is also mediated by the intrinsic yeast GDP-Man transporter, was, for unknown reasons, lowered in the ROCK1 microsomes. Taken together, these data clearly show that ROCK1 functions as a NST transporting UDP-GalNAc and UDP-GlcNAc as main substrates.

ROCK1 Regulates the Activity of the Shoot Apical Meristem

To understand the function of ROCK1 under physiological conditions, we analyzed the rock1 mutations in the absence of the 35S:CKX1 transgene. The most prominent morphological changes were observed during generative growth, which was overall accelerated in rock1 plants. All three rock1 mutants developed enlarged inflorescences (FIG. 3A) and detailed analysis showed that the frequency of flower initiation was increased by 30% in comparison to wild type (FIG. 3B). Additionally, stem elongation was accelerated by up to 23% (FIG. 3B).

Seven weeks after germination rock1 had generated ~50% more flowers and siliques on the main stem than did the wild type (FIG. 3B). Continuous flower initiation results from the activity of the inflorescence meristem (IM). Scanning electron microscopy analysis revealed that the IM in rock1 was strongly enlarged and initiated supernumerary flower primordia (FIG. 3C) demonstrating that the enhanced flower formation in rock1 plants was due to increased IM activity and that ROCK1 plays a negative regulatory role in this process. These phenotypic changes were strongly reminiscent to those caused by the loss of the CKX3 and CKX5 genes.

Transcript levels of A-type ARR genes were elevated in rock1 shoots and the activity of the CK reporter ARR5:GUS was increased in the shoot meristem of rock1 plants (FIG. 3D) suggesting that ROCK1 regulates SAM activity through adjusting CK signaling in the meristem. The endogenous CK levels were increased up to 35% in rock1 inflorescences in comparison to the control (Tables S4 and S5). In accordance with the observed changes in meristem development, the ROCK1:ROCK1-GUS reporter construct revealed that ROCK1 is strongly expressed in the SAM and young flowers (FIG. 3E), supporting a direct role of ROCK1 in regulating shoot meristem development. The reporter construct further revealed expression of ROCK1 in numerous other tissues, however, we observed neither changes in root development nor altered responses to exogenous CK in rock1 roots supporting the notion that ROCK1 is more relevant for regulating CK responses in the shoot.

To analyze whether rock1 alters CK responses through regulating CKX activity also under physiological conditions, we performed feeding experiments in which we supplied plants with radiolabeled CK (isopentenyladenine, iP) and followed its metabolic conversion. The level of degradation products of CKX reaction was reduced in rock1 plants by 30% after 2 hours incubation, whereas the fraction containing iP with the corresponding riboside and nucleotide was significantly larger in comparison to wild type (FIG. 3F). This further substantiate a ROCK1 regulatory function in tuning CKX-mediated CK degradation.

ROCK1 Plays an Important Role in ERQC

As next we aimed to analyze the molecular mechanism underlying the regulation of CKX activity and to understand the function of ROCK1-transported substrates in this process. Whereas there is virtually no cellular activity requiring UDP-GalNAc known in plants, UDP-GlcNAc is a substrate of GnT-I in a step converting high-mannose to hybrid and complex N-glycans. We tested CKX1 glycosylation and the nature of linked N-glycans. Total proteins from Arabidopsis plants expressing N-terminally myc-tagged CKX1 (myc-CKX1) from the 35S promoter were extracted and subjected to treatment with peptide N-glycosidase F (PNGase F) removing all N-linked oligosaccharides except those carrying core α1,3-fucose. Immunoblot analysis revealed an electrophoretic mobility shift of myc-CKX1 (FIG. 4A) showing that the protein contains N-linked oligosaccharides. Treatment with endoglycosidase H (EndoH), which is unable to cleave complex N-glycans, resulted in a similar mobility shift of myc-CKX1, suggesting that CKX1 contains mainly high-mannose N-glycans. Interestingly, ROCK1 is not substantially involved in CKX1 N-glycosylation as myc-CKX1 extracted from rock1-1 plants showed no obvious difference in mass when compared to myc-CKX1 from wild type and was comparably affected by PNGase F and EndoH treatment (FIG. 4A). Similarly, rock1 did not influence the overall protein modification with complex N-glycans as indicated by the immunoblot analysis with antibodies against complex N-glycans. To test unequivocally whether CKX1 activity is dependent on hybrid or complex N-glycans the complex glycans less 1 (cgl1) mutation of GnT-I was introgressed into 35S:CKX1 plants. As FIG. 4B shows, cgl1-2 had no effect on the 35S:CKX1 phenotype, indicating that CKX1 function is independent of GnT-I activity and further supporting the idea that ROCK1 is not providing UDP-GlcNAc for this reaction.

The protein immunoblot analysis revealed that the level of myc-CKX1 was consistently lower in rock1-1 compared to wild type (FIG. 4C), suggesting that CKX1 protein abundance might be controlled by ROCK1. To test CKX1 turnover, we analyzed myc-CKX1 levels in the presence of the translation inhibitor cycloheximide (CHX). As shown in FIG. 4D, myc-CKX1 was relatively unstable, with a half-life of ~4 h. The turnover of myc-CKX1 in rock1 was comparable to wild type (FIG. 4D). Interestingly, treatment with MG132, a widely used inhibitor of the proteasome, increased the level of myc-CKX1 in wild type (FIG. 4E), indicating that CKX1 protein, which has been shown to localize to the ER/secretory system, is degraded by a proteasome-dependent ERAD mechanism. Intriguingly, inhibition of the proteasome in the rock1 background strongly stabilized myc-CKX1 levels (FIG. 4E) suggesting that the lower myc-CKX1 steady-state levels in rock1 were caused by increased ERAD. Reduced levels of myc-CKX1 could thus indicate inefficient protein processing and folding. This was supported by the analysis of the UPR status through measuring the expression level of typical ER stress response genes, encoding components of the ER protein-folding machinery. FIG. 4F shows that the steady state transcript levels of the binding protein 1 (BiP1), calnexin 1 (CNX1) and calreticulin 2 (CRT2) genes were significantly increased by up to two-fold in rock1 plants in comparison to wild type, demonstrating that UPR was constitutively enhanced and further suggesting defects in ERQC caused by the rock1 mutation. To address this question experimentally, we utilized a mutant allele of the brassinosteroid receptor gene, brassinosteroid insensitive1-9 (bri1-9). The gene product is functionally competent as a hormone receptor but is retained by the ERQC system and degraded by ERAD, causing severe dwarfing of this receptor mutant (FIG. 4G). Introgression of rock1-2 into bri1-9 led to a strong suppression of the dwarf bri1-9 phenotype (FIG. 4G) indicating that bri1-9 leaked from its ER retention machinery, which became compromised in rock1 in a similar fashion as described for other suppressor genes of bri1-9. This was confirmed by the detection of EndoH-resistant, complex N-glycan-carrying, form of bri1-9 in rock1. Hence, our data indicate that ROCK1 is a very important component of the protein folding machinery and/or ERQC in plants.

SUMMARY

The formation of glycoconjugates depends on nucleotide sugars which serve as donor substrates for glycosyltransferases in the lumen of Golgi-vesicles and the endoplasmic reticulum (ER). Import of nucleotide sugars from the cytosol is an important prerequisite for these reactions and is mediated by nucleotide sugar transporters (NSTs). Here, we report the identification of REPRESSOR OF CYTOKININ DEFICIENCY1 (ROCK1, At5g65000) as an ER-localized facilitator of UDP-N-acetylglucosamine (UDP-GlcNAc) and UDP-N-acetylgalactosamine (UDP-GalNAc) transport in *Arabidopsis thaliana*. Mutant alleles of ROCK1 suppress phenotypes inferred by a reduced concentration of the plant hormone cytokinin. This suppression is caused by the loss of activity of cytokinin-degrading enzymes, cytokinin oxidases/dehydrogenases (CKXs). Cytokinin plays an essential role in regulating shoot apical meristem (SAM) activity and shoot architecture. We show that rock1 enhances SAM activity and organ formation rate, demonstrating an important role of ROCK1 in regulating the cytokinin signal in the meristematic cells through modulating activity of CKX proteins. Intriguingly, genetic and molecular analysis showed that formation of complex and hybrid N-linked sugars on CKX1 was not affected by the lack of ROCK1-mediated supply of GlcNAc. In contrast, we show that CKX1 stability is regulated in a proteasome-dependent manner and that ROCK1 regulates the CKX1 level. The increased unfolded protein response in rock1 plants and suppression of phenotypes caused by the defective brassinosteroid receptor bri1-9 strongly suggest that the ROCK1 activity is an important part of the ER quality control system eliminating improperly folded proteins from the secretory pathway.

Significance Statement:

Nucleotide sugars are donor substrates for the formation of glycan modifications, which are important for the function of many macromolecules such as proteins and lipids. Although most of the glycosylation reactions occur in the ER and Golgi of eukaryotic cells, nucleotide sugar activation occurs in the cytosol and specific transporters must carry these molecules across the membrane. We identified ROCK1 as an ER-localized transporter of UDP-GlcNAc and UDP-GalNAc in plants. In contrast to animals, nothing is known about the function of the two respective sugar residues in the plant ER. We demonstrate that ROCK1-mediated transport plays a role in the ER-associated protein quality control and loss of ROCK1 enhances cytokinin responses by suppressing the activity of cytokinin-degrading CKX proteins.

Tables:

TABLE S1

Genetic analysis of rock1-1 mutation.

| | No. of analyzed plants | No. of plants with suppressor phenotype | No. of plants with 35S:CKX1 phenotype | Phenotypic ratio (suppressor: 35S:CKX1) |
|---|---|---|---|---|
| rock1-1 35S:CKX1 × Col-0 | 60 | 30 | 30 | 1:1 |
| rock1-1 35:CKX1 × 35S:CKX1 | 87 | 23 | 64 | 1:2.8 |

The isolated rock1-1 35S:CKX1 line was crossed to wild type (Col-0) and the phenotypic segregation ratio scored in the F2 generation. The observed ratio of plants showing the suppressor and the 35S:CKX1 phenotype fits to the expected ratio for a recessive mutation (1:1.3) ($\chi^2$-test for goodness of fit, $\chi^2 = 0.952$, P = 0.329).
The isolated rock1-1 35S:CKX1 line was crossed to 35S:CKX1 and the phenotypic segregation scored in the F2 generation. The observed ratio of plants showing the suppressor and the 35S:CKX1 phenotype fits to the expected ratio for a recessive mutation (1:3) ($\chi^2$-test for goodness of fit, $\chi^2 = 0.096$, P = 0.757).

TABLE S2 rock1-1 increases cytokinin content in 35S:CKX1 plants.

| | Experiment 1 | Experiment 2 |
|---|---|---|
| 35S:CKX1 | 4 | 21 |
| rock1-1 35S:CKX1 | 19 | 45 |

Values represent the sum of all measured trans-zeatin-, cis-zeatin- and isopentenyl-type cytokinins in the mutant relative to the wild type (in percent).
Used material: experiment 1, shoots from seedlings 10 dag; experiment 2, inflorescences of 4-week-old plants including flowers till stage 15 (23).

TABLE S3

Cytokinin levels (pmol g$^{-1}$ fresh weight) in different tissues of wild-type, 35S:CKX1 and rock1-1 35S:CKX1 plants.

| CKs | Wild type shoot | 35S:CKX1 shoot | rock1-1 35S:CKX1 shoot | Wild type inflorescence | 35S:CKX1 inflorescence | rock1-1 35S:CKX1 inflorescence |
|---|---|---|---|---|---|---|
| tZ | 0.17 ± 0.03 | 0.02 ± 0.00 | 0.03 ± 0.01 | 2.30 ± 0.10 | <LOD | 0.81 ± 0.02 |
| tZR | 0.14 ± 0.02 | 0.03 ± 0.00 | 0.06 ± 0.01 | 71.71 ± 6.87 | 3.52 | 14.62 ± 1.70 |
| tZOG | 7.96 ± 1.11 | 0.07 ± 0.01 | 1.78 ± 0.15 | 0.39 ± 0.06 | <LOD | 0.63 ± 0.09 |
| tZROG | 0.27 ± 0.05 | <LOD | 0.07 ± 0.01 | 1.69 ± 0.25 | <LOD | 0.76 ± 0.08 |
| tZ7G | 63.23 ± 2.67 | 0.62 ± 0.15 | 8.38 ± 0.82 | 17.28 ± 0.41 | 0.84 | 21.25 ± 0.41 |
| tZ9G | 5.24 ± 0.23 | 0.02 ± 0.01 | 0.66 ± 0.06 | 1.38 ± 0.12 | <LOD | 1.16 ± 0.11 |
| tZR5MP | 2.76 ± 0.44 | 0.02 ± 0.00 | 0.44 ± 0.06 | 2.74 ± 0.32 | <LOD | 1.22 ± 0.07 |
| cZ | 0.03 ± 0.01 | 0.01 ± 0.00 | 0.01 ± 0.00 | 0.24 ± 0.02 | <LOD | 0.10 ± 0.04 |
| cZR | 0.13 ± 0.01 | 0.05 ± 0.01 | 0.07 ± 0.01 | 24.69 ± 3.42 | 18.41 | 6.66 ± 1.05 |
| cZOG | 0.21 ± 0.05 | 0.09 ± 0.02 | 0.10 ± 0.01 | 0.16 ± 0.04 | <LOD | <LOD |
| cZROG | 0.41 ± 0.07 | 0.19 ± 0.04 | 0.24 ± 0.03 | 1.42 ± 0.09 | <LOD | 0.35 ± 0.04 |
| cZ9G | 0.12 ± 0.00 | <LOD | 0.01 ± 0.00 | <LOD | <LOD | 0.03 ± 0.00 |
| cZR5MP | 2.99 ± 0.24 | 0.26 ± 0.06 | 0.79 ± 0.07 | 1.80 ± 0.14 | 1.19 | 1.04 ± 0.10 |
| iP | 0.47 ± 0.04 | 0.23 ± 0.05 | 0.17 ± 0.04 | 0.18 ± 0.03 | <LOD | 0.11 ± 0.02 |
| iPR | 0.55 ± 0.04 | 0.20 ± 0.04 | 0.34 ± 0.05 | 7.82 ± 0.86 | 1.47 | 2.56 ± 0.42 |
| iP7G | 79.62 ± 9.13 | 1.66 ± 0.29 | 15.00 ± 1.12 | 5.49 ± 0.14 | 3.38 | 10.28 ± 0.30 |
| iP9G | 1.57 ± 0.08 | <LOD | 0.12 ± 0.01 | 0.08 ± 0.01 | <LOD | 0.12 ± 0.01 |
| iPR5MP | 11.97 ± 1.86 | 3.46 ± 0.51 | 5.04 ± 0.33 | 2.09 ± 0.20 | 0.63 | 1.63 ± 0.15 |

Analyzed tissue: shoot, shoots of seedlings 10 dag; inflorescence, inflorescences of 4-week-old plants up to flowers at stage 15 according to Smyth et al. (23). Shown are mean values ± SD. (n = 3), except for 35S:CKX1 inflorescence (n = 1). LOD, limit of detection. tZ, trans-zeatin; cZ, cis-zeatin; iP, isopentenyladenine; -R, -riboside; -OG, O-glucoside; -ROG, -riboside-O-glucoside; -7G/-9G, N7-/N9-glucoside; -R5MP, riboside 5'-monophosphate.

TABLE S4 rock1 plants have an increased cytokinin content.

| | |
|---|---|
| rock1-1 | 113 |
| rock1-2 | 135 |

Values represent the sum of all measured trans-zeatin-, cis-zeatin- and isopentenyl-type cytokinins in the mutant relative to the wild type (in percent).
Used material: inflorescences of 4-week-old plants including flowers till stage 15 according to Smyth et al. (23).

TABLE S5

Cytokinin levels (pmol g$^{-1}$ fresh weight) in wild-type, rock1-1 and rock1-2 inflorescence tissues.

| CKs | Wild type inflorescence | rock1-1 inflorescence | rock1-2 inflorescence |
|---|---|---|---|
| tZ | 2.30 ± 0.10 | 2.12 ± 0.08 | 2.55 ± 0.08 |
| tZR | 71.71 ± 6.87 | 63.38 ± 1.83 | 76.39 ± 0.96 |
| tZOG | 0.39 ± 0.06 | 0.77 ± 0.11 | 0.67 ± 0.06 |
| tZROG | 1.69 ± 0.25 | 2.71 ± 0.39 | 3.10 ± 0.40 |
| tZ7G | 17.28 ± 0.41 | 37.97 ± 1.81 | 48.15 ± 4.56 |
| tZ9G | 1.38 ± 0.12 | 3.36 ± 0.17 | 3.85 ± 0.15 |
| tZR5MP | 2.74 ± 0.32 | 3.73 ± 0.01 | 4.29 ± 0.73 |
| cZ | 0.24 ± 0.02 | 0.19 ± 0.02 | 0.28 ± 0.04 |
| cZR | 24.69 ± 3.42 | 15.16 ± 2.00 | 21.59 ± 1.48 |
| cZOG | 0.16 ± 0.04 | 0.20 ± 0.05 | 0.27 ± 0.05 |
| cZROG | 1.42 ± 0.09 | 1.55 ± 0.20 | 1.78 ± 0.31 |
| cZ9G | <LOD | 0.06 ± 0.01 | 0.07 ± 0.01 |
| cZR5MP | 1.80 ± 0.14 | 1.78 ± 0.18 | 1.93 ± 0.28 |
| iP | 0.18 ± 0.03 | 0.23 ± 0.21 | 0.24 ± 0.01 |
| iPR | 7.82 ± 0.86 | 9.26 ± 0.36 | 9.19 ± 0.40 |
| iP7G | 5.49 ± 0.14 | 12.58 ± 0.02 | 13.46 ± 0.91 |
| iP9G | 0.08 ± 0.01 | 0.14 ± 0.02 | 0.10 ± 0.01 |
| iPR5MP | 2.09 ± 0.20 | 4.45 ± 0.34 | 3.51 ± 0.43 |

Analyzed tissue: inflorescences of 4-week-old plants up to flowers at stage 15 according to Smyth et al. (23). Shown are mean values ± SD (n = 3). LOD, limit of detection. tZ, trans-zeatin; cZ, cis-zeatin; iP, isopentenyladenine; -R, -riboside; -OG, O-glucoside; -ROG, -riboside-O-glucoside; -7G/-9G, N7-/N9-glucoside; -R5MP, riboside 5'-monophosphate.

TABLE S6

Primers used for genotyping and molecular characterization of transgenic lines.

| Allele | Sequence (5'-3') | SEQ ID NO: |
|---|---|---|
| ROCK1 | TGAGAAAACGACGTCCAATG | 40 |
| | TAAACCCGACAGGACAGAGG | 41 |
| rock1-2 | TGGTTCACGTAGTGGGCCATCG | 42 |
| | TAAACCCGACAGGACAGAGG | 43 |
| rock1-3 | TGAGAAAACGACGTCCAATG | 44 |
| | ATATTGACCATCATACTCATTGC | 45 |
| AHK2 | GCAAGAGGCTTTAGCTCCAA | 46 |
| | TTGCCCGTAAGATGTTTTCA | 47 |
| ahk2-5 | GCAAGAGGCTTTAGCTCCAA | 48 |
| | GCCTTTTCAGAAATGGATAAATAGCCTTGCTTCC | 49 |
| AHK3 | CCTTGTTGCCTCTCGAACTC | 50 |
| | CGCAAGCTATGGAGAAGAGG | 51 |
| ahk3-7 | CCCATTTGGACGTGTAGACAC | 52 |
| | CGCAAGCTATGGAGAAGAGG | 53 |
| AHK4 | GGGCACTCAACAATCATCAA | 54 |
| | TCCACTGATAAATCCCACTGC | 55 |
| cre1-2 | ATAACGCTGCGGACATCTAC | 56 |
| | TCCACTGATAAATCCCACTGC | 57 |
| IPT1 | CCACGATTCGACCCAAAGTT | 58 |
| | GCTCCAACACTTGCTCTTCC | 59 |
| ipt1 | CCACGATTCGACCCAAAGTT | 60 |
| | TGGTTCACGTAGTGGGCCATCG | 61 |

TABLE S6-continued

Primers used for genotyping and molecular characterization of transgenic lines.

| Allele | Sequence (5'-3') | SEQ ID NO: |
|---|---|---|
| IPT3 | CCAACTTGTCGTATATCATTCGTACAGTG | 62 |
|  | TGGAGAGATTCGCCATGTGACAG | 63 |
| ipt3-2 | CCAACTTGTCGTATATCATTCGTACAGTG | 64 |
|  | CAACACGTGGGTTAATTAAGAATTCAGTAC | 65 |
| IPT5 | TGCATGACGGCTCTAAGACA | 66 |
|  | TCGAGCTCTGGAACTCCAAT | 67 |
| ipt5-2 | TGGTTCACGTAGTGGGCCATCG | 68 |
|  | TCGAGCTCTGGAACTCCAAT | 69 |
| IPT7 | CTACCGGATCGGGTAAGTCTC | 70 |
|  | GCTACAAGATTCTCCCAAGCC | 71 |
| ipt7-1 | CTACCGGATCGGGTAAGTCTC | 72 |
|  | TGGTTCACGTAGTGGGCCATCG | 73 |
| rock1-2/rock1-3 primer 1 | GTATGGGCCCTAAGGTTTTG | 74 |
| rock1-2/rock1-3 primer 2 | ATACGATGATGGCGGTTTTC | 75 |
| rock1-3 primer 3 | GGCTAACGGAGCAAAGAGT | 76 |
| rock1-3 primer 4 | CAGCGTTTGGAGATCAGAG | 77 |
| rock1-3 primer 5 | GCTCTGATTCTCATGGCAAG | 78 |
| rock1-3 primer 6 | TGCTGTGAAAAAGATTTTCGTCT | 79 |
| Actin7 fw | TACAACGAGCTTCGTGTTGC | 80 |
| Actin7 rev | TCCACATCTGTTGGAAGGTG | 81 |

TABLE S7

Primers used for genotyping of mutants by dCAPS analysis.

| Allele | Sequence (5'-3') | SEQ ID NO: | Restriction enzyme |
|---|---|---|---|
| rock1-1 | TTCCATATTGCTCACACTTCAGTAC | 82 | Bsp1407I |
|  | AAACAGATGCCCAGAAATCG | 83 |  |
| cgl1-2 | CATAACCTTGTTATATTAATTTGCCA | 84 | Eco130I |
|  | AGGCCGGAGTTCTGTAAATG | 85 |  |

TABLE S8

Primers used for quantitative real-time PCR.

| Transcript | Sequence (5'-3') | SEQ ID NO: |
|---|---|---|
| β-Tubulin | GAGCCTTACAACGCTACTCTGTCTGTC | 86 |
|  | ACACCAGACATAGTAGCAGAAATCAAG | 87 |
| ARR5 | CTACTCGCAGCTAAAACGC | 88 |
|  | GCCGAAAGAATCAGGACA | 89 |
| ARR6 | GAGCTCTCCGATGCAAAT | 90 |
|  | GAAAAAGGCCATAGGGGT | 91 |
| ARR7 | CTTGGAACCAATCTGCTCTC | 92 |
|  | ATCATCGACGGCAAGAAC | 93 |
| CKX1 | ACGACCCTCTAGCGATTCT | 94 |
|  | CGGCAGTATTGATGCGTA | 95 |
| ROCK1 | GGCTAACGGAGCAAAGAGT | 96 |
|  | CAGCGTTTGGAGATCAGAG | 97 |
| BiP1 | ACGTACCAAGACCAGCAGACTACC | 98 |
|  | TGCAGTCCTTGGTGAGACTTCG | 99 |
| CRT2 | TGGACTCGAATTGTGGCAGGTG | 100 |
|  | TGCCAACTTCTTGGCATAGTCTGG | 101 |
| CNX1 | TCTGCAGATGGTCTCAAGAGCTAC | 102 |
|  | CTCGGCTTTCTCAATCAGTTCCG | 103 |

TABLE S9

Primers used for cloning.

| Primer | Sequence (5'-3') | SEQ ID NO: |
|---|---|---|
| 1 | CGGAGCTCGGCAGGCTTCATGATTGATT | 104 |
| 2 | CGGAGCTCTCAATGGGTTGATTTGCGTA | 105 |
| 3 | CGCGGCTAGCCGGCCGTTGATTTTGACTAT | 106 |
| 4 | CGCGGCTAGCCACCTTCTTCTTCTTCTTGTC | 107 |
| 5 | CATAGGTACCTGCGACGGCTAACGGAGC | 108 |
| 6 | GTCTGAATTCTTACACCTTCTTCTTCTTCTTGTC | 109 |
| 7 | AAAAAGCAGGCTTTATGGGATTGACCTC | 110 |
| 8 | AGAAAGCTGGGTTCTAACTCGAGTTTATTTTTTG | 111 |
| 9 | GGGGACAAGTTTGTACAAAAAAGCAGGCT | 112 |
| 10 | GGGGACCACTTTGTACAAGAAAGCTGGGT | 113 |
| 11 | AAAAAGCAGGCTTCACCATGGCGACGGCTAACGGAGCAAA | 114 |
| 12 | AGAAAGCTGGGTGTTACACCTTCTTCTTCTTCTTGTC | 115 |
| 13 | AGAAAGCTGGGTGTTAGTCAATGTATGGGTATTTCTG | 116 |

TABLE S9-continued

Primers used for cloning.

| Primer | Sequence (5'-3') | SEQ ID NO: |
|---|---|---|
| 14 | AGAAAGCTGGGTGCACCTTCTTCTTCTTCTTGTC | 117 |
| 15 | ATTAATATGGTGAGCAAGGGCGAGGAGCTG | 118 |
| 16 | ATTAATCTTGTACAGCTCGTCCATGCCGA | 119 |
| 17 | CAGAATTCTTAGTCAATGTATGGGTATTTCTGGTA | 120 |

The invention claimed is:

1. A method for producing a plant with an improved yield-related trait the method comprising:
   introducing into the genome of a plant cell a disruption of endogenous ROCK1 gene, wherein said disruption inhibits expression and/or activity of a product of said endogenous ROCK1 gene compared to a corresponding plant cell lacking such a disruption, wherein the endogenous ROCK1 gene comprises:
   (a) a nucleic acid encoding a ROCK1 protein comprising the amino acid sequence of SEQ ID NO: 1 or 2 or an orthologue thereof;
   (b) a nucleic acid encoding a ROCK1 protein comprising an amino acid sequence with a sequence identity of at least 55% over the entire amino acid sequence with SEQ ID NO: 1 or 2;
   (c) a nucleic acid comprising one of the nucleic acid sequences with SEQ ID NO: 4, 5, 6, 7 and/or 8;
   (d) a nucleic acid comprising a nucleic acid with a sequence identity of at least 60% over the entire nucleic acid sequence with one of SEQ ID NO: 4, 5, 6, 7 and/or 8; or
   (e) a nucleic acid hybridizing under stringent conditions to one of the nucleic acid sequences defined under (a), (b), (c), and/or (d);
   regenerating a plant having such an altered genome from said plant cell; and
   measuring a yield-related trait of said plant compared to a plant lacking such disruption, wherein the yield-related trait is selected from the group consisting of: number of flowers, number of siliques, shoot growth, and seed yield.

2. The method of claim 1, wherein the disruption is introduced by at least one of: structural disruption, T-DNA insertion, antisense polynucleotide gene suppression, double stranded RNA induced gene silencing, ribozyme techniques, genomic disruption, tilling, transcriptional activator-like effector nucleases, zink finger nucleases, homing meganucleases, CRISPR/Cas technology and homologous recombination.

3. The method of claim 1, wherein the disruption comprises more than one disruption and all disruptions are homozygous disruptions.

4. The method of claim 1, wherein the endogenous ROCK1 gene comprises:
   (a) a nucleic acid encoding a ROCK1 protein comprising one of the amino acid sequences of SEQ ID NO: 1, 2 and/or 9 to 39;
   (b) a nucleic acid encoding a ROCK1 protein comprising an amino acid sequence with a sequence identity of at least 55% over the entire amino acid sequence with SEQ ID NO: 1, 2 and/or 9 to 39;
- (c) a nucleic acid comprising one of the nucleic acid sequences with SEQ ID NO: 4, 5, 6, 7 and/or 8;
- (d) a nucleic acid comprising a nucleic acid with a sequence identity of at least 60% over the entire nucleic acid sequence with one of SEQ ID NO: 4, 5, 6, 7 and/or 8; or
- (e) a nucleic acid hybridizing under stringent conditions to one of the nucleic acid sequences defined under (a), (b), (c), and/or (d).

5. The method of claim 1, wherein the plant is a monocotyledonous plant, a dicotyledonous plant, a moss or an algae.

6. The method of claim 1, wherein the plant is selected from a family of the group consisting of: Brassicaceae, Rosaceae, Fabaceae, Poaceae, Vitaceae, Solanaceae, Salicaceae, Malvaceae, Pinaceae, Funariaceae Rutaceae, Rubiacea, Musaceae and Selaginellaceae.

7. The method of claim 6, wherein the family is Brassicaceae, Poaceae, Rosaceae, Solanaceae, Malvaceae, Salicaceae or Fabaceae.

8. The method of claim 1, wherein the yield-related trait is number of flowers.

9. The method of claim 1, wherein the yield-related trait is number of siliques.

* * * * *